US012697395B2

(12) United States Patent (10) Patent No.: US 12,697,395 B2
Hangasky, III et al. (45) Date of Patent: Aug. 4, 2026

(54) SLOW-RELEASE CYTOKINE CONJUGATES

(71) Applicant: ProLynx LLC, San Francisco, CA (US)

(72) Inventors: John A. Hangasky, III, San Francisco, CA (US); Samuel J. Pfaff, San Francisco, CA (US); Daniel V. Santi, San Francisco, CA (US)

(73) Assignee: ProLynx LLC, San Francisco, CA (US)

( * ) Notice: Subject to any disclaimer, the term of this patent is extended or adjusted under 35 U.S.C. 154(b) by 1169 days.

(21) Appl. No.: 17/606,687

(22) PCT Filed: Apr. 24, 2020

(86) PCT No.: PCT/US2020/029911
    § 371 (c)(1),
    (2) Date: Oct. 26, 2021

(87) PCT Pub. No.: WO2020/219943
    PCT Pub. Date: Oct. 29, 2020

(65) Prior Publication Data
    US 2022/0193253 A1     Jun. 23, 2022

Related U.S. Application Data

(60) Provisional application No. 62/839,112, filed on Apr. 26, 2019.

(51) Int. Cl.
| | |
|---|---|
| *A61K 47/69* | (2017.01) |
| *A61K 38/19* | (2006.01) |
| *A61K 38/20* | (2006.01) |
| *A61K 47/60* | (2017.01) |
| A61P 37/02 | (2006.01) |

(52) U.S. Cl.
    CPC .......... *A61K 47/6903* (2017.08); *A61K 38/19* (2013.01); *A61K 38/2013* (2013.01); *A61K 47/60* (2017.08); *A61K 47/6925* (2017.08); *A61P 37/02* (2018.01)

(58) Field of Classification Search
    CPC ................ A61K 47/6903; A61K 38/19; A61K 38/2013; A61K 47/60; A61K 47/6925; A61K 38/00; A61P 25/00; C07K 14/55
    See application file for complete search history.

(56) References Cited

U.S. PATENT DOCUMENTS

| | | | |
|---|---|---|---|
| 8,268,773 B2 | 9/2012 | Presnell et al. | |
| 8,680,315 B2 | 3/2014 | Santi et al. | |
| 8,703,907 B2 | 4/2014 | Ashley et al. | |
| 8,754,190 B2 | 6/2014 | Ashley et al. | |
| 8,946,405 B2 | 2/2015 | Ashley et al. | |
| 9,206,243 B2 | 12/2015 | Monzon et al. | |
| 9,387,254 B2 | 7/2016 | Santi et al. | |
| 9,649,385 B2 | 5/2017 | Ashley et al. | |
| 9,861,705 B2 | 1/2018 | Bossard et al. | |
| 10,016,411 B2 | 7/2018 | Ashley et al. | |
| 10,086,049 B2 | 10/2018 | Schneider et al. | |
| 10,342,792 B2 | 7/2019 | Ashley et al. | |
| 10,358,477 B2 | 7/2019 | Jacques et al. | |
| 10,358,488 B2 | 7/2019 | Hope et al. | |
| 10,398,779 B2 | 9/2019 | Ashley et al. | |
| 10,413,594 B2 | 9/2019 | Schneider et al. | |
| 11,179,470 B2 | 11/2021 | Ashley et al. | |
| 11,181,803 B2 | 11/2021 | Ashley et al. | |
| 11,454,861 B2 | 9/2022 | Ashley et al. | |
| 11,730,836 B2 | 8/2023 | Santi et al. | |
| 12,364,771 B2 | 7/2025 | Ashley et al. | |
| 12,472,261 B2 | 11/2025 | Fontaine et al. | |
| 12,478,680 B2 | 11/2025 | Ashley et al. | |
| 2013/0123461 A1 | 5/2013 | Ashley et al. | |
| 2014/0256626 A1 | 9/2014 | Santi et al. | |
| 2014/0288190 A1 | 9/2014 | Ashley et al. | |
| 2015/0352246 A1 | 12/2015 | Henise et al. | |
| 2017/0204154 A1 | 7/2017 | Greve | |
| 2018/0250363 A1 | 9/2018 | Lee et al. | |
| 2018/0360977 A1 | 12/2018 | McCauley et al. | |
| 2020/0164083 A1 | 5/2020 | Schneider et al. | |
| 2020/0360545 A1 | 11/2020 | Hearn et al. | |
| 2022/0193253 A1 | 6/2022 | Hangasky et al. | |
| 2022/0265873 A1 | 8/2022 | Henise et al. | |
| 2023/0321286 A1 | 10/2023 | Hearn et al. | |
| 2024/0041982 A1 | 2/2024 | Schneider et al. | |
| 2024/0082436 A1 | 3/2024 | Santi et al. | |
| 2024/0181397 A1 | 6/2024 | Henise et al. | |
| 2025/0312498 A1 | 10/2025 | Hearn et al. | |
| 2026/0007768 A1 | 1/2026 | Ashley et al. | |

(Continued)

FOREIGN PATENT DOCUMENTS

| | | |
|---|---|---|
| CN | 103025165 | 4/2013 |
| CN | 106456716 | 2/2017 |
| JP | 2013-525080 | 6/2013 |

(Continued)

OTHER PUBLICATIONS

Li et al. Designing hydrogels for controlled drug delivery. Nat Rev Mater. Dec. 2016 ; 1(12), pp. 1-38 (Year: 2016).*
Henise et al., "Biodegradable Tetra-PEG Hydrogels as Carriers for a Releasable Drug Delivery System," Bioconjugate Chemistry (2015) 26:270-278.
Machinaga et al., "A Controlled Release System for Long-Acting Intravitreal Delivery of Small Molecules," TVST (2018) 7(4):1-8.
Santi et al., "Predictable and tunable half-life extension of therapeutic agents by controlled chemical release from macromolecular conjugates," PNAS (2012) 109(16):6211-6216.

(Continued)

*Primary Examiner* — Shafiqul Haq

(74) *Attorney, Agent, or Firm* — MORRISON & FOERSTER LLP

(57) ABSTRACT

This disclosure generally relates to releasable cytokine conjugates and methods of using the same.

18 Claims, 19 Drawing Sheets

Specification includes a Sequence Listing.

(56) References Cited

U.S. PATENT DOCUMENTS

| | | |
|---|---|---|
| 2026/0034120 A1 | 2/2026 | Santi et al. |
| 2026/0041680 A1 | 2/2026 | Santi et al. |

FOREIGN PATENT DOCUMENTS

| | | | | |
|---|---|---|---|---|
| JP | 2016-518361 | 6/2016 | | |
| JP | 2017-511322 | 4/2017 | | |
| JP | 2017-528444 | 9/2017 | | |
| WO | WO-2002026265 A2 | 4/2002 | | |
| WO | WO-2005099768 A2 | 10/2005 | | |
| WO | WO-2006136586 A2 | 12/2006 | | |
| WO | WO-2006138572 A2 | 12/2006 | | |
| WO | WO-2011012722 A1 | 2/2011 | | |
| WO | WO-2011089214 A1 | 7/2011 | | |
| WO | WO-2011089215 A1 | 7/2011 | | |
| WO | WO-2011089216 A1 | 7/2011 | | |
| WO | WO-2011/140376 | 11/2011 | | |
| WO | WO-2011140392 A1 * | 11/2011 | ......... | A61K 47/6903 |
| WO | WO-2013036847 A1 * | 3/2013 | ........... | G02F 1/3611 |
| WO | WO-2013036857 A1 | 3/2013 | | |
| WO | WO-2014023752 A1 | 2/2014 | | |
| WO | WO-2015153753 A2 * | 10/2015 | .............. | A61P 43/00 |
| WO | WO-2016020373 A1 | 2/2016 | | |
| WO | WO-2017112528 A2 | 6/2017 | | |
| WO | WO-2019/028419 | 2/2019 | | |
| WO | WO-2019028425 A1 | 2/2019 | | |
| WO | WO-2010077853 A2 | 7/2020 | | |
| WO | WO-2020206358 A1 | 10/2020 | | |

OTHER PUBLICATIONS

Schneider et al., Approach for Half-Life Extension of Small Antibody Fragments That Does Not Affect Tissue Uptake, Bioconjugate Chemistry (2016) 27(10):2534-2539.

Schneider et al., "A Hydrogel-Microsphere Drug Delivery System That Supports Once-Monthly Administration of a GLP-1 Receptor Agonist," ACS Chem. Biol. (2017) 12:2107-2116.

Chan et al., (2015). "The Potentiation of IFN-y and Induction of Cytotoxic Proteins by Pegylated IL-10 in Human CD8 T Cells," J Interferon Cytokine Res, 35:948-55.

Elkassar et al., (2010). "An overview of IL-7 biology and its use in immunotherapy," J. Immunotoxicol., 7:1-7.

Emmerich et al., (2012). "IL-10 directly activates and expands tumor-resident CD8(+) T cells without de novo infiltration from secondary lymphoid organs," Cancer Res, 72:3570-81.

Extended European Search Report and Written Opinion received for European Patent Application No. 20795140.1 mailed on Jun. 13, 2023, 14 pages.

Han et al., (2011). "IL-15:IL-15 receptor alpha superagonist complex: high-level co- expression in recombinant mammalian cells, purification and characterization," Cytokine, 56(3):804-10, 18 pages.

Hansch et al., (1991). "A Survey of Hammett Substituent Constants and Resonance and Field Parameters," Chemical Reviews, 91:165-195.

International Search Report and Written Opinion received for International Patent Application No. PCT/US2020/029911 mailed on Aug. 4, 2020, 10 pages.

Koreth et al., (2014). "Low-dose Interleukin-2 in the Treatment of Autoimmune Disease," Oncology & Hematology Review, 10:157-63. Abstract Only.

Koreth et al., (2016). "Efficacy, durability, and response predictors of low-dose interleukin-2 therapy for chronic graft-versus-host disease," Blood, 128:130-7.

Mortier et al., (2006). "Soluble interleukin-15 receptor alpha (IL-15R alpha)-sushi as a selective and potent agonist of IL-15 action through IL-15R beta/gamma. Hyperagonist IL-15 x IL-15R alpha fusion proteins," J. Biological Chem., 281:1612-9.

Mumm et al., (2011). "IL-10 elicits IFNy-dependent tumor immune surveillance," Cancer Cell, 20:781-96.

Nellis et al., (2012). "Characterization of recombinant human IL-15 deamidation and its practical elimination through substitution of asparagine 77," Pharm. Res., 29:722-38.

Roychowdhury et al., (2004). "Failed adoptive immunotherapy with tumor-specific T cells: reversal with low-dose interleukin 15 but not low-dose interleukin 2," Cancer Research, 64:8062-7.

Sneller et al., (2011). "IL-15 administered by continuous infusion to rhesus macaques induces massive expansion of CD8+ T effector memory population in peripheral blood," Blood, 118:6845-8.

Xiao et al., (2017). "Osteoblasts support megakaryopoiesis through production of interleukin-9," Blood, 129:3196-3209.

Zheng et al., (1996). "Interleukin-10 inhibits tumor metastasis through an NK cell- dependent mechanism," J. Exp.Med., 184:579-84.

Zhu et al., (2009). "Novel human interleukin-15 agonists," J. Immunology, 183(6):3598-607, 28 pages.

* cited by examiner

Lane 1. Novex MW Ladder

Lane 2. IL-15 only.

Lane 3. IL-15 and PEG$_{5K}$.

Lane 4. Alk. IL-15, 1.0x PEG$_{5K}$.

Lane 5. Alk. IL-15, 3x PEG$_{5K}$.

Lane 6. Alk. IL-15, 5.0x PEG$_{5K}$.

SEQUENCE LISTING

```
<160> NUMBER OF SEQ ID NOS: 21

<210> SEQ ID NO 1
<211> LENGTH: 132
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Leu Thr
    130

<210> SEQ ID NO 2
<211> LENGTH: 133
<212> TYPE: PRT
<213> ORGANISM: Artificial Sequence
<220> FEATURE:
<223> OTHER INFORMATION: Synthetic Construct

<400> SEQUENCE: 2

Ala Pro Thr Ser Ser Ser Thr Lys Lys Thr Gln Leu Gln Leu Glu His
```

-continued

```
1               5                    10                   15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130
```

```
<210> SEQ ID NO 3
<211> LENGTH: 133
<212> TYPE: PRT
<213> ORGANISM: Artificial Sequence
<220> FEATURE:
<223> OTHER INFORMATION: Synthetic Construct

<400> SEQUENCE: 3

Ala Pro Thr Ser Ser Ser Thr Lys Lys Thr Gln Leu Gln Leu Glu His
1               5                    10                   15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130
```

```
<210> SEQ ID NO 4
<211> LENGTH: 133
<212> TYPE: PRT
<213> ORGANISM: Artificial Sequence
<220> FEATURE:
<223> OTHER INFORMATION: Synthetic Construct

<400> SEQUENCE: 4

Ala Pro Thr Ser Ser Ser Thr Lys Lys Thr Gln Leu Gln Leu Glu His
1               5                    10                   15

Leu Leu Leu Asp Leu Gln Met Ile Leu Asn Gly Ile Asn Asn Tyr Lys
            20                  25                  30
```

```
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 5
<211> LENGTH: 133
<212> TYPE: PRT
<213> ORGANISM: Artificial Sequence
<220> FEATURE:
<223> OTHER INFORMATION: Synthetic Construct

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 6
<211> LENGTH: 133
<212> TYPE: PRT
<213> ORGANISM: Artificial Sequence
<220> FEATURE:
<223> OTHER INFORMATION: Synthetic Construct

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Lys Met Leu Thr Ile Lys Phe Asn Met Pro Lys
        35                  40                  45

Lys Ala Thr Glu Leu Lys His Leu Gln Cys Leu Glu Glu Leu Leu Lys
        50                  55                  60
```

```
Pro Leu Glu Val Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 7
<211> LENGTH: 133
<212> TYPE: PRT
<213> ORGANISM: Artificial Sequence
<220> FEATURE:
<223> OTHER INFORMATION: Synthetic Construct

<400> SEQUENCE: 7

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Lys Met Leu Thr Gln Lys Phe Glu Met Pro Lys
            35                  40                  45

Lys Ala Thr Glu Leu Lys His Leu Gln Cys Leu Glu Glu Glu Leu Lys
        50                  55                  60

Pro Leu Glu Val Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 8
<211> LENGTH: 133
<212> TYPE: PRT
<213> ORGANISM: Artificial Sequence
<220> FEATURE:
<223> OTHER INFORMATION: Synthetic Construct

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Ala Met Leu Thr Ile Lys Phe Asn Met Pro Lys
            35                  40                  45

Lys Ala Thr Glu Leu Lys His Leu Gln Cys Leu Glu Glu Leu Leu Lys
        50                  55                  60

Pro Leu Glu Val Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
```

-continued

```
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 9
<211> LENGTH: 133
<212> TYPE: PRT
<213> ORGANISM: Artificial Sequence
<220> FEATURE:
<223> OTHER INFORMATION: Synthetic Construct

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Lys Met Leu Thr Lys Lys Phe Arg Met Pro Lys
            35                  40                  45

Lys Ala Thr Glu Leu Lys His Leu Gln Cys Leu Glu Glu Leu Leu Lys
        50                  55                  60

Pro Leu Glu Val Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 10
<211> LENGTH: 133
<212> TYPE: PRT
<213> ORGANISM: Artificial Sequence
<220> FEATURE:
<223> OTHER INFORMATION: Synthetic Construct

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Lys Met Leu Thr Ile Lys Phe Glu Met Pro Lys
            35                  40                  45

Lys Ala Thr Glu Leu Lys His Leu Gln Cys Leu Glu Glu Glu Leu Lys
        50                  55                  60

Pro Leu Glu Val Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110
```

```
Thr Ile Val Glu Phe Leu Asn Arg Trp Ile Thr Phe Cys Gln Ser Ile
    115                 120                 125

Ile Ser Thr Leu Thr
    130

<210> SEQ ID NO 11
<211> LENGTH: 133
<212> TYPE: PRT
<213> ORGANISM: Artificial Sequence
<220> FEATURE:
<223> OTHER INFORMATION: Synthetic Construct

<400> SEQUENCE: 11

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Ala Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
    115                 120                 125

Ile Ser Thr Leu Thr
    130

<210> SEQ ID NO 12
<211> LENGTH: 114
<212> TYPE: PRT
<213> ORGANISM: Homo sapiens

<400> SEQUENCE: 12

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser

<210> SEQ ID NO 13
<211> LENGTH: 114
<212> TYPE: PRT
<213> ORGANISM: Artificial Sequence
```

<220> FEATURE:
<223> OTHER INFORMATION: Synthetic Construct

<400> SEQUENCE: 13

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Ala Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 14
<211> LENGTH: 114
<212> TYPE: PRT
<213> ORGANISM: Artificial Sequence
<220> FEATURE:
<223> OTHER INFORMATION: Synthetic Construct

<400> SEQUENCE: 14

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Ser Ala Ser Leu Ser Ser Ala Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 15
<211> LENGTH: 114
<212> TYPE: PRT
<213> ORGANISM: Artificial Sequence
<220> FEATURE:
<223> OTHER INFORMATION: Synthetic Construct

<400> SEQUENCE: 15

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45
```

Val Ile Ser Leu Glu Ser Gly Asp Ala Ser Ile His Asp Thr Val Glu
        50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 16
<211> LENGTH: 253
<212> TYPE: PRT
<213> ORGANISM: Artificial Sequence
<220> FEATURE:
<223> OTHER INFORMATION: Synthetic Construct

<400> SEQUENCE: 16

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Asp Tyr
            20                  25                  30

Lys Asp Asp Asp Asp Lys Ile Glu Gly Arg Ile Thr Cys Arg Arg Arg
            35                  40                  45

Met Ser Val Glu His Ala Asp Ile Trp Val Lys Ser Tyr Ser Leu Tyr
        50                  55                  60

Ser Arg Glu Arg Tyr Ile Cys Asn Ser Gly Phe Lys Arg Lys Ala Gly
65                  70                  75                  80

Thr Ser Ser Leu Thr Glu Cys Val Leu Asn Lys Ala Thr Asn Val Ala
                85                  90                  95

His Trp Thr Thr Pro Ser Leu Lys Cys Ile Arg Asp Pro Ala Leu Val
            100                 105                 110

His Gln Arg Pro Ala Pro Pro Ser Gly Gly Ser Gly Gly Gly Gly Ser
            115                 120                 125

Gly Gly Gly Ser Gly Gly Gly Gly Ser Leu Gln Asn Trp Val Asn Val
        130                 135                 140

Ile Ser Asp Leu Lys Lys Ile Gln Asp Leu Ile Gln Ser Met His Ile
145                 150                 155                 160

Asp Ala Thr Leu Tyr Thr Glu Ser Asp Val His Pro Ser Cys Lys Val
                165                 170                 175

Thr Ala Met Lys Cys Phe Leu Leu Glu Leu Gln Val Ile Ser Leu Glu
            180                 185                 190

Ser Gly Asp Ala Ser Ile His Asp Thr Val Glu Asn Leu Ile Ile Leu
            195                 200                 205

Ala Asn Asn Ser Leu Ser Ser Asn Gly Asn Val Thr Glu Ser Gly Cys
        210                 215                 220

Lys Glu Cys Glu Glu Leu Glu Glu Lys Asn Ile Lys Glu Phe Leu Gln
225                 230                 235                 240

Ser Phe Val His Ile Val Gln Met Phe Ile Asn Thr Ser
                245                 250

<210> SEQ ID NO 17
<211> LENGTH: 212
<212> TYPE: PRT
<213> ORGANISM: Artificial Sequence
<220> FEATURE:

<223> OTHER INFORMATION: Synthetic Construct

<400> SEQUENCE: 17

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Ser Gly
65                  70                  75                  80

Gly Ser Gly Gly Gly Gly Ser Gly Gly Gly Ser Gly Gly Gly Gly Ser
                85                  90                  95

Leu Gln Asn Trp Val Asn Val Ile Ser Asp Leu Lys Lys Ile Glu Asp
            100                 105                 110

Leu Ile Gln Ser Met His Ile Asp Ala Thr Leu Tyr Thr Glu Ser Asp
        115                 120                 125

Val His Pro Ser Cys Lys Val Thr Ala Met Lys Cys Phe Leu Leu Glu
    130                 135                 140

Leu Gln Val Ile Ser Leu Glu Ser Gly Asp Ala Ser Ile His Asp Thr
145                 150                 155                 160

Val Glu Asn Leu Ile Ile Leu Ala Asn Asn Ser Leu Ser Ser Ala Gly
                165                 170                 175

Asn Val Thr Glu Ser Gly Cys Lys Glu Cys Glu Glu Leu Glu Glu Lys
            180                 185                 190

Asn Ile Lys Glu Phe Leu Gln Ser Phe Val His Ile Val Gln Met Phe
        195                 200                 205

Ile Asn Thr Ser
    210
```

<210> SEQ ID NO 18
<211> LENGTH: 152
<212> TYPE: PRT
<213> ORGANISM: Homo sapiens

<400> SEQUENCE: 18

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
```

```
        130             135             140

Ile Leu Met Gly Thr Lys Glu His
145             150

<210> SEQ ID NO 19
<211> LENGTH: 126
<212> TYPE: PRT
<213> ORGANISM: Homo sapiens

<400> SEQUENCE: 19

Gln Gly Cys Pro Thr Leu Ala Gly Ile Leu Asp Ile Asn Phe Leu Ile
1               5                   10                  15

Asn Lys Met Gln Glu Asp Pro Ala Ser Lys Cys His Cys Ser Ala Asn
                20                  25                  30

Val Thr Ser Cys Leu Cys Leu Gly Ile Pro Ser Asp Asn Cys Thr Arg
            35                  40                  45

Pro Cys Phe Ser Glu Arg Leu Ser Gln Met Thr Asn Thr Thr Met Gln
        50                  55                  60

Thr Arg Tyr Pro Leu Ile Phe Ser Arg Val Lys Lys Ser Val Glu Val
65                  70                  75                  80

Leu Lys Asn Asn Lys Cys Pro Tyr Phe Ser Cys Glu Gln Pro Cys Asn
                85                  90                  95

Gln Thr Thr Ala Gly Asn Ala Leu Thr Phe Leu Lys Ser Leu Leu Glu
                100                 105                 110

Ile Phe Gln Lys Glu Lys Met Arg Gly Met Arg Gly Lys Ile
            115                 120                 125

<210> SEQ ID NO 20
<211> LENGTH: 133
<212> TYPE: PRT
<213> ORGANISM: Homo sapiens

<400> SEQUENCE: 20

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser
    130

<210> SEQ ID NO 21
<211> LENGTH: 161
<212> TYPE: PRT
<213> ORGANISM: Homo sapiens

<400> SEQUENCE: 21
```

```
Met Ser Pro Gly Gln Gly Thr Gln Ser Glu Asn Ser Cys Thr His Phe
1               5               10                  15

Pro Gly Asn Leu Pro Asn Met Leu Arg Asp Leu Arg Asp Ala Phe Ser
            20              25                  30

Arg Val Lys Thr Phe Phe Gln Met Lys Asp Gln Leu Asp Asn Leu Leu
        35              40                  45

Leu Lys Glu Ser Leu Leu Glu Asp Phe Lys Gly Tyr Leu Gly Cys Gln
        50              55                  60

Ala Leu Ser Glu Met Ile Gln Phe Tyr Leu Glu Glu Val Met Pro Gln
65              70                  75                  80

Ala Glu Asn Gln Asp Pro Asp Ile Lys Ala His Val Asn Ser Leu Gly
                85                  90                  95

Glu Asn Leu Lys Thr Leu Arg Leu Arg Leu Arg Arg Cys His Arg Phe
            100                 105                 110

Leu Pro Cys Glu Asn Lys Ser Lys Ala Val Glu Gln Val Lys Asn Ala
        115                 120                 125

Phe Asn Lys Leu Gln Glu Lys Gly Ile Tyr Lys Ala Met Ser Glu Phe
        130                 135                 140

Asp Ile Phe Ile Asn Tyr Ile Glu Ala Tyr Met Thr Met Lys Ile Arg
145                 150                 155                 160

Asn
```

SLOW-RELEASE CYTOKINE CONJUGATES

CROSS-REFERENCE TO RELATED APPLICATIONS

This application is a national stage application under 35 U.S.C. § 371 of International Application No. PCT/US2020/029911, filed internationally on Apr. 24, 2020, which claims priority to U.S. Provisional Application No. 62/839,112, filed on Apr. 26, 2019, the contents of which are incorporated herein by reference in their entirety.

INCORPORATION BY REFERENCE OF SEQUENCE LISTING

The present application is being filed along with a Sequence Listing in electronic format. The Sequence Listing is provided as a file entitled 670572002200SeqList.txt, created Oct. 21, 2021, which is 26,667 bytes in size. The information in the electronic format of the Sequence Listing is incorporated by reference in its entirety.

FIELD

This disclosure generally relates to releasable cytokine conjugates and methods of using the same.

BACKGROUND

Cytokines are small (up to ~20 kDa) proteins involved in cell signaling, and include the broad categories of interleukins (ILs), interferons (IFs), tumor necrosis factors (TNFs), chemokines, and lymphokines. They are produced by a broad range of cells, and are of particular importance in the immune system, regulating the balance between the humoral and cell-based immune responses. The interleukins comprise one group of cytokine that play particularly important roles in immunity. The majority of interleukins are expressed in helper CD4 T lymphocytes, and they promote the development and differentiation of T and B lymphocytes and hematopoietic cells.

Interleukin-2 (IL-2) (SEQ ID No: 1) is a ~16 kDa cytokine important in the natural response to microbial infection and the discrimination between native and foreign cells. IL-2 has essential roles in key functions of the immune system, tolerance and immunity, primarily via its direct effects on T cells. In the thymus, where T cells mature, it prevents autoimmune diseases by promoting the differentiation of certain immature T cells into regulatory T cells ($T_{reg}$), which suppress other T cells that are otherwise primed to attack normal healthy cells in the body. IL-2 enhances activation-induced cell death (AICD). IL-2 also promotes the differentiation of T cells into effector T cells ($T_{eff}$) and into memory T cells ($T_{mem}$) when the initial T cell is also stimulated by an antigen, thus helping the body fight off infections. Together with other polarizing cytokines, IL-2 stimulates naive CD4$^+$ T cell differentiation into Th1 and Th2 lymphocytes while it impedes differentiation into Th17 and folicular Th lymphocytes.

The IL-2 receptor (IL-2R) α subunit (CD25) binds IL-2 with low affinity ($K_d$~$10^{-8}$ M). Interaction of IL-2 and CD25 alone does not lead to signal transduction due to its short intracellular chain but has the ability (when bound to the β and γ subunit) to increase the IL-2R affinity 1000-fold. Heterodimerization of the β and γ subunits of IL-2R is essential for signaling in T cells. IL-2 can signal either via intermediate-affinity dimeric CD122/CD132 IL-2Rβγ receptor ($K_d$~$10^{-9}$ M) or high-affinity trimeric CD25/CD122/CD132 IL-2Rαβγ receptor ($K_d$~$10^{-11}$ M). Dimeric IL-2Rβγ is expressed by CD8$^+$ $T_{mem}$ cells and NK cells, whereas $T_{reg}$ and activated T cells express high levels of trimeric IL-2Rαβγ. The γ subunit (CD132) is shared between the receptors for IL-2, IL-4, IL-7, IL-9, IL-13, IL-15, and IL-21.

Regulatory T cells ($T_{reg}$) are a subset of T lymphocytes that are crucial for maintenance of self-tolerance. While IL-2 is involved in the activation of both regulatory and effector ($T_{eff}$) cells, the greater expression of the high-affinity receptor in $T_{reg}$ over $T_{eff}$ cells means that low doses of IL-2 preferentially support maintenance of $T_{reg}$ cells. Autoimmune responses in diseases such as type 1 diabetes, multiple sclerosis, Crohn's disease, and systemic lupus erythematosus correlate with $T_{reg}$ deficiencies. The selective, long-lasting stimulation of $T_{reg}$ cells via the high-affinity receptor would thus hold promise for the treatment of autoimmune diseases.

High-dose IL-2 therapy with Aldesleukin (recombinant IL-2) has been approved for treatment of metastatic melanoma and renal cell carcinoma. However, there is a low objective response rate and a high incidence of end-organ toxicity with high-dose therapy. It is believed that most anti-tumor activity of IL-2 results from stimulation of T cells via the high-affinity IL-2Rαβγ receptor, and that most of the toxicity is due to release of inflammatory proteins by natural killer cells via the low-affinity IL-2Rβγ receptor. An IL-2 mutein having an arginine replacing asparagine at position 88 (SEQ ID No: 2; IL2-N88R, BAY 50-4798) selectively binds the high-affinity IL-2Rαβγ receptor, resulting in a 3,000-fold increase in selectivity for activation of $T_{reg}$ cells over $T_{eff}$ and NK cells. In agreement with this idea, rodent models showed equivalent efficacy of BAY 50-4798 and Aldesleukin but lower toxicity with the mutein. A human Phase 1 trial of BAY 50-4798 confirmed the expected differential activation of $T_{reg}$ cells over $T_{eff}$ and NK cells, yet the anti-tumor response was limited and development of the mutein was stopped.

Attempts to extend the in vivo half-life of IL-2 and analogs and thereby improve their efficacy have been reported. Various fusions of IL-2 with antibodies and antibody fragments (WO2014/023752 A1) have been disclosed. Several workers have disclosed Fc or IgG fusions with IL-2 {Bell, 2015 #2} or $T_{regs}$-specific muteins, such as Fc-IL-2N88R (Greve, J. US 2017/0204154 A1) or IgG-IL-2N88D {Peterson, 2018 #1}. The IgG-IL-2N88D has a half-life of only ~8 hr when injected IV, or 14 hr when injected SC, in cynomolgous monkeys, much less than the expected 14 days for an IgG, and the short $t_{1/2}$ was attributed to receptor-mediated endocytosis (RME). Regardless, one SC injection of the IgG-IL-2N88ND gave prolonged increases of regulatory T cells comparable to daily injections of low-dose IL-2. That is, after one injection, $T_{regs}$ expanded to a maximum at ~4 days and lasted ~14 days. There was a 10- to 14-fold increase in CD4+ and CD8+CD25+FOXP3+ $T_{regs}$, but no effect on CD4+ or CD8+ memory effector T cells. Such fusion proteins suffer several deficiencies, however, such as loss of potency and increased immunogenicity over the native proteins. Certain permanent and releasable conjugates of IL-2 with water-soluble polymers have been disclosed (U.S. Pat. No. 9,861,705). IL-2 muteins containing unnatural amino acids to alter the selectivity between receptors and water-soluble conjugates thereof have been disclosed (WO2019/028425; WO2019/028419).

Interleukin-15 is a related cytokine that acts through a unique receptor α-chain but the same β and γ receptor chains as IL-2. IL-15 is a pleiotropic cytokine important for both adaptive and innate immunity. IL-15 promotes the activation and maintenance of natural killer (NK) and CD8+ effector $T_{mem}$ cells, and is of interest as an immunotherapeutic agent for the treatment of cancers and immuodeficiencies. Exogenous IL-15 has been shown to stimulate proliferation of CD8+ $T_{mem}$ cells both in vivo and in vitro. Low-dose therapy with IL-15 is hypothesized to promote the maintenance and function of tumor-specific CD8+ $T_{mem}$ cells and thus delay or prevent tumor relapse in failed adoptive immunotherapy (Roychowdhury et al., Cancer Research 64: 8062-7 (2004)). Low-dose therapy by continuous infusion to monkeys over 10 days resulted in a 100–x expansion of CD8+ effector $T_{mem}$ cells in the peripheral blood, which was more effective than a daily bolus dosing regimen (Sneller et al., Blood 118: 6845-8 (2011)). Stabilized muteins of IL-15 have been reported (Nellis et al., Pharm. Res. 29: 722-38 (2012)). Certain permanent and releasable conjugates of IL-15 with water-soluble polymers have been disclosed (PCT Publication WO2015/153753A2). Muteins of IL-15 showing improved receptor agonism have been disclosed (Zhu et al., J. Immunology 2009, 183(6): 3598). IL-15[N72D] showed a 4-5 fold increase in biological activity over native IL-15 in cell proliferation assays. IL-15 receptor agonists comprising IL-15 and the sushi domain of the IL-15Rα (IL-15RαSu) have also been reported, both as complexes and as fusion proteins (Han et al., Cytokine 2011, 56(3):804-10; Mortier et al., J. Biological Chem. 2006, 281: 1612-9; U.S. Pat. No. 10,358,477). A multimeric complex of IL-15[N72D] and IL-15RαSuFc fused to the Fc domain of IgG1 (ALT-803) is currently in clinical trials.

Muteins of IL-2 having reduced affinity for the trimeric receptor have been disclosed (U.S. Pat. No. 9,206,243). These muteins show reduced ability to stimulate $T_{reg}$ cells while maintaining the ability to stimulate CD4+T helper cells, CD8+ T cells, and natural killer (NK) cells. It is proposed that such IL-2 muteins may show enhanced anti-tumor activity due to the lack of immune suppression by $T_{reg}$ cells.

IL-7 is a cytokine required for T cell development and survival and homeostasis of mature T cells. The transition of double negative (DN) CD4− CD8− thymocyte progenitor cells in the thymus requires IL-7 signaling, although at high doses IL-7 blocks DN progression. Once in the periphery, survival of naïve T cells is dependent upon IL-7. The IL-7 receptor comprises a specific α-chain (CD127) that is expressed almost exclusively on lymphoid cells together with the common γ-chain (CD132) used for IL-2, IL-15, IL-9, and IL-21. IL-7 has been in clinical trials as an immunotherapeutic agent for cancer patients who have undergone T cell-depleting therapies in an attempt to increase levels of CD4+ and CD8+ T cells. Administration of IL-7 resulted in preferential expansion of naïve T cells, giving a broader repertoire of T cells regardless of patient age, suggesting potential therapy with IL-7 to enhance the immune response in patients with low naïve T cell populations (ElKassar & Gress, J. Immunotoxicol. (2010) 7: 1-7.)

IL-9 is another pleiotropic cytokine structurally related to IL-2 and IL-15 produced by mast cells, NK cells, TH2, TH17, $T_{reg}$, ILC2, and Th9 cells, with Th9 cells being regarded as the major CD4+ T cell producers. The IL-9 receptor comprises a specific alpha-chain (CD129) together with the common γ-chain (CD132). Low-dose therapy using IL-9 has been proposed to prevent chemotherapy-induced thrombocytopenia and accelerate platelet recovery (Xiao et al., Blood 129: 3196-3209 (2017)).

IL-10 (human cytokine synthesis inhibitory factor) is an anti-inflammatory, immunosuppressive cytokine produced by Th2 cells, B cells, and macrophages. It inhibits the synthesis of several cytokines produced by Th1 cells, including gamma-interferon, IL-2, and tumor necrosis factor-alpha (TNF-α), and inhibits production of IL-1, IL-6, IL-8, granulocyte colony-stimulating factor (G-CSF), and TNF-α by monocytes and macrophages. IL-10 appears to induce NK-cell activation and target-cell destruction in a dose-dependent manner (Zheng et al. J. Exp. Med. 184:579-84 (1996)). It is under investigation for treatment of autoimmune diseases, septic shock, and bacterial sepsis. PEGylated derivatives of IL-10 have been disclosed (PCT Publication WO2010/077853). PEGylated-IL10 has been shown to induce interferon gamma and CD8+ T-cell dependent anti-tumor immunity (Emmerich et al., Cancer Res. 72: 3570-81 (2012); Mumm et al., Cancer Cell 20:781-96 (2011); Chan et al., J Interferon Cytokine Res. 35: 948-55 (2015)). Investigation of PEGylated-IL10 suggests that in human therapy, IL-10 is predominantly immunostimulatory through activation of CD8+ T cells, and while a Phase 3 trial for treatment of metastatic stage 4 pancreatic cancer failed to meet the primary endpoint, a Phase 2 trial in non-small cell lung cancer is underway.

IL-21 is expressed in activated CD4+ T cells, and is up-regulated in Th2 and Th17 T helper cells and T follicular cells. It is expressed in and regulates the functions of NK cells. The IL-21 receptor (IL21R) is expressed on the surface of T, B, and NK cells and functions in combination with the common γ-chain (CD132). Roles for IL-21 in the treatment of allergies, viral infections, and cancer have been proposed, and it has been in clinical trials for treatment of metastatic melanoma and renal cell carcinoma. IL-21 has been reported to improve the HIV-specific cytotoxic T cell response and NK cell functions in HIV-infected subjects, suggesting potential for use in the treatment of HIV.

Continuous infusion shows the promise of low, continuous-dose therapy with cytokines, yet it is difficult to implement practically in human therapy. There thus exists a need for improved agents to enable low-dose, extended duration therapies for various diseases including cancers and autoimmune disorders using cytokines.

BRIEF SUMMARY

In one aspect, provided is a linker-drug of formula (I):

$$Z\text{-}L\text{-}D \tag{I},$$

wherein Z, L, D are as detailed herein.

In some embodiments, the linker-drug Z-L-D is a compound of formula (Ia):

wherein Z, S, n, $R^1$, $R^2$, $R^4$, Y, and D are as detailed herein.

In another aspect, provided is a linker of formula (IIa):

$$Z-S-(CH_2)_n-\overset{\overset{\displaystyle R^4}{|}}{\underset{\underset{\displaystyle R^4}{|}}{C}}-\overset{\overset{\displaystyle HC-R^2}{|}}{\underset{\underset{\displaystyle H}{|}}{C}}-O-\overset{\overset{\displaystyle O}{||}}{C}-X,$$ (IIa)

wherein n, Z, S, $R^1$, $R^2$, $R^4$ and X are as detailed herein.

In another aspect, provided is a conjugate of formula (III):

$$M-[Z^*-L-D]_q$$ (III), wherein M, $Z^*$, L, D, and q are as detailed herein.

In another aspect, provided is degradable crosslinked hydrogel of formula (IV):

$$P^1-\left[A^*-(CH_2)_n-\overset{\overset{\displaystyle R^{14}}{|}}{\underset{\underset{\displaystyle R^{14}}{|}}{C}}-\overset{\overset{\displaystyle HC-R^{12}}{|}}{\underset{\underset{\displaystyle H}{|}}{C}}-O-\overset{\overset{\displaystyle O}{||}}{C}-\overset{\overset{\displaystyle H}{|}}{N}-(CH_2)_x-\overset{\overset{\displaystyle (CH_2)_yB}{|}}{\underset{\underset{\displaystyle H}{|}}{C}}-(CH_2)_z-C^*\right]_r-P^2,$$ (IV)

wherein $P^1$, $P^2$, r, $A^*$, B, $C^*$, n, $R^{11}$, $R^{12}$, $R^{14}$, x, y, and z are as detailed herein.

In another aspect, provided are methods for preparing the compounds disclosed herein and methods for their use. In another aspect, provided are pharmaceutical compositions containing a conjugate of formula (III) or a hydrogel of formula (IV).

BRIEF DESCRIPTION OF THE DRAWINGS

FIG. 4A shows the release of IL-2[N88R,C125] from the random acylation conjugate administered at 0.25 μmol/kg, and FIG. 4B shows the release of AP-IL-2 [N88R,C125S] from the reduction alkylation conjugate administered at 0.12 μmol/kg.

FIG. 7A: BALB/c mice (n=6) were given a single s.c. injection containing either 28 nmol (19 mg/kg) or 9.9 nmol (6.5 mg/kg) microsphere-IL-2[N88R,C125S] in the flank. A $t_{1/2}$ of 31 h was determined. FIG. 7B: NOD mice (n=6) were dosed with microsphere-IL-2[N88R,C125S](0.5, 1, 5, 10 or 19 mg/kg) in the flank. A $t_1 12$ of 18 h was determined. FIG. 7C: NSG mice (n=6) or NOD mice (n=6) were dosed with microsphere-IL-2[N88R,C125S] (5 mg/kg) in the flank A $t_{1/2}$ of 152 h was determined [aminopropyl]-IL2[N88R,C125S] in NSG mice. In all cases, plasma was analyzed using Thermofisher ELISA to quantify IL-2[N88R,C125S] concentration.

Figure 8:
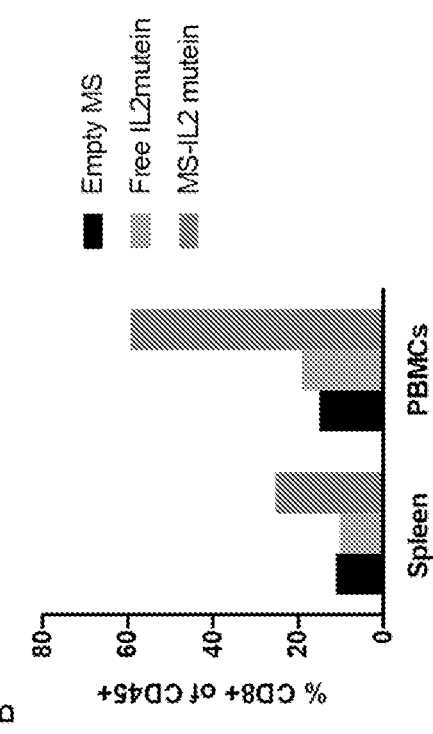
Figure 8:
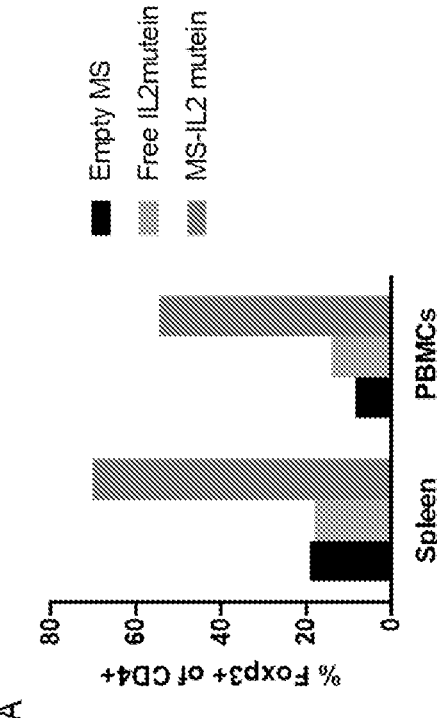

FIG. 8 shows the effect of IL-2[N88R,C125S] ("IL-2 mutein") on the expansion of Foxp3+CD4+ and CD8+ cell populations. FIG. 8A shows the expansion of Foxp3+CD4+ T-cells in the spleen and peripheral blood mononuclear cells (PBMCs). FIG. 8B shows the expansion of CD8+ T-cells in the spleen and PBMCs. The percentage CD8+ cells found in the spleen and PBMCs were approximately 11% and 19% respectively. These percentages increased to approximately 25% and 60% respectively, when treated with the microsphere-IL-2[N88R,C125S]. NOD mice were administered IL2-mutein (QDx5, 25,000 units), a single injection of empty microspheres or microsphere-IL-2[N88R,C125S] (18 mg/kg). Mice were sacrificed 2 hours after the last dose on day 5.

Figure 9:
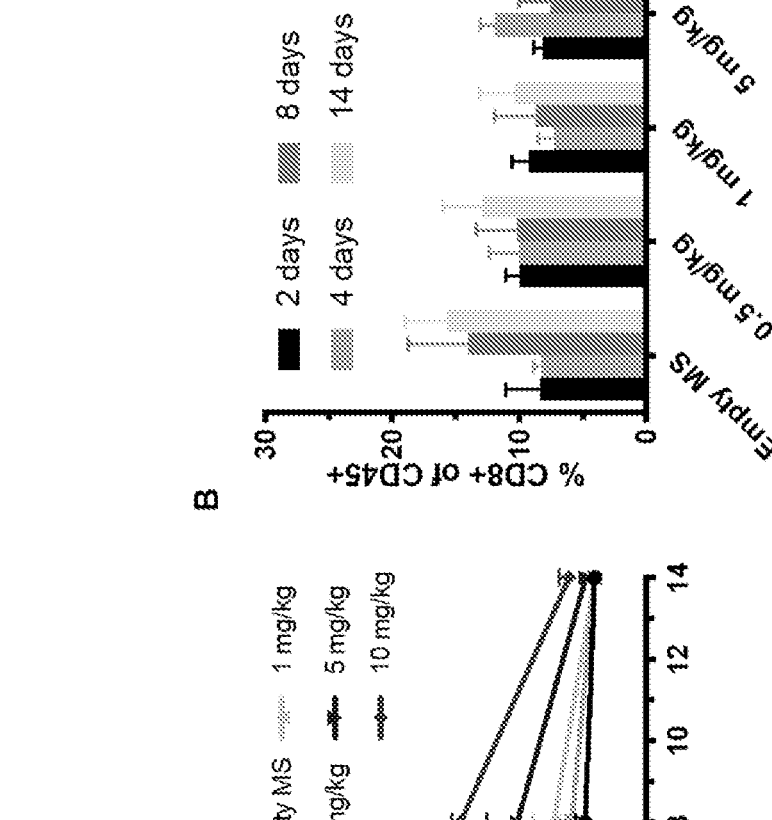

FIG. 9 shows the dose dependent Foxp3+CD4+ Tcell expansion in PBMCs. FIG. 9A shows the effect of microsphere-IL-2[N88R,C125S] on the expansion of Foxp3+ CD4+ T-cells, and FIG. 9B shows their effect on the activation of CD8+ cells (right) in NOD mice (n=3/dose group). Microsphere-IL-2[N88R,C125S] preferentially expands Foxp3+CD4+ T-cells, and avoids activation of CD8+ cells in NOD mice (n=3/dose group). Foxp3+CD4+ T-cell expansion peaks at 4 days for all doses and returns to baseline levels by day 14.

Figure 10:
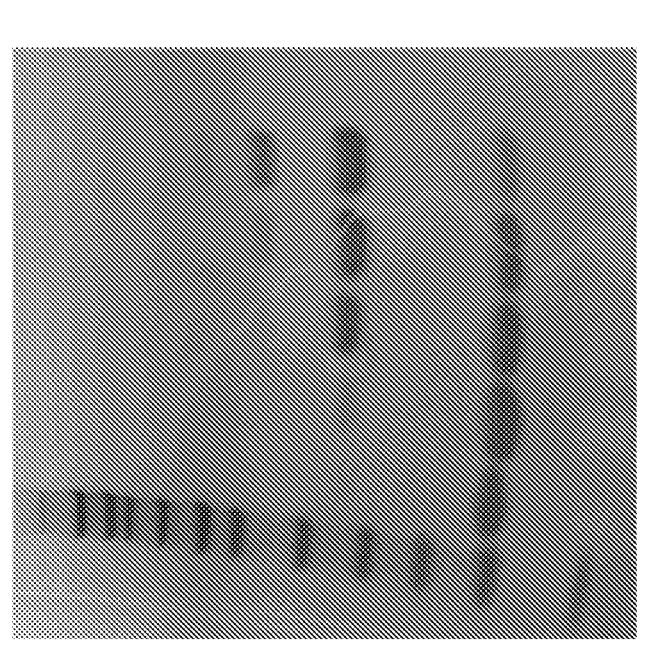

FIG. 10 shows an SDS-PAGE gel with bands corresponding to linker-protein products from reductive alkylation of IL-15. From left to right: molecular weight markers; IL-15; IL-15+PEG$_{5\ kDa}$-DBCO; IL-15+1 Eq (IIb)+PEG$_{5\ kDa}$-DBCO; IL-15+3 Eq (IIb)+PEG$_{5\ kDa}$-DBCO; and IL-15+5 Eq (IIb)+PEG$_{5\ kDa}$-DBCO.

Figure 11:
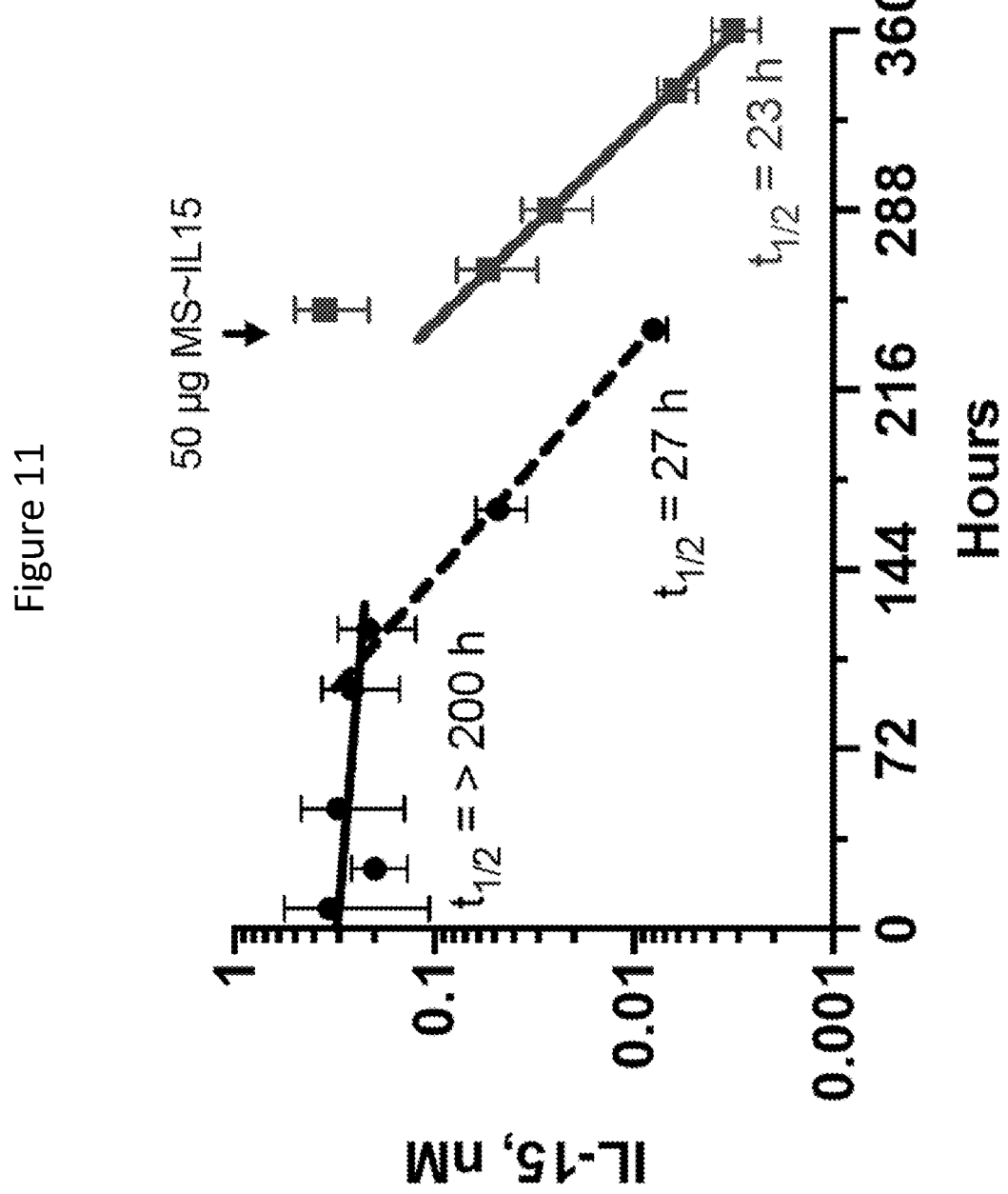

FIG. 11 shows the pharmacokinetics of [aminopropyl]-IL-15 released from MS-IL-15 in C57BL/6J mice. Normal, male C57BL/6J mice were dosed with MS-IL-15 (50 μg) at t=0 h and t=240 h. Plasma samples were prepared and analyzed using the human IL-15 Quantikine ELISA (R&D systems). Two distinct $t_{1/2}$ were observed through 240 h. A $t_{1/2}>200$ hours was observed through 120 hours followed by a second $t_{1/2}$ of 27 h from 120 h to 240 h. A second injection of MS-IL15 (50 μg) was administered immediately after the 240 h blood draw (blue data). A $t_{1/2}$ of 23 h was observed from 264 h to 360 h.

Figure 12:
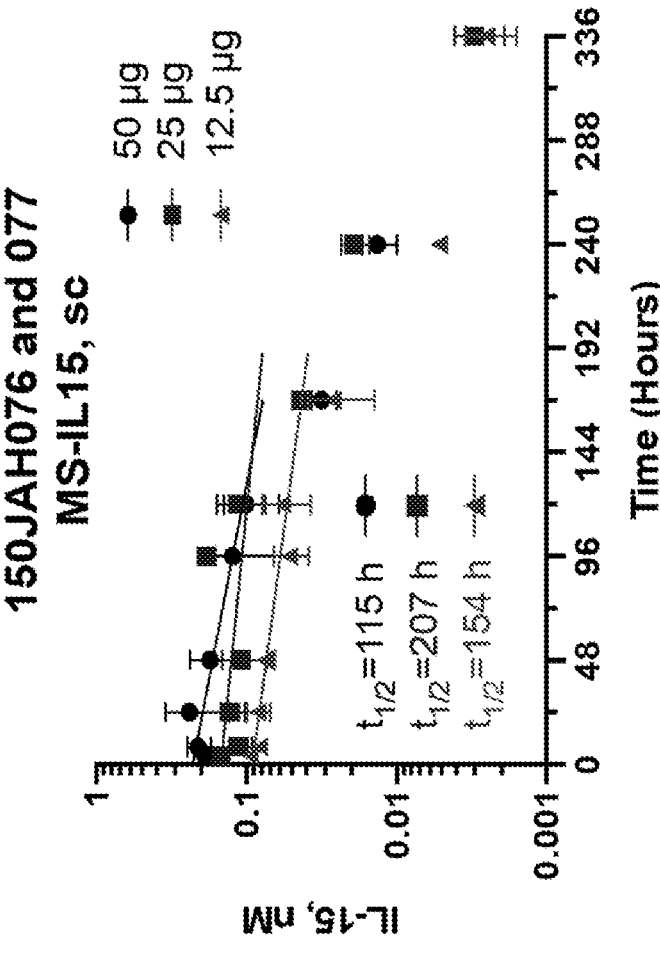

FIG. 12 shows the dose-dependence of pharmacokinetics of [aminopropyl]-IL-15 released from microsphere-IL-15 in C57BL/6J mice. Normal, male C57BL/6J mice were dosed with MS-IL-15 (12.5, 25 or 50 μg). Plasma samples were prepared and analyzed using the human IL-15 Quantikine ELISA (R&D systems). A $t_{1/2}$ of 115 207 hours was observed for data fit through 120 hours.

Figure 13:
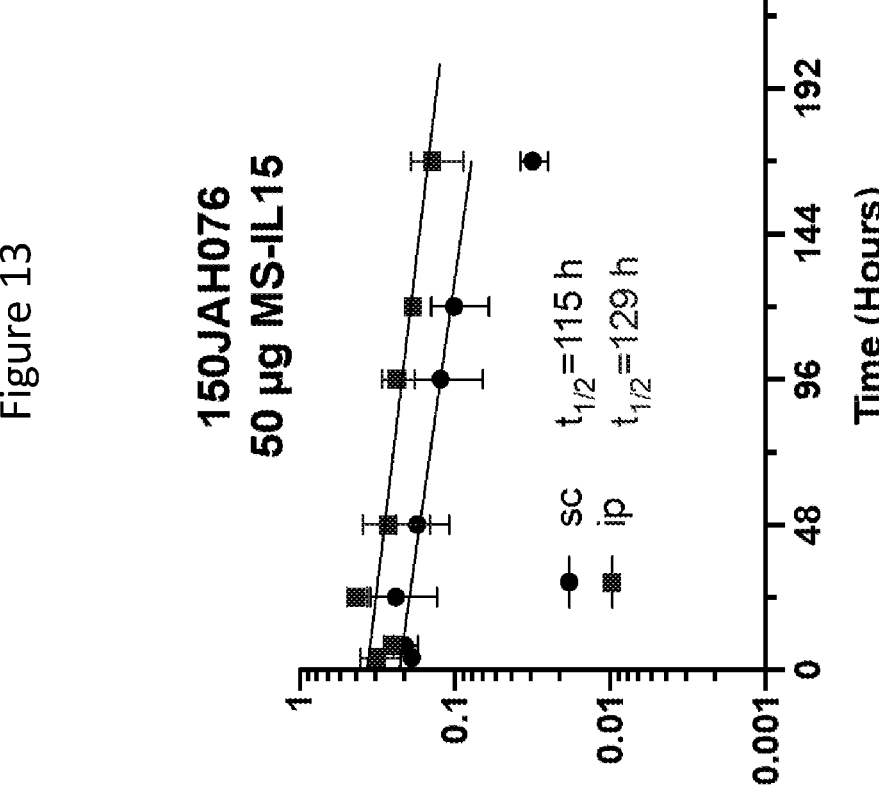

FIG. 13 shows the pharmacodynamics of [aminopropyl]-IL-15 released from microsphere-IL-15 in C57BL/6J mice administered s.c. vs i.p. Normal, male C57BL/6J mice were administered MS-IL-15 (50 μg) either s.c. injection (black, ●) or i.p. injection (blue, ●). Plasma samples were prepared and analyzed using the human IL-15 Quantikine ELISA (R&D systems). A similar tin was observed for s.c. (115 h) and i.p. (129 h) administration through 120 h.

Figure 14:
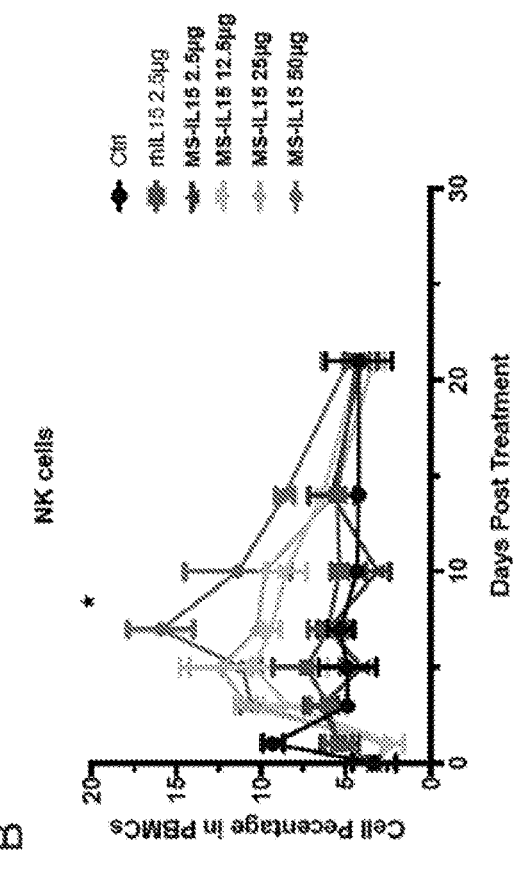
Figure 14:
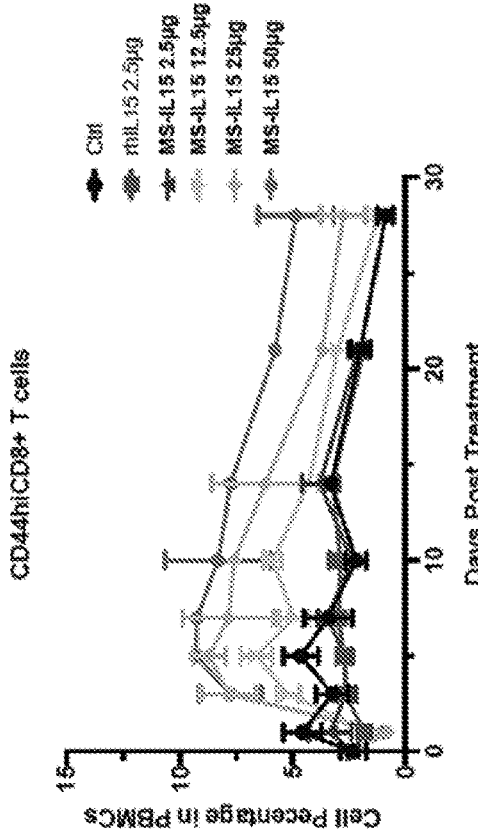

FIG. 14 shows the effect of microsphere-IL15 conjugate on NK cells and CD44hiCD8$^+$ Tcells. Microsphere-IL15 conjugate expands CD44$^{hi}$CD8$^+$ T cells and NK cells. FIG. 14A: Expansion of CD44hiCD8$^+$ T cells. FIG. 14B: Expansion of NK cells. Normal, male C57BL/6J mice were administered a single s.c injection microsphere~IL-15 (2.5, 12.5, 25 or 50 μg of IL-15), empty microspheres (black) or a single s.c. injection of rhIL15 (2.5 μg). Flow cytometry was used to monitor the expansion of NK cells and CD44hiCD8$^+$ T cells in PBMCs. Expansion of CD44hiCD8$^+$ T cells continued for 28 days after a single 50 ug injection of microsphere-IL15.

Figure 15:
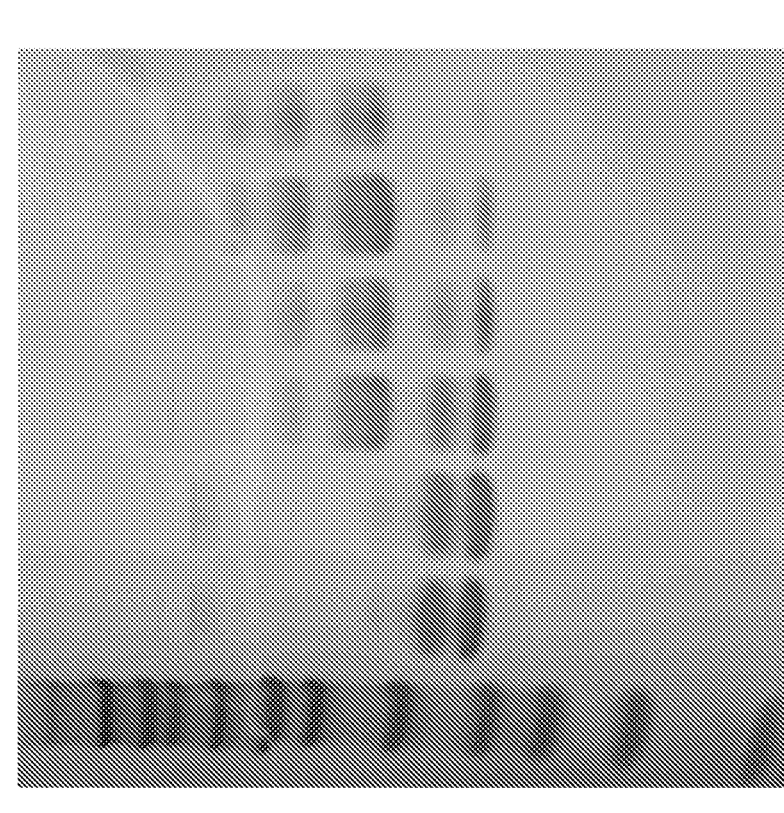

FIG. 15 shows an SDS-PAGE gel with bands corresponding to linker-protein products from reductive alkylation of receptor-linked interleukin (RLI) with linker (IIb), visualized after gel-shift reaction with PEG$_{5\ kDa}$-DBCO. From left to right: molecular weight markers; RLI; RLI+PEG$_{5\ kDa}$-DBCO; RLI+1.5 Eq (IIb)+PEG$_{5\ kDa}$-DBCO; RLI+2 Eq (IIb)+PEG$_{5\ kDa}$-DBCO; RLI+3 Eq (IIb)+PEG$_{5\ kDa}$-DBCO; and RLI+5 Eq (IIb)+PEG$_{5\ kDa}$-DBCO.

Figure 16:
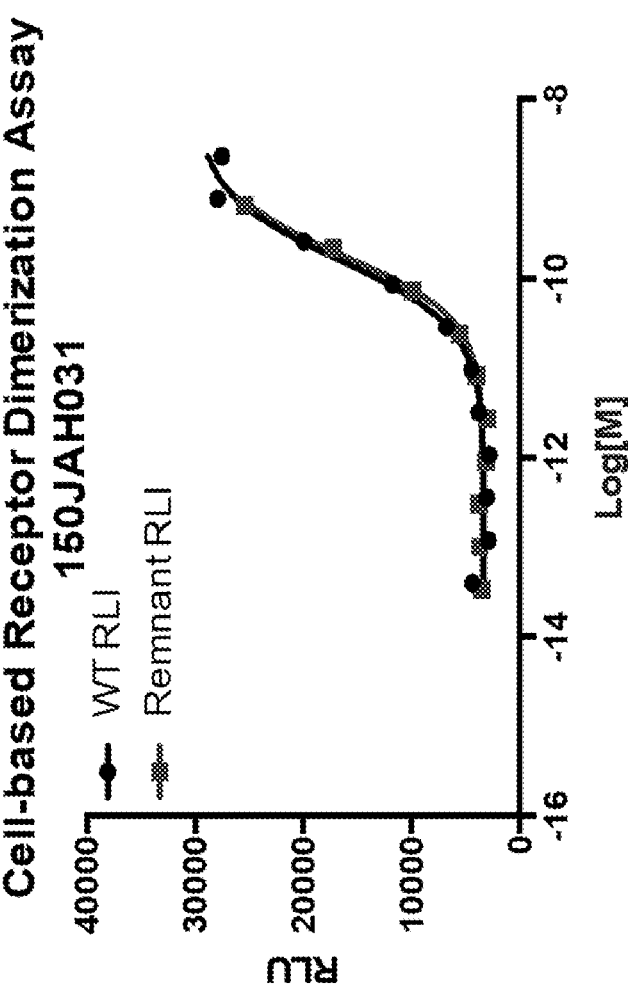

FIG. 16 shows the results of an IL-2Rβγ receptor-binding cell-based assay for RLI. A U2OS cell-based assay was used to determine the binding activity of [aminopropyl]-RLI released from the conjugate at pH 7.4 (EC$_{50}$=180 μM) compared to that of native RLI (EC$_{50}$=160 μM).

Figure 17:
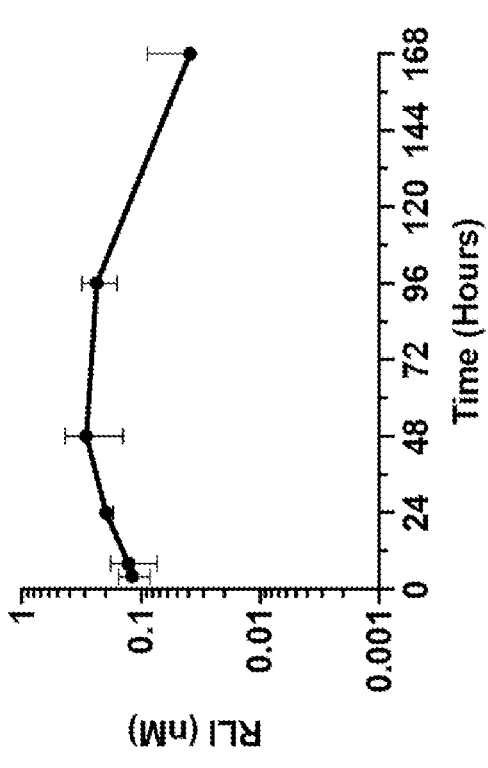

FIG. 17 shows the pharmacokinetics of [aminopropyl]-RLI released from microsphere conjugate in C57BL/6J mice. Normal, male C57BL/6J mice were dosed with microsphere-RLI conjugate (1.5 nmol). Plasma samples were prepared and analyzed using R&D systems DuoSet hIL15/IL15Rα complex ELISA (DY6924).

Figure 18:
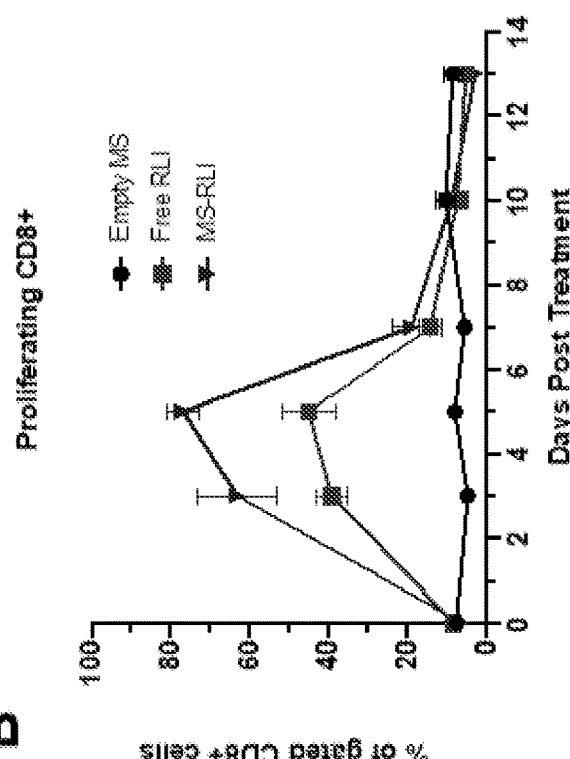
Figure 18:
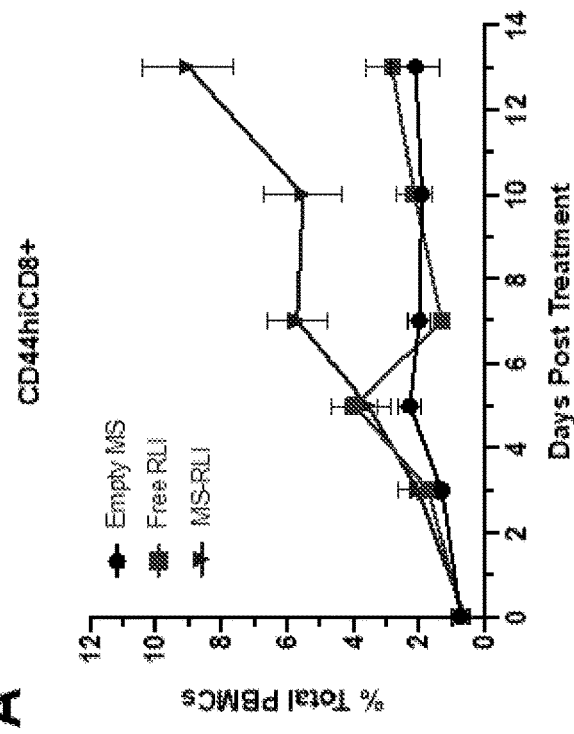

FIG. 18 shows the pharmacodynamics of [aminopropyl]-RLI released from a microsphere conjugate, measuring the expansion of CD8$^+$ memory T cells in PBMCs. FIG. 18A: Cell percentage of CD8$^+$ memory T cells in PBMCs and FIG. 18B: Proliferation of CD8$^+$ T cells. Normal, male C57BL/6J mice were administered empty MS, MS-RLI (34 μg, 1.5 nmol), or native RLI (2.5 μg, 0.11 nmol QDx4) via s.c. injection on the flank. PBMCs were prepared following blood draws and stained for flow cytometry analysis.

Figure 19:
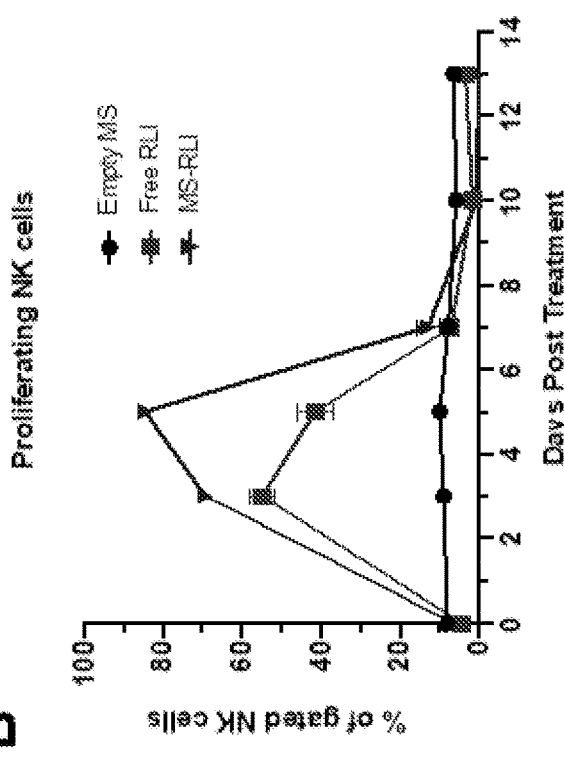
Figure 19:
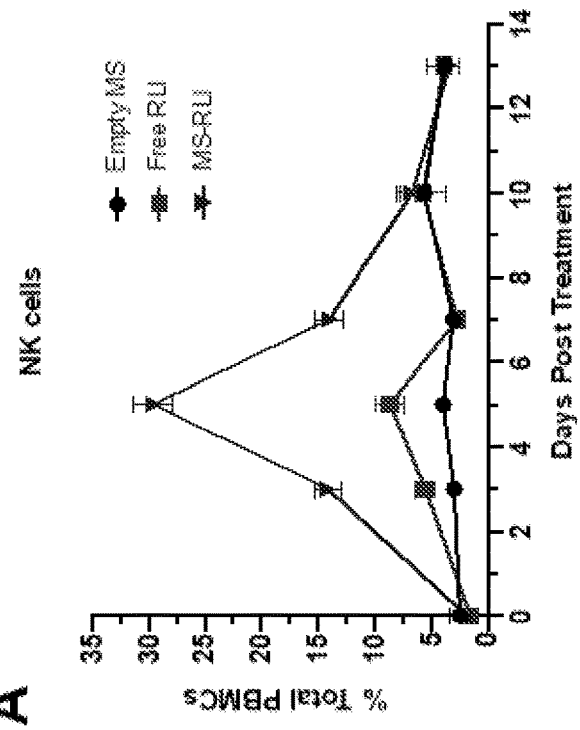

FIG. 19 shows the expansion of NK cells in PBMCs upon treatment with microsphere-RLI. FIG. 19A: Cell percentage of NK cells in PBMCs and FIG. 19B: Proliferation of NK cells. Normal, male C57BL/6J mice were administered empty MS, MS-RLI (34 μg, 1.5 nmol), or native RLI (2.5 μg, 0.11 nmol QDx4) via s.c. injection on the flank. PBMCs were prepared following blood draws and stained for analysis via flow cytometry.

DETAILED DESCRIPTION

The present disclosure provides releasable conjugates of cytokine proteins including variants thereof. The conjugates deliver these protein therapeutics at low, sustained doses over extended periods, and thus are useful for the treatment of various diseases.

In one aspect, the disclosure provides cytokines and variants thereof having an attached releasable linker suitable for conjugation of the proteins to macromolecular carriers. These linkers control the rate of release of the proteins from the carrier, thus determining the concentration and duration of the cytokine or variant in the body.

In another aspect, the disclosure provides conjugates that release cytokines and variants thereof from macromolecular carriers. The carriers are either soluble or insoluble depots that extend the duration of proteins in the body.

In another aspect, the disclosure provides methods of preparation and use for the linker-cytokines and conjugates of the disclosure.

Definitions

For use herein, unless clearly indicated otherwise, use of the terms "a", "an" and the like refers to one or more.

As used herein, and unless otherwise specified, the term "about" or "approximately," when used in connection with a value, contemplates a value within 15%, within 10%, within 5%, within 4%, within 3%, within 2%, within 1%, or within 0.5% of the value.

The term "alkyl" includes linear, branched, or cyclic saturated hydrocarbon groups of 1-20, 1-12, 1-8, 1-6, or 1-4 carbon atoms. In some embodiment, an alkyl is linear or branched. Examples of linear or branched alkyl groups include, without limitation, methyl, ethyl, n-propyl, isopropyl, n-butyl, t-butyl, isobutyl, sec-butyl, n-pentyl, n-hexyl, n-heptyl, n-octyl, n-nonyl, n-decyl, and the like. In some embodiments, an alkyl is cyclic. Examples of cyclic alkyl groups include, without limitation, cyclopropyl, cyclobutyl, cyclopentyl, cyclopentadienyl, cyclohexyl, and the like.

The term "alkoxy" includes alkyl groups bonded to oxygen, including methoxy, ethoxy, isopropoxy, cyclopropoxy, cyclobutoxy, and the like.

The term "alkenyl" includes non-aromatic unsaturated hydrocarbons with carbon-carbon double bonds and 2-20, 2-12, 2-8, 2-6, or 2-4 carbon atoms.

The term "alkynyl" includes non-aromatic unsaturated hydrocarbons with carbon-carbon triple bonds and 2-20, 2-12, 2-8, 2-6, or 2-4 carbon atoms.

The term "aryl" includes aromatic hydrocarbon groups of 6-18 carbons, preferably 6-10 carbons, including groups such as phenyl, naphthyl, and anthracenyl. The term "heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and the like.

In some instances, alkenyl, alkynyl, aryl or heteroaryl moieties may be coupled to the remainder of the molecule through an alkyl linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" or "halo" includes bromo, fluoro, chloro and iodo.

The term "heterocyclic ring" or "heterocyclyl" refers to a 3-15 membered aromatic or non-aromatic ring comprising at least one N, O, or S atom. Examples include, without limitation, piperidinyl, piperazinyl, tetrahydropyranyl, pyrrolidine, and tetrahydrofuranyl, as well as the exemplary groups provided for the term "heteroaryl" above. In some embodiments, a heterocyclic ring or heterocyclyl is non-aromatic. In some embodiments, a heterocyclic ring or heterocyclyl is aromatic.

The term "macromolecule" refers to a molecule or residue of a molecule having a molecular weight between 5,000 and 1,000,000 Daltons, preferably between 10,000 and 500,000 Daltons, and more preferably between 10,000 and 250,000 Daltons. Examples of macromolecules include, without limitation, proteins including antibodies, antibody fragments, and enzymes; polypeptides including poly(amino acid)s such as poly(lysine) and poly(valine) and mixed-sequence polypeptides; synthetic polymers including poly (ethylene glycol) (PEG), poly(ethylene oxide) (PEO), poly (ethylene imine) (PEI), and co-polymers thereof; and polysaccharides such as dextrans. In some embodiments, the macromolecules comprise at least one functional group suitable for conjugation, either natively or after chemical transformation, such as an amine, carboxylic acid, alcohol, thiol, alkyne, azide, or maleimide group as described above. In certain embodiments of the disclosure, the macromolecule is a polyethylene glycol. The polyethylene glycol may be linear or branched, with one end terminated with a functional group suitable for conjugation and the other end or ends terminated by a capping group (for example, methyl), or may comprise multiple arms each arm terminating in a functional group suitable for conjugation. In preferred embodiments of the disclosure, the polyethylene glycol is a linear, branched, or multiple-arm polymer having an average molecular weight between 20,000 and 200,000 Daltons, preferably between 20,000 and 100,000 Daltons, and most preferably approximately 40,000 Daltons. Examples of such polyethylene glycols are known in the art and are commercially available, for example from NOF Corporation (Tokyo, Japan).

"Optionally substituted" unless otherwise specified means that a group may be unsubstituted or substituted by one or more (e.g., 1, 2, 3, 4 or 5) of the substituents which may be same or different. Examples of substituents include, without limitation, alkyl, alkenyl, alkynyl, halogen, —CN, —OR—, —SR$^{aa}$, —NR—R$^{bb}$, —NO$_2$, —C═NH(OR$^{aa}$), —C(O) R$^{aa}$, —OC(O)R$^a$, —C(O)OR$^{aa}$, —C(O)NR$^{aa}$R$^{bb}$, —OC(O) NR$^{aa}$R$^{bb}$, —NR—C(O)R$^{bb}$, —NR$^{aa}$C(O)OR$^{bb}$, —S(O)R$^{aa}$, —S(O)$_2$R$^{aa}$, —NR$^{aa}$S(O)R$^{bb}$, —C(O)NR—S(O)R$^{bb}$, —NR$^{aa}$S(O)$_2$R$^{bb}$, —C(O)NR$^{aa}$S(O)$_2$R$^{bb}$, —S(O)NR$^{aa}$R$^{bb}$, —S(O)$_2$NR—R$^{bb}$, —P(O)(OR$^{aa}$) (OR$^{bb}$), heterocyclyl, heteroaryl, or aryl, wherein the alkyl, alkenyl, alkynyl, cycloalkyl, heterocyclyl, heteroaryl, and aryl are each independently optionally substituted by R$^{cc}$, wherein R$^{aa}$ and R$^{bb}$ are each independently H, alkyl, alkenyl, alkynyl, heterocyclyl, heteroaryl, or aryl, or R$^{aa}$ and R$^{bb}$ are taken together with the nitrogen atom to which they attach to form a heterocyclyl, which is optionally substituted by alkyl, alkenyl, alkynyl, halogen, hydroxyl, alkoxy, or —CN, and wherein:

each R$^{cc}$ is independently alkyl, alkenyl, alkynyl, halogen, heterocyclyl, heteroaryl, aryl, —CN, or —NO$_2$.

While typically, the active form of the drug is directly released from the conjugates of the disclosure, in some cases, it is possible to release the active drug in the form of a prodrug thereof.

Linker-Drug

In one aspect, provided is a linker-drug of formula (I):

Z-L-D             (I), wherein Z is a functionality that allows for connection of the linker-drug to a macromolecular carrier, L is a cleavable linker, and D is a cytokine or cytokine variant. In some embodiments, the releasable linker is suitable for conjugation of the proteins to macromolecular carriers. In some embodiments, the linker controls the rate of release of the cytokine or variant from the carrier, thus determining the concentration and duration of active protein in the body. In one aspect, provided is a linker-drug of formula (I):

Z-L-D             (I), wherein Z is a functionality that allows for connection of the linker-drug to a macromolecular carrier, L is a cleavable linker, and D is a cytokine or cytokine variant.

In some embodiments of a linker-drug of formula (I), the cytokine D is IL-2, IL-4, IL-7, IL-9, IL-10, IL-15, IL-21, or a cytokine variant thereof. D also encompasses a cytokine with certain chemical modifications to the cytokine, such as NH(CH$_2$CH$_2$O)$_p$(CH$_2$)$_m$, wherein m is a integer from 2 to 6 and p is an integer from 0 to 1000, attached to an amine group resulting from reductive amination to attach the linker L. In certain embodiments, this modification is attached to the N-terminal alpha-amino group of the protein sequence.

By "cytokine variant" is meant a protein of altered sequence ("mutein") having at least 99%, 98%, 97%, 96%, 95%, 94%, 93%, 92%, 91%, or 90% sequence identity to the native cytokine. In some embodiments, the cytokine variant has at least 90% sequence identity to the native cytokine. In some embodiments, the cytokine variant comprises between 1 and 10 altered amino acids from the native sequence, and is selected based on improvements in protein stability and/or receptor binding affinity or selectivity. Depending on the expression system used to produce recombinant cytokines, the sequence may or may not include the initiating methionine residue. For example, IL-2 variants useful in the disclosure may be selected from those having increased binding affinity for the trimeric αβγ-receptor over the dimeric βγ receptor. In some embodiments, the IL-2 variant has a mutation at asparagine-88, for example N88R or N88D, which can be combined with other mutations such as C125S, to confer added stability or selectivity. Other IL-2 muteins suitable for use in the disclosure are disclosed, for example muteins with alterations at aspartate-20 such as IL-2 D20T, or muteins having reduced affinity for the trimeric receptor as disclosed in U.S. Pat. No. 9,206,243. Particular embodiments for IL-2 and variants are given in SEQ ID No: 1-11.

```
native human IL-2

SEQ ID No: 1

APTSSSTKKT QLQLEHLLLD LQMILNGINN YKNPKLTRML TFKFYMPKKA

TELKHLQCLE EELKPLEEVL NLAQSKNFHL RPRDLISNIN VIVLELKGSE

TTFMCEYADE TATIVEFLNR WITFCQSIIS LT
```

-continued

IL-2-N88R (BAY 50-4798)

SEQ ID No: 2

APTSSSTKKTQLQLEHLLLDLQMILNGINNYKNPKLTRML
TFKFYMPKKATELKHLQCLEEELKPLEEVLNLAQSKNFHLRPRDLISRINVIVLELKG
SE TTFMCEYADETATIVEFLNRWITFCQSIISTLT

IL-2-N88R, C125S

SEQ ID No: 3

APTSSSTKKTQLQLEHLLLDLQMILNGINNYKNPKLTRML
TFKFYMPKKATELKHLQCLEEELKPLEEVLNLAQSKNFHLRPRDLISRINVIVLELKG
SE TTFMCEYADETATIVEFLNRWITFSQSIISTLT

IL-2-D20T

SEQ ID No: 4

APTSSSTKKTQLQLEHLLLDLQMILNGINNYKNPKLTRML
TFKFYMPKKATELKHLQCLEEELKPLEEVLNLAQSKNFHLRPRDLISRINVIVLELKG
SE TTFMCEYADETATIVEFLNRWITFCQSIISTLT

IL-2-D20T, C125S

SEQ ID No: 5

APTSSSTKKTQLQLEHLLLDLQMILNGINNYKNPKLTRML
TFKFYMPKKATELKHLQCLEEELKPLEEVLNLAQSKNFHLRPRDLISRINVIVLELKG
SE TTFMCEYADETATIVEFLNRWITFSQSIISTLT

IL-2-R38K, F42I, Y45N, E62L, E68V

SEQ ID No: 6

APTSSSTKKT QLQLEHLLLD LQMILNGINN YKNPKLTKML TIKFNMPKKA
TELKHLQCLE ELLKPLEVVL NLAQSKNFHL RPRDLISNIN VIVLELKGSE
TTFMCEYADE TATIVEFLNR WITFCQSIIS TLT

IL-2-R38K, F42Q, Y45E, E68V

SEQ ID No: 7

APTSSSTKKT QLQLEHLLLD LQMILNGINN YKNPKLTKML TQKFEMPKKA
TELKHLQCLE EELKPLEVVL NLAQSKNFHL RPRDLISNIN VIVLELKGSE
TTFMCEYADE TATIVEFLNR WITFCQSIIS TLT

IL-2-R38A, F42I, Y45N, E62L, E68V

SEQ ID No: 8

APTSSSTKKT QLQLEHLLLD LQMILNGINN YKNPKLTAML TIKFNMPKKA
TELKHLQCLE ELLKPLEVVL NLAQSKNFHL RPRDLISNIN VIVLELKGSE
TTFMCEYADE TATIVEFLNR WITFCQSIIS TLT

IL-2-R38K, F42K, Y45R, E62L, E68V

SEQ ID No: 9

APTSSSTKKT QLQLEHLLLD LQMILNGINN YKNPKLTKML TKKFRMPKKA
TELKHLQCLE ELLKPLEVVL NLAQSKNFHL RPRDLISNIN VIVLELKGSE
TTFMCEYADE TATIVEFLNR WITFCQSIIS TLT

IL-2 R38K, F42I, Y45E, E68V

SEQ ID No: 10

APTSSSTKKT QLQLEHLLLD LQMILNGINN YKNPKLTKML TIKFEMPKKA
TELKHLQCLE EELKPLEVVL NLAQSKNFHL RPRDLISNIN VIVLELKGSE
TTFMCEYADE TATIVEFLNR WITFCQSIIS TLT

IL-2 R38A, F42A, Y45A, E62A

SEQ ID No: 11

APTSSSTKKT QLQLEHLLLD LQMILNGINN YKNPKLTAML TAKFAMPKKA
TELKHLQCLE EALKPLEEVL NLAQSKNFHL RPRDLISNIN VIVLELKGSE
TTFMCEYADE TATIVEFLNR WITFCQSIIS TLT

13

Similarly, the native IL-15 may be replaced with a mutein conferring improved activity, receptor binding selectivity, or stability. For example, native IL-15 (SEQ ID No: 12) may be substituted by a mutein having improved resistance to degradation by asparagine deamidation, such as IL-15-[N77A] (SEQ ID No: 13) or IL-15-[N71S,N72A,N77A] (SEQ ID No: 14) which have been shown to retain their biological activity (Nellis et al., Pharm. Res. 29:722-38 (2012)), or IL-15[N72D] (SEQ ID No: 15) which shows enhanced receptor agonism (Zhu et al., J. Immunology 2009, 183(6): 3598).

```
IL-15
                                        SEQ ID No: 12
NWVNVISDLK KIEDLIQSMH IDATLYTESD VHPSCKVTAM
KCFLLELQVI SLESGDASIH DTVENLIILA NNSLSSNGNV
TESGCKECEE LEEKNIKEFL QSFVHIVQMF INTS

IL-15 [N77A]
                                        SEQ ID No: 13
NWVNVISDLK KIEDLIQSMH IDATLYTESD VHPSCKVTAM
```

14

```
                    -continued
KCFLLELQVI SLESGDASIH DTVENLIILA NNSLSSAGNV
TESGCKECEE LEEKNIKEFL QSFVHIVQMF INTS IL-15 [N71S, N72A, N77A]
                                        SEQ ID No: 14
NWVNVISDLK KIEDLIQSMH IDATLYTESD VHPSCKVTAM
KCFLLELQVI SLESGDASIH DTVENLIILA SASLSSAGNV
TESGCKECEE LEEKNIKEFL QSFVHIVQMF INTS IL-15 [N72D]
                                        SEQ ID No: 15
NWVNVISDLK KIEDLIQSMH IDATLYTESD VHPSCKVTAM
KCFLLELQVI SLESGDASIH DTVENLIILA NDSLSSNGNV
TESGCKECEE LEEKNIKEFL QSFVHIVQMF INTS
```

Complexes and fusion proteins of IL-15 with IL-15RαSu may also be used, for example the receptor-linked inter-leukin RLI (SEQ ID No: 16) and variants thereof (Mortier et al., J. Biological Chem. 2006, 281: 1612-9; U.S. Pat. No. 10,358,477). These fusion proteins may optionally comprise IL-15RαSu signal sequences and sequences known in the art to facilitate isolation and purification of the proteins, for example His-tags and Flag-tags, or these elements may be absent (SEQ ID No: 17).

```
RLI
                                        SEQ ID No: 16
MAPRRARGC RTLGLPALLL LLLLRPPATR GDYKDDDDKI EGRITCRRRM

SVEHADIWVK SYSLYSRERY ICNSGFKRKA GTSSLTECVL NKATNVAHWT

TPSLKCIRDP ALVHQRPAPP SGGSGGGGSG GGSGGGGSLQ NWVNVISDLK

KIQDLIQSMH IDATLYTESD VHPSCKVTAM KCFLLELQVI SLESGDASIH

DTVENLIILA NNSLSSNGNV TESGCKECEE LEEKNIKEFL QSFVHIVQMF INTS

RLI [N77A]
                                        SEQ ID No: 17
ITCPPPMSVE HADIWVKSY SLYSRERYIC NSGFKRKAGT SSLTECVLNK

ATNVAHWTTP SLKCIRDPAL VHQRPAPPSS GGSGGGGSGG GSGGGGSLQN

WVNVISDLKK IEDLIQSMHI DATLYTESDV HPSCKVTAMK CFLLELQVIS

LESGDASIHD TVENLIILAN NSLSSAGNVT ESGCKECEEL EEKNIKEFLQ

SFVHIVQMFI NTS
```

Other cytokines include IL-7, IL-9, IL-10, and IL-21 (SEQ ID Nos: 18-21).

```
IL-7
                                              SEQ ID No: 18
DCDIEGKDGK QYESVLMVSI DQLLDSMKEI GSNCLNNEFNFFKRHICDAN
KEGMFLFRAA RKLRQFLKMN STGDFDLHLL KVSEGTTILL NCTGQVKGRK
PAALGEAQPT KSLEENKSLK EQKKLNDLCF LKRLLQEIKT CWNKILMGTK EH

IL-9
                                              SEQ ID No: 19
QGCPTLAGIL DINFLINKMQ EDPASKCHCS ANVTSCLCLG IPSDNCTRPC
FSERLSQMTN TTMQTRYPLI FSRVKKSVEV LKNNKCPYFS CEQPCNQTTA
GNALTFLKSL LEIFQKEKMR GMRGKI

IL-21
                                              SEQ ID No: 20
QGQDRHMIRM RQLIDIVDQL KNYVNDLVPE FLPAPEDVET NCEWSAFSCF
QKAQLKSANT GNNERIINVS IKKLKRKPPS TNAGRRQKHR LTCPSCDSYE
KKPPKEFLER FKSLLQKMIH QHLSSRTHGS EDS

IL-10
                                              SEQ ID No: 21
MSPGQGTQSE NSCTHFPGNL PNMLRDLRDA FSRVKTFFQM KDQLDNLLLK
ESLLEDFKGY LGCQALSEMI QFYLEEVMPQ AENQDPDIKA HVNSLGENLK
TLRLRLRRCH RFLPCENKSK AVEQVKNAFN KLQEKGIYKA MSEFDIFINY
IEAYMTMKIR N
```

In certain embodiments, the cytokines may be chemically modified, for example by attachment of water-soluble polymers such as polyethylene glycols, at one or more positions so as to prolong the duration of the protein in the body once released from the conjugate and/or to modify the receptor selectivity.

These proteins may be prepared using methods known in the art. When prepared recombinantly, they may be expressed either in prokaryotic or eukaryotic systems.

A variety of cleavable linkers L may be used, including those disclosed in U.S. Pat. No. 8,680,315; PCT Publication No. WO2013/036857; PCT Publication No. WO2006/138572; PCT Publication No. WO2005/099768; PCT Publication No. WO2006/136586; PCT Publication No. WO2011/012722; PCT Publication No. WO2011/089214; PCT Publication No. WO2011/089215; PCT Publication No WO2011/089216; and PCT Publication No. WO2016/020373. The linker L comprises a covalent bond that cleaves at a particular rate under appropriate conditions. Such cleavage may be through catalyzed or uncatalyzed hydrolysis, proteolysis, or elimination reactions. Appropriate conditions for cleavage are those typically found in physiological environments, typically a pH of approximately 6.5-7.5 and a temperature of 30-45° C. and preferably pH at approximately 7.4 and a temperature at approximately 37° C.

In some embodiments, the linker-drug of formula (I) is a compound of formula (Ia):

$$\text{(Ia)}$$

$$Z\!-\!S\!-\!(CH_2)_n\!-\!\underset{\underset{R^4}{|}}{\overset{\overset{R^4}{|}}{C}}\!-\!\underset{\underset{H}{|}}{\overset{\overset{\overset{\overset{R^1}{|}}{HC\!-\!R^2}}{|}}{C}}\!-\!O\!-\!\overset{\overset{O}{\|}}{C}\!-\!Y\!-\!D,$$

wherein:
n is an integer from 0 to 6;
R$^1$ and R$^2$ are independently an electron-withdrawing group, alkyl, or H, and wherein at least one of R$^1$ and R$^2$ is an electron-withdrawing group;

each R$^4$ is independently C$_1$-C$_3$ alkyl or the two R$^4$ are taken together with the carbon atom to which they attach to form a 3-6 member ring;

Z is a group for connecting the linker to a macromolecular carrier;

S is absent or is (CH$_2$CH$_2$O)$_h$(CH$_2$)$_g$CONH, wherein g is an integer from 1 to 6 and h is an integer from 0 to 1000;

Y is absent or is NH(CH$_2$CH$_2$O)$_p$(CH$_2$)$_m$, wherein m is an integer from 2 to 6 and p is an integer from 0 to 1000; and D is an amine residue of a cytokine or cytokine variant as disclosed herein.

In some embodiments of a linker-drug of formula (Ia), n=1-6, R$^1$ and R$^2$ are independently electron-withdrawing groups, alkyl, or H, and wherein at least one of R$^1$ and R$^2$ is an electron-withdrawing group; each R$^4$ is independently H or C$_1$-C$_3$ alkyl or taken together may form a 3-6 membered ring; Z is a group for connecting the linker to a macromolecular carrier; S is absent or is (CH$_2$CH$_2$O)$_h$(CH$_2$)$_g$CONH wherein g=1-6 and h=0-1000; Y is absent or is NH(CH$_2$CH$_2$O)$_p$(CH$_2$)$_m$ wherein m=2-6 and p=0-1000; and D is an amine residue of IL-2, an IL-2 variant, an IL-15, or an IL-15 variant cytokine.

A description of the electron-withdrawing group of R$^1$ and R$^2$ can be found in U.S. Pat. No. 8,680,315, which is incorporated herein by reference. Electron-withdrawing groups are defined as groups having a Hammett sigma value greater than 0 (see, for example, Hansch et al. 1991 Chemical Reviews 91: 165-195). Typical examples of electron-withdrawing groups include, without limitation, nitrile, nitro, sulfones, sulfoxides, carbonyls, optionally substituted aryls and optionally substituted heteroaryls.

In some embodiments of a linker-drug of formula (Ia), the electron-withdrawing group of R$^1$ and R$^2$ is

—CN;

—NO$_2$;

optionally substituted aryl;

optionally substituted heteroaryl;

optionally substituted alkenyl;

optionally substituted alkynyl;

—COR$^5$, —SOR$^5$, or —SO$_2$R$^5$, wherein $R^5$ is H, optionally substituted alkyl, optionally substituted aryl, optionally substituted arylalkyl, optionally substituted heteroaryl, optionally substituted heteroarylalkyl, —$OR^6$ or —$NR^6_2$, wherein each $R^6$ is independently H, optionally substituted alkyl, optionally substituted aryl, or optionally substituted heteroaryl, or both $R^6$ groups are taken together with the nitrogen to which they are attached to form a heterocyclic ring; or $SR^7$, wherein $R^7$ is optionally substituted alkyl, optionally substituted aryl, optionally substituted arylalkyl, optionally substituted heteroaryl, or optionally substituted heteroarylalkyl.

In some embodiments of a linker-drug of formula (Ia), the electron-withdrawing group of $R^1$ and $R^2$ is —CN. In some embodiments, the electron-withdrawing group of $R^1$ and $R^2$ is —$NO_2$. In some embodiments, the electron-withdrawing group of $R^1$ and $R^2$ is optionally substituted aryl containing κ-10 carbons. For instance, in some embodiments, the electron-withdrawing group of $R^1$ and $R^2$ is optionally substituted phenyl, naphthyl, or anthracenyl. In some embodiments, the electron-withdrawing group of $R^1$ and $R^2$ is optionally substituted heteroaryl comprising 3-7 carbons and containing at least one N, O, or S atom. For instance, in some embodiments, the electron-withdrawing group of $R^1$ and $R^2$ is pyrrolyl, pyridyl, pyrimidinyl, imidazolyl, oxazolyl, isoxazolyl, thiazolyl, isothiazolyl, quinolyl, indolyl, or indenyl, each of which is optionally substituted. In some embodiments, the electron-withdrawing group of $R^1$ and $R^2$ is optionally substituted alkenyl containing 2-20 carbon atoms. In some embodiments, the electron-withdrawing group of $R^1$ and $R^2$ is optionally substituted alkynyl containing 2-20 carbon atoms. In some embodiments, the electron-withdrawing group of $R^1$ and $R^2$ is —$COR^5$, —$SOR^5$, or —$SO_2R^5$, wherein $R^5$ is H, optionally substituted alkyl containing 1-20 carbon atoms, optionally substituted aryl, optionally substituted arylalkyl, optionally substituted heteroaryl, optionally substituted heteroarylalkyl, —$OR^6$ or —$NR^6_2$, wherein each $R^6$ is independently H or optionally substituted alkyl containing 1-20 carbon atoms, or both $R^6$ groups are taken together with the nitrogen to which they are attached to form a heterocyclic ring. In some embodiments, the electron-withdrawing group of $R^1$ and $R^2$ is —$SR^7$, wherein $R^7$ is optionally substituted alkyl containing 1-20 carbon atoms, optionally substituted aryl, optionally substituted arylalkyl, optionally substituted heteroaryl, or optionally substituted heteroarylalkyl.

In some embodiments of a linker-drug of formula (Ia), at least one of $R^1$ and $R^2$ is —CN, —$SOR^5$ or —$SO_2R^5$. In some embodiments, at least one of $R^1$ and $R^2$ is —CN or —$SO_2R^5$. In some embodiments, at least one of $R^1$ and $R^2$ is —CN or —$SO_2R^5$, wherein $R^5$ is optionally substituted alkyl, optionally substituted aryl, or. In some embodiments, at least one of $R^1$ and $R^2$ is —CN, —$SO_2N(CH_3)_2$, —$SO_2CH_3$, —$SO_2Ph$, —$SO_2PhCl$, —$SO_2N(CH_2CH_2)_2O$, —$SO_2CH(CH_3)_2$, —$SO_2N(CH_3)(CH_2CH_3)$, or —$SO_2N(CH_2CH_2OCH_3)_2$.

In some embodiments of a linker-drug of formula (Ia), each $R^4$ is independently $C_1$-$C_3$ alkyl. In some embodiments, at least one $R^4$ is methyl. In some embodiments, both $R^4$ are methyl.

In some embodiments of a linker-drug of formula (Ia), n is an integer from 1 to 6. In some embodiments, n is an integer from 1 to 3. In some embodiments, n is an integer from 0 to 3. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments of a linker-drug of formula (Ia), $R^1$ is CN or —$SO_2R^5$, wherein $R^5$ is $C_1$-$C_6$ alkyl, aryl, heteroaryl, or —$NR^6_2$, wherein $R^6$ is independently $C_1$-$C_6$ alkyl, aryl, or heteroaryl, and $R^2$=H, wherein each of $R^5$ and $R^6$ is independently optionally substituted.

In some embodiments of a linker-drug of formula (Ia), Z can comprise any functional group known in the art for conjugation. Examples of such functional groups include, without limitation, amine, aminooxy, ketone, aldehyde, maleimidyl, thiol, alcohol, azide, 1,2,4,5-tetrazinyl, trans-cyclooctenyl, bicyclononynyl, cyclooctynyl, and protected variants thereof. In some embodiments, Z comprises protected amine, protected aminooxy, ketone or protected ketone, aldehyde or protected aldehyde, maleimidyl, protected thiol, protected alcohol, azide, 1,2,4,5-tetrazinyl, trans-cyclooctenyl, bicyclononynyl, or cyclooctynyl. In some embodiments, Z comprises azide, ketone, or protected ketone. In some embodiments, Z comprises a functional group capable of reacting selectively with a cognate functional group Z' on a macromolecular carrier to form a connecting functionality Z*. In some embodiments, the connecting functionality Z* is carboxamide when Z/Z' is amine/carboxylate or active ester; oxime when Z/Z' is $NH_2O$/ketone or aldehyde; thioether when Z/Z' is thiol/maleimide or halocarbonyl; or triazole when Z/Z' is azide/cyclooctyne.

In some embodiments of a linker-drug of formula (Ia), S is absent. In some embodiments, S is $(CH_2CH_2O)_h(CH_2)_gCONH$.

In some embodiments of a linker-drug of formula (Ia), Y is absent. In some embodiments, Y is $NH(CH_2CH_2O)_p(CH_2)_m$.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to $R^1$ of formula (I) may be combined with every description, variation, embodiment or aspect of Z, S, n, $R^2$, $R^4$, Y, and/or D, the same as if each and every combination were specifically and individually listed. It is also understood that all descriptions, variations, embodiments or aspects of any formulae such as formula (I), (Ia), (IIa), (IIIa), (IV), (V), or (VI), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae as detailed herein, such as formula (Ia), (IIa), (IIIa), (IV), (V), or (VI), and are equally described, the same as if each and every description, variation, embodiment or aspect were separately and individually listed for all formulae.

Linker

In another aspect, provided is a linker of formula (IIa):

$$Z—S—(CH_2)_n—\underset{\underset{R^4}{|}}{\overset{\overset{R^4}{|}}{C}}—\underset{\underset{H}{|}}{\overset{\overset{HC—R^2}{\overset{|}{}}\overset{R^1}{|}}{C}}—O—\overset{\overset{O}{\|}}{C}—X \quad \text{(IIa)}$$

wherein n, Z, S, $R^1$, $R^2$, and $R^4$ are as disclosed herein for formula (Ia); and X is halogen, active ester (e.g., N-succin-imidyloxy, nitrophenoxy, or pentahalophenoxy), or $NH(CH_2CH_2O)_p(CH_2)_{(m-1)}CHO$, wherein m is an integer from 2 to 6 and p is a an integer from 0 to 1000. In some embodiments, X is halogen. In some embodiments, X is an active ester such as succinimidyloxy. In some embodiments, X is halide, succinimidyloxy, or nitrophenoxy. In some embodiments, X is $NH(CH_2CH_2O)_p(CH_2)_{(m-1)}CHO$. The linker in which X is $NH(CH_2CH_2O)_p(CH_2)_{(m-1)}CHO$ may be attached to the cytokine by reductive alkylation, in which the aldehyde group of the linker forms an imine with an amine group of the cytokine, and this imine is reduced to an amine in the presence of a reducing agent such as sodium cyanoborohydride. This method is typically selective for connection of the linker to the N-terminal alpha-amine group of the cytokine. In this embodiment, the cytokine that is released from the conjugates upon cleavage of the linker is modified at the N-terminal alpha-amine by the addition of $NH_2(CH_2CH_2O)_p(CH_2)_m$. These linkers are prepared as described in Schneider et al. (2016) *Bioconjugate Chem* 27: 2534-9 (incorporated herein by reference). In some embodiments, p is 0 and the cytokine that is released from the conjugates upon cleavage of the linker is modified at the N-terminal alpha-amine by the addition of $NH_2(CH_2)_m$.

In some embodiments of a linker of formula (IIa), n=1-6, $R^1$ and $R^2$ are independently electron-withdrawing groups, alkyl, or H, and wherein at least one of $R^1$ and $R^2$ is an electron-withdrawing group; each $R^4$ is independently H or $C_1$-$C_3$ alkyl or taken together may form a 3-6 membered ring; Z is a group for connecting the linker to a macromo-lecular carrier; S is absent or is $(CH_2CH_2O)_h(CH_2)_gCONH$ wherein g=1-6 and h=0-1000; and X is halide, succinim-idyloxy, or nitrophenoxy.

The preparation of these linker reagents is disclosed in U.S. Pat. No. 8,680,315 and PCT Patent Application PCT/US2020/026726 (filed Apr. 3, 2020), both of which are incorporated herein by reference.

These linkers are attached to the cytokine or cytokine variant by methods known in the art, for example, by reacting with a buffered solution of the protein at pH between 6 and 9, preferably at pH between 7 and 8, such that amine groups on the protein are acylated to form linker-proteins of formula (I). When more than one amine group on the protein is available for reaction, multiple linkers may be attached to each protein. Selectivity for the number of linkers attached to a protein may be controlled using the stoichiometry of linker reagent to protein. When only one linker is attached, the protein that is released from the conjugates upon cleavage of the linker has no additional modifications.

Conjugate

In another aspect, provided is a conjugate of formula (III):

$$M\text{-}[Z^*\text{-}L\text{-}D]_q \quad \text{(III)}$$

wherein M is a macromolecular carrier, $Z^*$ is a connecting functionality, L is a cleavable linker, D is a cytokine or cytokine variant protein, and q is an integer from 1 to 10 when M is a soluble macromolecular carrier or q is a multiplicity when M is an insoluble macromolecular carrier. It is understood that, when M is an insoluble macromolecu-lar carrier such as an insoluble matrix or support, a multi-plicity of linker-drugs can be attached to M. For example, in some embodiments, when M is a hydrogel of formula (IV) wherein both $P^1$ and $P^2$ are 4-armed polymers, 1, 2, 3, or 4 linker-drugs can be attached to each $P^1$-$P^2$ unit. Thus, the desired multiplicity can be achieved by reacting the linker-drug with M in a suitable ratio. As such, suitable drug concentration in the volume of the matrix can be achieved.

In some embodiments, the conjugate of formula (III) is of formula (IIIa):

$$M\!\!-\!\!\left[Z^*—S—(CH_2)_n—\underset{\underset{R^4}{|}}{\overset{\overset{R^4}{|}}{C}}—\underset{\underset{H}{|}}{\overset{\overset{HC—R^2}{\overset{|}{}}\overset{R^1}{|}}{C}}—O—\overset{\overset{O}{\|}}{C}—Y—D\right]_q. \quad \text{(IIIa)}$$

wherein M, $Z^*$, S, n, $R^1$, $R^2$ and $R^4$, Y and D are defined as detailed herein for Formula (I), (Ia), or (IIa).

In some embodiments, M is a soluble macromolecular carrier such as polyethylene glycols, dextrans, proteins, or antibodies; $Z^*$ is a connecting group; q=1 to 10. In each case, M comprises a reactive group $Z'$ which reacts with group Z on the compound of formula (I) to form connecting group $Z^*$. Connecting group $Z^*$ is carboxamide when $Z/Z'$ is amine/carboxylate or active ester; oxime when $Z/Z'$ is aminooxy/ketone or aldehyde; thioether when $Z/Z'$ is thiol/maleimide or halocarbonyl; or triazole when $Z/Z'$ is azide/cyclooctyne. In some embodiments, $Z^*$ comprises an amide, carboxamide, oxime, triazole, thioether, thiosuccinimide, or ether. In some embodiments, In some embodiments, M is a polyethylene glycol of average molecular weight between 1,000 and 100,000 dal-tons, preferably between 10,000 and 60,000 daltons, and most preferably between 20,000 and 40,000 daltons. M may be single chain, branched chain, or multi-armed. M com-prises one or more functional groups $Z'$ for connection to the linker drug. $Z'$ may be attached to commercially-available polymers M using methods known in the art; for example, when M comprises an amine group, this can be further derivatized by acylation to introduce $Z'$=aminooxy through reaction with (Boc-aminooxy)acetic acid followed by depro-tection; by acylation to introduce $Z'$=cyclooctyne through reaction with an active ester or carbonate of a cyclooctyne (for example, 4-cyclooctynyl succinimidyl carbonate or (1R,8S,9s)-bicyclo[6.1.0]non-4-yn-9-ylmethoxy succinim-idyl carbonate (BCN-OSu) or its (1R,8S,9r) diastereomer); or by acylation to introduce a maleimide group through reaction with 3-maleimidopropionic acid.

In some embodiments, M is an insoluble macromolecular carrier such as a hydrogel or surgical device. In such embodiments, q is a multiplicity determined by the number of reactive groups $Z'$ attached to the insoluble support. In some embodiments, M is a degradable crosslinked hydrogel of formula (IV):

(IV)

$$P^1 \left[ A^* - (CH_2)_n - \underset{\underset{R^{14}}{|}}{\overset{\overset{R^{14}}{|}}{C}} - \underset{\underset{H}{|}}{\overset{\overset{HC-R^{12}}{\overset{|}{R^{11}}}}{C}} - O - \overset{\overset{O}{||}}{C} - \underset{H}{N} - (CH_2)_x - \underset{\underset{H}{|}}{\overset{\overset{(CH_2)_yB}{|}}{C}} - (CH_2)_z - C^* \right]_r P^2,$$

wherein $P^1$ and $P^2$ are independently a r-armed polymer wherein r is an integer from 2 to 8;

n is an integer from 0 to 6;

x, y, and z are each independently an integer from 0-6;

B is a group comprising Z';

$A^*$ and $C^*$ are each independently a connecting group such as a carboxamide, oxime, ether, thioether, or triazole;

$R^{11}$ and $R^{12}$ are each independently H, $C_1$-$C_4$ alkyl, or an electron-withdrawing group, wherein at least one of $R^{11}$ or $R^{12}$ is an electron-withdrawing group; and each $R^{14}$ is independently $C_1$-$C_3$ alkyl or the two $R^{14}$ are taken together with the carbon atom to which they attach to form a 3-6 member ring;

A description of the electron-withdrawing groups $R^{11}$ and $R^{12}$ can be found in U.S. Pat. No. 8,680,315 which is incorporated herein by reference. In some embodiments of a hydrogel of formula (IV), the electron-withdrawing group of $R^{11}$ and $R^{12}$ is

—CN;

—$NO_2$;

optionally substituted aryl;

optionally substituted heteroaryl;

optionally substituted alkenyl;

optionally substituted alkynyl;

—$COR^{15}$, —$SOR^{15}$, or —$SO_2R^{15}$, wherein $R^{15}$ is H, optionally substituted alkyl, optionally substituted aryl, optionally substituted arylalkyl, optionally substituted heteroaryl, optionally substituted heteroarylalkyl, —$OR^{16}$ or —$NR^{16}_2$, wherein each $R^{16}$ is independently H, optionally substituted alkyl, optionally substituted aryl, or optionally substituted heteroaryl, or both $R^{16}$ groups are taken together with the nitrogen to which they are attached to form a heterocyclic ring; or $SR^{17}$, wherein $R^{17}$ is optionally substituted alkyl, optionally substituted aryl, optionally substituted arylalkyl, optionally substituted heteroaryl, or optionally substituted heteroarylalkyl.

In some embodiments of a hydrogel of formula (IV), the electron-withdrawing group of $R^{11}$ and $R^{12}$ is —CN. In some embodiments, the electron-withdrawing group of $R^{11}$ and $R^{12}$ is —$NO_2$. In some embodiments, the electron-withdrawing group of $R^{11}$ and $R^{12}$ is optionally substituted aryl containing 6-10 carbons. For instance, in some embodiments, the electron-withdrawing group of $R^{11}$ and $R^{12}$ is optionally substituted phenyl, naphthyl, or anthracenyl. In some embodiments, the electron-withdrawing group of $R^{11}$ and $R^{12}$ is optionally substituted heteroaryl comprising 3-7 carbons and containing at least one N, O, or S atom. For instance, in some embodiments, the electron-withdrawing group of $R^{11}$ and $R^{12}$ is pyrrolyl, pyridyl, pyrimidinyl, imidazolyl, oxazolyl, isoxazolyl, thiazolyl, isothiazolyl, quinolyl, indolyl, or indenyl, each of which is optionally substituted. In some embodiments, the electron-withdrawing group of $R^{11}$ and $R^{12}$ is optionally substituted alkenyl containing 2-20 carbon atoms. In some embodiments, the electron-withdrawing group of $R^{11}$ and $R^{12}$ is optionally substituted alkynyl containing 2-20 carbon atoms. In some embodiments, the electron-withdrawing group of $R^{11}$ and $R^{12}$ is —$COR^5$, —$SOR^5$, or —$SO_2R^5$, wherein $R^5$ is H, optionally substituted alkyl containing 1-20 carbon atoms, optionally substituted aryl, optionally substituted arylalkyl, optionally substituted heteroaryl, optionally substituted heteroarylalkyl, —$OR^{16}$ or —$NR^{16}_2$, wherein each $R^{16}$ is independently H or optionally substituted alkyl containing 1-20 carbon atoms, or both $R^{16}$ groups are taken together with the nitrogen to which they are attached to form a heterocyclic ring. In some embodiments, the electron-withdrawing group of $R^{11}$ and $R^{12}$ is —$SR^{17}$, wherein $R^{17}$ is optionally substituted alkyl containing 1-20 carbon atoms, optionally substituted aryl, optionally substituted arylalkyl, optionally substituted heteroaryl, or optionally substituted heteroarylalkyl.

In some embodiments of a hydrogel of formula (IV), at least one of $R^{11}$ and $R^{12}$ is —CN, —$SOR^{15}$ or —$SO_2R^{15}$. In some embodiments, at least one of $R^{11}$ and $R^{12}$ is —CN or —$SO_2R^{15}$. In some embodiments, at least one of $R^{11}$ and $R^{12}$ is —CN or —$SO_2R^{15}$, wherein $R^{15}$ is optionally substituted alkyl, optionally substituted aryl, or. In some embodiments, at least one of $R^{11}$ and $R^{12}$ is —CN, —$SO_2N(CH_3)_2$, —$SO_2CH_3$, —$SO_2Ph$, —$SO_2PhCl$, —$SO_2N(CH_2CH_2)_2O$, —$SO_2CH(CH_3)_2$, —$SO_2N(CH_3)(CH_2CH_3)$, or —$SO_2N(CH_2CH_2OCH_3)_2$.

In some embodiments of a hydrogel of formula (IV), each $R^{14}$ is independently $C_1$-$C_3$ alkyl. In some embodiments, at least one $R^{14}$ is methyl. In some embodiments, both $R^{14}$ are methyl.

In some embodiments of a hydrogel of formula (IV), $R^{11}$ is CN or —$SO_2R^{15}$, wherein $R^{15}$ is $C_1$-$C_6$ alkyl, aryl, heteroaryl, or —$NR^{16}_2$, wherein each $R^{16}$ is independently $C_1$-$C_6$alkyl, aryl, or heteroaryl, and $R^{12}$=H, wherein each of $R^5$ and $R^{16}$ is independently optionally substituted.

Figure 1:
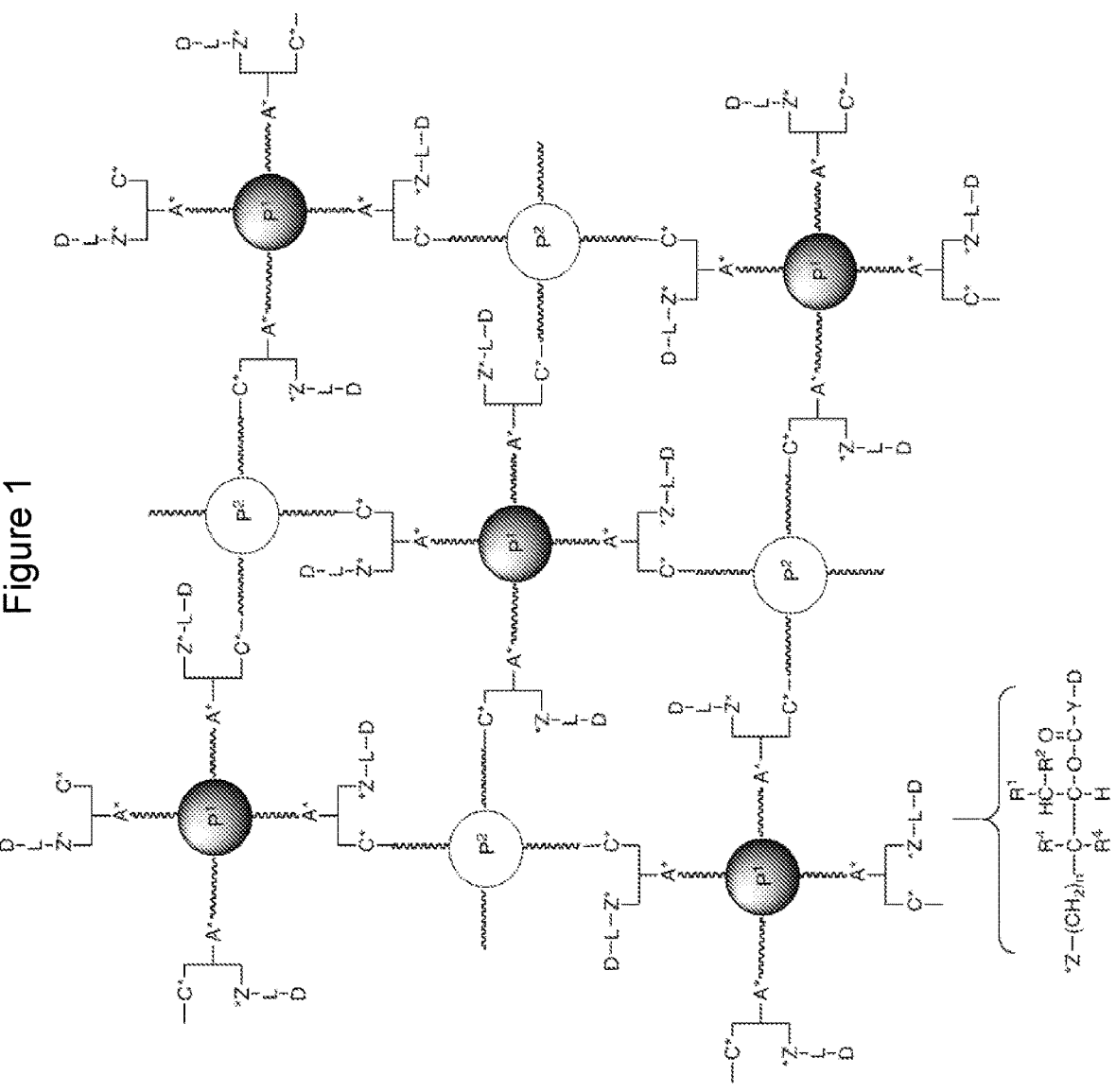
FIG. 1 shows a generic structure of a conjugate wherein linker-drug is attached to a hydrogel.

A general formula for the linker-protein attached to such hydrogels is shown in FIG. 1.

In particular embodiments, M is a hydrogel of formula (V) or formula (VI)

(V)

$$P^1 \left[ A^* - (CH_2)_n - \underset{\underset{R^{14}}{|}}{\overset{\overset{R^{14}}{|}}{C}} - \underset{\underset{H}{|}}{\overset{\overset{HC-R^{12}}{\overset{|}{R^{11}}}}{C}} - O - \overset{\overset{O}{||}}{C} - \underset{H}{N} - \underset{\underset{H}{|}}{\overset{\overset{(CH_2)_4}{|}}{C}} - \overset{\overset{O}{||}}{C} - NH \right]_r P^2$$

with $HN - \overset{\overset{O}{||}}{C} - Z'$ substituent

-continued (VI)

wherein $P^1$, $P^2$, r, $R^{11}$, $R^{12}$, and $R^{14}$ are as detailed herein for formula (IV); and Z' comprises a cyclooctyne group. In particular embodiments, Z' is 4-cyclooctynyloxycarbonyl or (1R,8S,9s)-bicyclo[6.1.0]non-4-yn-9-ylmethoxycarbonyl.

Preparation of hydrogel supports of these formulas are disclosed in U.S. Pat. No. 9,649,385 and PCT/US2020/026726 (filed Apr. 3, 2020), each of which is incorporated herein by reference.

The above-described conjugates may be used for supplying a low, continuous dose of the cytokine in a subject having a disease or condition that can be treated with such a regimen. Particular diseases and conditions treatable with low, continuous dose cytokine therapy include chronic graft-vs-host disease (cGVHD) associated with inadequate reconstitution of tolerogenic CD4$^+$ CD25$^+$ FOXP3$^+$ regulatory T cells (Koreth et al., *Blood* 128: 130-7 (2016)); systemic lupus erythematosis; sarcoidosis; Hepatitis C-induced vasculitis; alopecia areata; rheumatoid arthritis; inflammatory bowel disease; multiple sclerosis; and type-1 diabetes (Koreth et al., *Oncology & Hematology Review* 10: 157-63 (2014)). Immune augmentation through exogenous cytokines may be useful in the treatment of cancers and immunodeficiencies.

The conjugates of the disclosure may be formulated using standard buffers and excipients known in the art. Buffers used are preferably between pH 3 and pH 7, more preferably between pH 4 and pH 6. Administration may be intravenous, subcutaneous, or intravitreal, intramuscular for soluble conjugates and may be subcutaneous, intravitreal, or intramuscular for insoluble conjugates. Intratumoral injection may also be used.

Pharmaceutical Compositions

In another aspect, provided herein are pharmaceutical compositions comprising the macromolecular carrier-drug conjugates or pharmaceutically acceptable salts thereof together with a pharmaceutically acceptable buffer and/or excipient. Buffers are chosen such that the stability of the linker is maintained during storage and upon reconstitution if required, and typically have a pH between 2 and 7, preferably between 2 and 6, and more preferably between 2 and 5. Acceptable buffers include acetic acid, citric acid, phosphoric acid, histidine, gluconic acid, aspartic acid, glutamic acid, lactic acid, tartaric acid, succinic acid, malic acid, fumaric acid, alpha-ketoglutaric acid, and the like. Excipients may include tonicity and osmolality agents such as sodium chloride; preservatives such as citric acid or a citrate salt, and parabens; antibacterials such as phenol and cresol; antioxidants such as butylated hydroxytoluene, vitamin A, C, or E, cysteine, and methionine; density modifiers such as sucrose, polyols, hyaluronic acid, and carboxymethylcellulose. These formulations can be prepared by conventional methods known to those skilled in the art, for example as described in "Remington's Pharmaceutical Science," A. R. Gennaro, ed., 17$^{th}$ edition, 1985, Mack Publishing Company, Easton, PA, USA. The pharmaceutical compositions may be supplied in liquid solution or suspension, or may be provided as a solid, for example by lyophilization of a liquid composition. Such lyophils may further comprise bulking agents to ensure rapid and efficient reconstitution prior to use.

Methods of Use

In another aspect, the presently described macromolecular carrier-drug conjugates and pharmaceutical compositions comprising them may be used to treat or prevent a disease or condition in an individual. In some embodiments, provided are methods of treating a disease or condition comprising administering to the individual in need thereof a macromolecular carrier-drug conjugate described herein or a pharmaceutical compositions comprising a macromolecular carrier-drug conjugate described herein. The "individual" may be a human, or may be an animal, such as a cat, dog, cow, rat, mouse, horse, rabbit, or other domesticated animal.

Also provided are compositions containing a macromolecular carrier-drug conjugate described herein, for use in the treatment of a disease or condition. Also provided herein is the use of a macromolecular carrier-drug conjugate described herein in the manufacture of a medicament for treatment of a disease or condition.

The applicable disease or condition requiring treatment will be known by one of skill in the art from the nature of the conjugate drug.

Certain representative embodiments are provided below.

Embodiment 1. A conjugate having the formula $$M\text{-}[Z^*\text{-}L\text{-}D]_q$$

wherein M is a macromolecular carrier;

Z* is a connecting functionality;

L is a cleavable linker; and

D is the amine residue of a cytokine or variant thereof; and wherein when M is a soluble carrier, q=1-10, and wherein when M is an insoluble carrier, q is a multiplicity.

Embodiment 2. The conjugate of Embodiment 1 wherein Z* is a carboxamide, oxime, thioether, or triazole; and L has the formula wherein n=0-6 or 1-6;

$R^1$ and $R^2$ are independently electron-withdrawing groups, alkyl, or H, wherein at least one of $R^1$ and $R^2$ is an electron-withdrawing group;

each $R^4$ is independently H or $C_1$-$C_3$ alkyl or both $R^4$ taken together form a 3-6 membered ring;

S is absent or $(CH_2CH_2O)_h(CH_2)_g CONH$ wherein g=1-6 and h=0-1000;

Y is absent or is $NH(CH_2CH_2O)_p(CH_2)_m$ wherein m=2-6 and p=0-1000.

Embodiment 3. The conjugate of Embodiment 2 wherein $R^1$ is CN or $R^5SO_2$, wherein $R^5$ is $C_1$-$C_6$ alkyl, aryl, heteroaryl, or is $(R^6)_2N$, wherein $R^6$ is $C_1$-$C_6$ alkyl, aryl, or heteroaryl, and $R^2$=H, and wherein each of $R^4$-$R^6$ may optionally be substituted.

Embodiment 4. The conjugate of any of Embodiments 1-3 wherein M is a soluble polyethylene glycol of average molecular weight between 1,000 and 100,000 daltons, and q=1-10.

Embodiment 5. The conjugate of any of Embodiments 1-3 wherein M is an insoluble hydrogel or surgical device, and q is a multiplicity.

Embodiment 6. The conjugate of any of Embodiments 1-3 wherein D is IL-2, IL-7, IL-9, IL-10, IL-15, IL-21 or a variant thereof.

Embodiment 7. The conjugate of Embodiment 6 wherein D is an IL-2 variant having selective binding for the trimeric $\alpha\beta\gamma$-receptor over the dimeric $\beta\gamma$ receptor or is an IL-2 variant having selective binding for the dimeric $\beta\gamma$-receptor over the trimeric $\alpha\beta\gamma$-receptor.

Embodiment 8. The conjugate of any of Embodiments 1-3 wherein D is an IL-15 variant stabilized against deamidation.

Embodiment 9. A linker-protein of formula $$Z-S-(CH_2)_n-\underset{\underset{R^4}{|}}{\overset{\overset{R^4}{|}}{C}}-\underset{\underset{H}{|}}{\overset{\overset{HC-R^2}{|}}{C}}-O-\overset{\overset{O}{||}}{C}-Y-D$$

with the substituent $R^1$ on the $HC-R^2$ carbon wherein n=0-6 or 1-6, $R^1$ and $R^2$ are independently electron-withdrawing groups, alkyl, or H, and wherein at least one of $R^1$ and $R^2$ is an electron-withdrawing group; each $R^4$ is independently H or $C_1$-$C_3$ alkyl or taken together may form a 3-6 member ring; Z is a functional group for connecting the linker to a macromolecular carrier; S is absent or $(CH_2CH_2O)_h(CH_2)_g CONH$ wherein g=1-6 and h=0-1000; Y is absent or is $NH(CH_2CH_2O)_p(CH_2)_m$ wherein m=2-6 and p=0-1000; and D is an amine residue of a cytokine or a variant thereof.

Embodiment 10. The linker-protein of Embodiment 9 wherein $R^1$ is CN or $R^5SO_2$, wherein $R^5$ is $C_1$-$C_6$ alkyl, aryl, heteroaryl, or is $(R^6)_2N$, wherein $R^6$ is $C_1$-$C_6$ alkyl, aryl, or heteroaryl, and $R^2$=H, and wherein each of $R^4$-$R^6$ may optionally be substituted.

Embodiment 11. The linker-protein of Embodiment 9 or 10 wherein D is IL-2, IL-7, IL-9, IL-10, IL-15, IL-21 or a variant thereof.

Embodiment 12. The linker-protein of Embodiment 11 wherein D is an IL-2 variant having selective binding for the trimeric $\alpha\gamma$-receptor over the dimeric $\beta\gamma$ receptor, or is an IL-2 variant having selective binding for the dimeric $\beta\gamma$-receptor over the trimeric $\alpha\gamma$-receptor.

Embodiment 13. The linker-protein of Embodiment 12 wherein D is selected from the group consisting of IL-2, IL-2 N88R, IL-2 N88D, IL-2 N88R, C125S, and IL-2 N88D, C125S.

Embodiment 14. The linker-protein of Embodiment 9 or 10 wherein D is selected from the group consisting of IL-15, IL-15 N77A, and IL-15-[N71S,N72A,N77A].

Embodiment 15. The linker-protein of Embodiment 9 or 10 wherein D is selected from the group consisting of IL-2, IL-7, IL-9, IL-10, IL-15, IL-21, or a variant thereof wherein the N-alpha amine group is modified by addition of $NH_2$ $(CH_2CH_2O)_p(CH_2)_m$ wherein m=2-6 and p=0-1000.

Embodiment 16. A method of selectively expanding $T_{reg}$ cells in a subject, consisting of treating the subject with a conjugate of any of Embodiments 1-3 wherein D is IL-2 or an IL-2 variant.

Embodiment 17. A method of selectively expanding CD8+ effector T cells in a subject, consisting of treating the subject with a conjugate of any of Embodiments 1-3 wherein D is IL-15 or an IL-15 variant.

Embodiment 18. A method to treat a disease or condition in a subject requiring such treatment, comprising administering the conjugate of any of Embodiments 1-8.

Embodiment 19. The method of Embodiment 18 wherein the disease or condition is an autoimmune disease, chronic graft-vs-host disease (cGVHD) associated with inadequate reconstitution of tolerogenic CD4$^+$CD25$^+$ FOXP3$^+$ regulatory T cells; systemic lupus erythrematosis; sarcoidosis; Hepatitis C-induced vasculitis; alopecia; rheumatoid arthritis; inflammatory bowel disease; multiple sclerosis; or type-1 diabetes.

Embodiment 20. A method for the augmentation of immunotherapy in a subject undergoing such therapy, consisting of administering a conjugate of any of Embodiments 1-8.

The following examples will serve to illustrate rather than limit the scope of the disclosure. All references cited within are hereby incorporated by reference, including those cited for particular aspects of their disclosures, specifically for those aspects as well as in general.

Preparation A

Linkers of Formula (IIa) Wherein S is Absent

Linkers of formula (IIa) wherein S is absent were prepared according to the following general procedures. In one method, an ester comprising groups Z and $R^4$ was condensed with $R^1R^2CH_2$ in the presence of a base, typically potassium tert-butoxide or potassium tert-pentoxide, to form an intermediate ketone which was reduced to the alcohol using sodium borohydride. This was then activated by reaction with triphosgene and pyridine to give the linker of formula (IIa) wherein X=Cl. This could be further converted to X=succinimidyloxy by reaction of the chloroformate with N-hydroxysuccinimide. In another method, the initial condensation was performed by first reacting $R^1R^2CH_2$ with a strong base such as butyllithium, lithium diisopropylamide, or a metalated hexamethyldisilazane, then treating the resulting $R^1R^2CH^-$ carbanion with the ester to provide the same ketone intermediate. Some specific examples follow:

(1) 4-Azido-1-cyano-3,3-dimethyl-2-butyl succinimidyl carbonate (Formula (I) Wherein n=1, $R^1$=CN, $R^2$=H, $R^4$=CH<sub></sub>, Z=N<sub></sub>, and X=succinimidyloxy)

A 1 M solution of potassium tert-butoxide in THF (3.5 mL, 3.5 mmol) was added to a solution of methyl 3-azido-2,2-dimethylpropionate (prepared according to Kim, Synthetic Communications; 300 mg, 1.9 mmol) and acetonitrile (0.365 mL, 7.0 mmol) in 7 mL of THF at −30° C. The mixture was stirred for 30 min at −30° C., then allowed to warm to ambient temperature over 1 h and stirred for an additional 30 min. The mixture was cooled on ice and quenched by addition of 6 N HCl (0.62 mL, 3.7 mmol), then partitioned between EtOAc and water. The aqueous phase was extracted 2× with EtOAc, and the combined organics were washed with brine, dried over MgSO$_4$, filtered, and concentrated to provide the crude ketone.

Sodium borohydride (33 mg, 0.88 mmol) was added to a solution of the crude ketone (300 mg, ca. 1.75 mmol) in 7 mL of methanol. The mixture was stirred for 15 min then quenched by addition of 6 N HCl (0.7 mL), and partitioned between EtOAc and water. The aqueous phase was extract 2× with EtOAc, and the combined organics were washed with brine, dried over MgSO$_4$, filtered, and concentrated to provide the crude alcohol. Purification on SiO$_2$ (20-40% EtOAc/hexane) provided 4-azido-1-cyano-3,3-dimethyl-2-butanol (142 mg, 0.85 mmol). $^1$H-NMR (CDCl$_3$, 300 MHz) δ 3.83-3.92 (m, 1H), 3.43 (d, J=12.1 Hz, 1H), 3.21 (d, J=12.1 Hz, 1H), 2.41-2.62 (m, 3H), 0.97 (s, 3H), and 0.96 (s, 3H).

Pyridine (136 uL, 1.7 mmol) was added dropwise to a solution of 4-azido-1-cyano-3,3-dimethyl-2-butanol (142 mg, 0.85 mmol) and triphosgene (425 mg, 1.44 mmol) in 8 mL of THF cooled on ice. The resulting suspension was allowed to warm to ambient temperature and stirred for 15 min, then filtered and concentrated to provide the crude chloroformate. This was dissolved in 8 mL of THF, cooled on ice, and treated with N-hydroxysuccinimide (291 mg, 2.5 mmol) and pyridine (204 uL, 2.53 mmol). The resulting suspension was allowed to warm to ambient temperature and stirred for 15 min, then partitioned between EtOAc and 5% KHSO$_4$. The aqueous phase was extract 2× with EtOAc, and the combined organics were washed with brine, dried over MgSO$_4$, filtered, and concentrated to provide the crude succinimidyl carbonate. Purification on SiO$_2$ (20-40% EtOAc/hexane) provided 4-azido-1-cyano-3,3-dimethyl-2-butyl succinimidyl carbonate (174 mg, 0.56 mmol). $^1$H-NMR (CDCl$_3$, 300 MHz) δ 5.03 (dd, J=7.0, 5.1, 1H), 3.27-3.41 (m, 6H), 3.43 (d, J=12.1 Hz, 1H), 3.21 (d, J=12.1 Hz, 1H), 2.41-2.62 (m, 3H), 0.97 (s, 3H), and 0.96 (s, 3H).

(2) 4-Azido-1-((N,N-dimethylamino)sulfonyl)-3,3-dimethyl-2-butyl succinimidyl carbonate (Formula (I) Wherein n=1, $R^1$=SO$_2$N(CH). $R^2$=H, $R^4$=CH<sub></sub>, Z=Ns and X=succinimidyloxy)

A 1.43 M solution of n-butyllithium in hexane (70 mL, 100 mmol) was added to a stirred solution of N,N-dimethyl methanesulfonamide (12.33 g, 100 mmol) in 200 mL of anhydrous THF kept at −50° C. under inert atmosphere. The mixture was allowed to warm to −20° C. over 1 h, then recooled to −50° C. before adding methyl 3-azido-2,2,-dimethylpropionate (prepared according to Kim, Synthetic Communications; 7.70 g, 50 mmol). The mixture was allowed to warm to +10° C. over 2 h, then quenched with 20 mL of 6 N HCl. The mixture was diluted with methyl t-butyl ether (MTBE, 200 mL), washed 2×100 mL of water and 1×100 mL of brine, dried over MgSO$_4$, filtered, and concentrated to yield 14.05 g of crude ketone product. Chromatography on SiO$_2$ (220 g) using a step gradient of 0, 20, 30, 40, and 50% EtOAc/hexane yielded purified 4-azido-1-((N,N-dimethylamino)sulfonyl)-3,3-dimethyl-2-butanone (10.65 g, 86%) as a crystalline solid.

The above ketone was dissolved in 200 mL of methanol, cooled on ice, and treated with sodium borohydride (0.96 g, 25 mmol) for 15 min before quenching with 4 mL of 6 N HCl and concentrating. The resulting slurry was diluted with methyl t-butyl ether (MTBE, 200 mL), washed 1×100 mL of water and 1×100 mL of brine, dried over MgSO$_4$, filtered, and concentrated to yield 10.0 g of crystalline 4-azido-1-((N,N-dimethylamino)sulfonyl)-3,3-dimethyl-2-butanol.

Pyridine (10.6 mL, 132 mmol) was added over 10 min to a stirred mixture of N-hydroxysuccinimide (6.90 g, 60 mmol) and triphosgene (5.93 g, 20 mmol) in 250 mL of dichloromethane cooled on ice. The mixture was stirred for 15 min on ice, then allowed to warm to ambient temperature over 30 min. A solution of 4-azido-1-((N,N-dimethylamino) sulfonyl)-3,3-dimethyl-2-butanol (10.0 g, 40 mmol) in 20 mL of dichloromethane was added and the mixture was stirred an additional 1 h at ambient temperature. After cooling on ice, the mixture was treated with 100 mL of water and the phases were separated. The organic phase was washed 2× water, 1×5% KHSO$_4$, and 1× brine, dried over MgSO$_4$, filtered, and concentrated. The crude product was crystallized from 100 mL of 30% EtOAc/hexane, providing 4-azido-1-((N,N-dimethylamino)sulfonyl)-3,3-dimethyl-2-butyl succinimidyl carbonate (11.1 g, 71%) as a white crystalline solid.

(3) Additional Compounds of Formula (I) Prepared According to these Procedures Include 4-Azido-1-(methylsulfonyl)-3,3-dimethyl-2-butyl succinimidyl carbonate (Formula I wherein n=1, $R^1$=SO$_2$CH$_3$, $R^2$=H, $R^4$=CH$_3$, Z=N$_3$, and X=succinimidyloxy).

4-Azido-1-((4-methylpiperidinyl)sulfonyl)-3,3-dimethyl-2-butyl succinimidyl carbonate (Formula I wherein n=1, $R^1$=SO$_2$N(CH$_2$CH$_2$)$_2$CHCH$_3$, $R^2$=H, $R^4$=CH$_3$, Z=N$_3$, and X=succinimidyloxy). LC/MS shows [M+H]$^+$=446.15.

4-Azido-1-(phenylsulfonyl)-3,3-dimethyl-2-butyl succinimidyl carbonate (Formula I wherein n=1, $R^1$=SO$_2$Ph, $R^2$=H, $R^4$=CH$_3$, Z=N$_3$, and X=succinimidyloxy).

4-Azido-1-(4-chlorophenylsulfonyl)-3,3-dimethyl-2-butyl succinimidyl carbonate (Formula I wherein n=1, $R^1$=SO$_2$PhCl, $R^2$=H, $R^4$=CH$_3$, Z=N$_3$, and X=succinimidyloxy).

4-Azido-1-(4-morpholinosulfonyl)-3,3-dimethyl-2-butyl succinimidyl carbonate (Formula I wherein n=1, $R^1$=SO$_2$N(CH$_2$CH$_2$)$_2$0, $R^2$=H, $R^4$=CH$_3$, Z=N$_3$, and X=succinimidyloxy).

4-Azido-1-(isopropylsulfonyl)-3,3-dimethyl-2-butyl succinimidyl carbonate (Formula I wherein n=1, $R^1$=SO$_2$CH(CH$_3$)$_2$, $R^2$=H, $R^4$=CH$_3$, Z=N$_3$, and X=succinimidyloxy).

4-Azido-1-((N-ethyl-N-methylamino)sulfonyl)-3,3-dimethyl-2-butyl succinimidyl carbonate (Formula I wherein n=1, $R^1$=SO$_2$N(CH$_3$)(CH$_2$CH$_3$), $R^2$=H, $R^4$=CH$_3$, Z=N$_3$, and X=succinimidyloxy).

4-Azido-1-((N,N-bis(2-methoxyethyl)aminosulfonyl)-3,3-dimethyl-2-butyl succinimidyl carbonate (Formula I wherein n=1, $R^1$=SO$_2$N(CH$_2$CH$_2$OCH$_3$)$_2$, $R^2$=H, $R^4$=CH$_3$, Z=N$_3$, and X=succinimidyloxy).

4-Azido-1-(4-methylphenylsulfonyl)-3,3-dimethyl-2-butyl succinimidyl carbonate (Formula I wherein n=1, $R^1$=SO$_2$PhCH$_3$, $R^2$=H, $R^4$=CH$_3$, Z=N$_3$, and X=succinimidyloxy).

4-(tert-butoxycarbonyl)amino-1-(methylsulfonyl)-3,3-di-methyl-2-butyl succinimidyl carbonate (Formula I wherein n=1, $R^1$=SO$_2$CH$_3$, $R^2$=H, $R^4$=CH$_3$, Z=NH-Boc, and X=succinimidyloxy).

4-(tert-butoxycarbonyl)amino-1-cyano-3,3-dimethyl-2-butyl succinimidyl carbonate (Formula I wherein n=1, $R^1$=SO$_2$CH$_3$, $R^2$=H, $R^4$=CH$_3$, Z=NH-Boc, and X=succinimidyloxy).

Compounds of formula (I) wherein S is absent and each $R^4$ is H were also prepared according to Sand et al., Proc. Natl. Acad. Sci. USA 2012, 109(16): 6211-6.

Preparation B

Linkers of Formula (IIa)

Wherein S=(CH$_2$CH$_2$O)$_h$(CH$_2$)$_g$C(O)NH and X=NH(CH$_2$CH$_2$O)$_p$(CH$_2$)$_{(m-1)}$CHO Linkers of formula (IIa) wherein S=(CH$_2$CH$_2$O)$_h$ (CH$_2$)$_g$C(O)NH and X=NH(CH$_2$CH$_2$O)$_p$(CH$_2$)$_{(m-1)}$CHO were prepared as follows. In one method, a linker of formula (IIa) wherein Z is azide, S is absent, and X=succinimidyloxy was reacted with amine-acetal H$_2$N—(CH$_2$)$_{m-1}$CH(OR)$_2$ wherein R is alkyl to give the azido carbamate acetal. Reduction of the azide group to an amine, either by catalytic hydrogenolysis over a palladium catalyst or by Staudinger reduction with trimethylphosphine in the presence of water, was followed by addition of an spacer-succinimidyl ester Z—(CH$_2$CH$_2$O)$_h$(CH$_2$)$_g$C(O)OSu to give the linker in its acetal-protected form. Hydrolysis of the acetal under acidic conditions then provided the linker of formula (IIa) wherein S=(CH$_2$CH$_2$O)$_h$(CH$_2$)$_g$C(O)NH, and X=NH(CH$_2$CH$_2$O)$_p$ (CH$_2$)$_{(m-1)}$CHO. Specific examples follow:

7-(15-Azido-4,7,10,13-tetraoxapentadecanamido)-1-(4-phenylsulfonyl)-2-heptyl N-(3-oxypropyl) carbamate (Formula IIa Wherein Z=Ns, S=(CH$_2$CH$_2$O)$_4$(CH$_2$)$_2$C(O)NH, n=5, $R^1$=(4-methylphenyl)SO$_2$, $R^2$=H, each $R^4$=H, and X=NH (CH$_2$)$_2$CHO))

-continued (1) 7-Azido-1-(4-methylphenylsulfonyl)-2-heptyl N-(3,3-diethoxypropyl) carbamate. 7-Azido-1-(4-methylphenylsulfonyl)-2-heptyl succinimidyl carbonate (125 mg, 277 µmol, 50 mM final concentration) (Santi et al., Proc. Natl. Acad. Sci. USA 2012, 109(16): 6211-6) was dissolved in 5.5 mL of MeCN, and 1-amino-3,3-diethoxypropane (54 µL, 0.33 mmol, 60 mM final concentration) was added. The reaction mixture was stirred at ambient temperature. Within 15 min, the starting carbonate was completely consumed as judged by TLC. The reaction mixture was partitioned between 100 mL of 1:1 EtOAc:NaHCO₃ (sat aq). The aqueous layer was extracted with 40 mL of EtOAc. The combined organic layers were successively washed with water, KHSO₄ (5% aq), water and brine (1×30 mL each). The organic phase was separated, dried over MgSO₄, filtered and concentrated to provide 109 mg (81% crude) of the title compound as a colorless oil, which was used in its entirety in the next step without further purification. 1H NMR (300 MHz, CDCl₃) δ 7.76 (d, J=8.1 Hz, 2H), 7.33 (d, J=8.1 Hz, 2H), 5.04 (quin, J=6.8 Hz, 1H), 4.91 (t, J=5.4 Hz, 1H), 4.49 (t, J=5.2 Hz, 1H), 3.62 (m, 2H), 3.37-3.53 (m, 3H), 3.10-3.25 (m, 5H), 2.42 (s, 3H), 1.74 (q, J=5.8 Hz, 2H), 1.63 (br q, J=5.7 Hz, 2H), 1.52 (m, 2H), 1.30 (br m, 4H), 1.17 (td, J=7.0, 2.1 Hz, 6H).

LC-MS (m/z): calc, 529.2; obsd, 529.6 [M+HCO₂]⁻.

(2) 7-(15-Azido-4,7,10,13-tetraoxapentadecanamido)-1-(4-methylphenylsulfonyl)-2-heptyl N-(3,3-diethoxypropyl) carbamate. 7-Azido-1-(4-methylphenylsulfonyl)-2-heptyl N-(3,3-diethoxypropyl) carbamate (109 mg, 225 µmol, 0.1 M final concentration) was dissolved in 2.3 mL of absolute EtOH. Palladium on carbon (10%, activated, 109 mg) was added. The reaction flask was sealed with a rubber septum then evacuated and backfilled with hydrogen gas (3×). The reaction mixture was vigorously stirred at ambient temperature under an atmosphere of H₂ (balloon). After 90 min, the starting material was completely consumed as judged by TLC. The reaction mixture was filtered through a short pipet plug of Celite, and the pad was washed with 10 mL of EtOH. The filtrate was concentrated to dryness to provide 90 mg of the intermediate amine as a colorless oil, which was used in its entirety in the next step without further purification.

Crude 7-amino-1-(4-methylphenylsulfonyl)-2-heptyl N-(3,3-diethoxypropyl) carbamate (90 mg, 0.20 mmol max, 0.1 M final concentration) was dissolved in 2.0 mL of MeCN. Succinimidyl 15-azido-4,7,10,13-tetraoxapentade-canoate (93 mg, 0.24 mmol, 0.12 M final concentration) and DIPEA (42 µL, 0.22 mmol) were added, and the reaction was stirred at ambient temperature and monitored by TLC. After 1 h, the reaction mixture was partitioned between 60 mL of 1:1 EtOAc:NaHCO₃ (sat aq). The organic layer was successively washed with water, citric acid (10% aq), water and brine (1×30 mL each). The organic phase was separated, dried over MgSO₄, filtered and concentrated to dryness. The crude product was purified on a 4 g SiliaSep column, eluting with a step-wise gradient of acetone in CH₂Cl₂: 0%, 10%, 20%, 30%, 40% and 50% (30 mL each). Clean product-containing fractions were combined and concentrated to provide the title compound (68 mg, 93 µmol, 41% two steps) as a colorless oil. 1H NMR (300 MHz, CDCl₃) δ 7.76 (d, J=8.3 Hz, 2H), 7.32 (d, J=8.1 Hz, 2H), 6.60 (br t, J=5.8 Hz, 1H), 4.95-5.08 (m, 2H), 4.50 (br t, J=4.9 Hz, 1H), 3.56-3.74 (m, 18H), 3.40-3.52 (m, 3H), 3.36 (t, J=5.1 Hz, 2H), 3.10-3.26 (m, 5H), 2.44 (t, J=5.8 Hz, 2H, obscured), 2.42 (s, 3H), 1.74 (q, J=6.0 Hz, 2H), 1.62 (br s, 2H), 1.43 (br m, 2H), 1.26 (br s, 4H), 1.17 (td, J=7.0, 2.3 Hz, 6H).

LC-MS (m/z): calc, 776.4; obsd, 776.7 [M+HCO₂]⁻.

(3) 7-(15-Azido-4,7,10,13-tetraoxapentadecanamido)-1-(4-methylphenylsulfonyl)-2-heptyl N-(3-oxypropyl) carbamate. 7-(15-Azido-4,7,10,13-tetraoxapentadecanamido)-1-(4-methylphenylsulfonyl)-2-heptyl N-(3,3-diethoxypropyl) carbamate (68 mg, 93 µmol, 0.1 M final concentration) was dissolved in 0.62 mL of CHCl₃. Water and TFA (0.16 mL each) were successively added. The reaction mixture was vigorously stirred at ambient temperature. After 2 h, the starting acetal was completely consumed as judged by TLC. The reaction mixture was concentrated to dryness then purified on a 4 g SiliaSep column, eluting with a step-wise gradient of acetone in CH₂Cl₂: 0%, 15%, 30%, 45%, 60% and 75% (30 mL each). Clean product-containing fractions were combined and concentrated to provide the title compound (26 mg, 40 µmol, 43%) as a colorless oil. 1H NMR (300 MHz, CDCl₃) δ 9.78 (s, 1H), 7.78 (d, J=8.3 Hz, 2H), 7.36 (d, J=8.0 Hz, 2H), 6.60 (br s, 1H), 5.09 (m, 1H), 4.98 (t, J=6.0 Hz, 1H), 3.62-3.75 (m, 16H), 3.36-3.44 (m, 5H), 3.13-3.26 (m, 3H), 2.70 (t, J=5.7 Hz, 2H), 2.47 (t, J=5.7 Hz, 2H, obscured), 2.45 (s, 3H), 1.63 (br s, 2H), 1.46 (br t, J=6.6 Hz, 2H), 1.29 (m, 4H). LC-MS (m/z): calc, 656.3; obsd, 656.6 [M–H]⁻; calc, 702.3; obsd, 702.6 [M+HCO₂]⁻; calc, 734.3; obsd, 734.7 [M+CH₃OH+HCO₂]⁻.

In a second method, a linker of formula (IIa) wherein Z=Boc-amino, S=absent, and X═OH was carried through a similar sequence of steps, but wherein the Boc group was first removed under acidic treatment and the spacer-succinimidyl ester Z—(CH$_2$CH$_2$O)$_h$(CH$_2$)$_g$C(O)OSu was attached. The alcohol was then activated by reaction with triphosgene and pyridine, and the resulting chloroformate was reacted with amine-acetal H$_2$N—(CH$_2$)$_{m-1}$CH(OR)$_2$ wherein R is alkyl to give the acetal-protected linker. Hydrolysis of the acetal under acidic conditions then provided the linker of formula (IIa) wherein S=(CH$_2$CH$_2$O)$_h$(CH$_2$)$_g$C(O)NH, and X=NH(CH$_2$CH$_2$O)$_p$(CH$_2$)$_{(m-1)}$CHO. Specific examples follow:

then concentrated to dryness and loaded onto a 4 g SiliaSep silica gel column. Products were eluted with a step-wise gradient of acetone in CH$_2$Cl$_2$ (0%, 10%, 20%, 30%, acetone; 30 mL each step). Clean, product-containing fractions—as judged by C18 HPLC-were combined and concentrated to dryness. Residual volatiles were removed under high vacuum to provide the title compound (85 mg, 0.16 mmol, 80% two-step yield) as a colorless oil. C18 HPLC, purity was determined by ELSD: 98.2% (RV=9.12 mL).

1-Azido-18,18-dimethyl-20-phenylsulfonyl-15-oxo-3,6,9,12-tetraoxa-16-azaicosan-19-yl (3-oxopropyl) carbamate (formula Ha Wherein Z=Ns, S=(CH$_2$CH$_2$O)$_4$(CH$_2$)$_2$C(O)NH, n=1, R$^1$=PhenylSO$_2$, R$^2$=H, each R$^4$=methyl, and X=NH(CH$_2$)$_2$CHO Steps 1 and 2. 1-Azido-18,18-dimethyl-20-phenylsulfonyl-15-oxo-3,6,9,12-tetraoxa-16-aza-19-icosanol. Trifluoroacetic acid (1 mL) was added to a solution of 4-[(tert-butoxycarbonyl)amino]-1-phenylsulfonyl-3,3-dimethyl-2-butanol (124 mg of a 58% w/w mixture; 72 mg, 0.20 mmol, 0.1 M final concentration) in 1 mL of CH$_2$Cl$_2$. The reaction was stirred at ambient temperature and monitored by TLC (40% EtOAc in hexane, cerium molybdate stain). After 10 min, the starting material had been converted to a single, more polar spot by TLC. The reaction was concentrated to dryness, and residual volatiles were removed under high vacuum to provide the intermediate amine as a white film. The intermediate was dissolved in 1.8 mL of MeCN, and DIPEA (0.17 mL, 1.0 mmol) was added. Neat azido-PEG$_4$-OSu (78 mg, 0.2 mmol) was added. The reaction was stirred at ambient temperature and monitored by C18 HPLC (ELSD). Azido-PEG$_4$-OSu was fully converted to a single, faster moving HPLC peak within 5 min. The reaction was Step 3. 1-Azido-18,18-dimethyl-20-phenylsulfonyl-15-oxo-3,6,9,12-tetraoxa-16-azaicosan-19-yl (3,3-diethoxypropyl)carbamate. N-Hydroxysuccinimide (92 mg, 0.80 mmol) was added to a solution of triphosgene (0.24 g, 0.80 mmol) in 8.0 mL of anhydrous THF under N$_2$. Pyridine (77 µL, 0.96 mmol) was added dropwise, and a white precipitate immediately formed. The suspension was stirred at ambient temperature for 15 min then filtered through a cotton plug. The filtrate was concentrated to dryness, and re-dissolved in 1.6 mL of anhydrous THF. A solution of 1-azido-18,18-dimethyl-20-phenylsulfonyl-15-oxo-3,6,9,12-tetraoxa-16-aza-19-icosanol (86 mg, 0.16 mmol, 0.1 M) in 1 mL of anhydrous THF was added. The reaction was stirred at ambient temperature and monitored by C18 HPLC (ELSD). After 1 h, the starting alcohol had been consumed. The reaction mixture was partitioned between 50 mL of 1:1 EtOAc:KHSO$_4$ (5% aq). The layers were separated, and the organic phase was successively washed with KHSO$_4$ (5% aq), water, NaHCO$_3$ (sat aq) and brine (25 mL each). The washed organic phase was dried over MgSO$_4$, filtered, and concentrated by rotary evaporation. The crude succinimidyl carbonate was dissolved in 1.6 mL of anhydrous THF, and 1-amino-3,3-diethoxypropane (86 µL, 0.53 mmol) was added. The reaction was stirred at ambient temperature and monitored by C18 HPLC (ELSD). After 25 min, the succinimidyl carbonate had been converted to two, slower-eluting product peaks. The reaction mixture was partitioned between 30 mL of 1:1 EtOAc:sodium acetate (0.2M, pH 5.0). The layers were separated, and the organic phase was successively washed with water, and brine (15 mL each). The washed organic phase was dried over $MgSO_4$, filtered, and concentrated by rotary evaporation. Residual volatiles were removed under high vacuum to provide the crude title compound (105 mg, 0.15 mmol, 94% crude two-step yield) as a yellow oil.

Step 4. 1-Azido-18,18-dimethyl-20-phenylsulfonyl-15-oxo-3,6,9,12-tetraoxa-16-azaicosan-19-yl (3-oxopropyl)carbamate. Water (0.21 mL) and TFA (0.21 mL) were successively added to a solution of 1-azido-18,18-dimethyl-20-phenylsulfonyl-15-oxo-3,6,9,12-tetraoxa-16-azaicosan-19-yl (3,3-diethoxypropyl)carbamate (105 mg, 0.15 mmol, 0.1 M final concentration) in 1.1 mL of $CH_2Cl_2$. The reaction was stirred at ambient temperature and monitored by C18 HPLC (ELSD). After 10 min, the reaction was judged to be complete. The mixture was concentrated to dryness. The concentrate was loaded onto a SiliaSep 4 g silica gel column, and products were eluted with a stepwise gradient of acetone in $CH_2Cl_2$ (0%, 20%, 40%, 60% acetone; 30 mL each step). Fractions were analyzed by TLC (Cerium molybdate stain). Clean product-containing fractions were combined and concentrated to dryness. Residual volatiles were removed under high vacuum to provide the title compound (34 mg, 54 μmol, 36% yield) as a colorless oil. The product was dissolved in 5.0 mL of Gibco $H_2O$ (0.01 M by mass). C18 HPLC, purity was determined by ELSD: 99.0% (RV=8.76 mL) 1-Azido-18,18-dimethyl-20-methylsulfonyl-15-oxo-3,6,9,12-tetraoxa-16-azaicosan-19-yl (3-oxopropyl)carbamate (formula IIa wherein Z=N₃, S=$(CH_2CH_2O)_4(CH_2)_2C(O)NH$, n=1, $R^1$=MeSO₂, $R^2$=H, each $R^4$=methyl, and X=NH$(CH_2)_2$CHO.

Step 3. 1-Azido-18,18-dimethyl-20-methylsulfonyl-15-oxo-3,6,9,12-tetraoxa-16-azaicosan-19-yl (3,3-diethoxypropyl)carbamate. N-Hydroxysuccinimide (98 mg, 0.85 mmol) was added to a solution of triphosgene (0.25 g, 0.85 mmol) in 8.5 mL of anhydrous THF under N₂. Pyridine (82 μL, 1.0 mmol) was added dropwise, and a white precipitate immediately formed. The suspension was stirred at ambient temperature for 15 min then filtered through a cotton plug. The filtrate was concentrated to dryness, and re-dissolved in 2 mL of anhydrous THF. A solution of 1-azido-18,18-dimethyl-20-methylsulfonyl-15-oxo-3,6,9,12-tetraoxa-16-aza-19-icosanol (80 mg, 0.17 mmol, 0.06 M) in 1 mL of anhydrous THF was added. The reaction was stirred at ambient temperature and monitored by C18 HPLC (ELSD). After 2 h, the starting alcohol had been consumed. The reaction mixture was partitioned between 50 mL of 1:1 EtOAc:KHSO₄ (5% aq). The layers were separated, and the washed organic phase was successively washed with KHSO₄ (5% aq), water, NaHCO₃ (sat aq) and brine (25 mL each). The organic phase was dried over $MgSO_4$, filtered, and concentrated by rotary evaporation. The crude succinimidyl carbonate (91 mg) was dissolved in 2 mL of anhydrous THF, and 1-amino-3,3-diethoxypropane (61 μL, 0.37 mmol) was added. The reaction was stirred at ambient temperature and monitored by C18 HPLC (ELSD). After 5 min, the succinimidyl carbonate had been converted to a single, slower-eluting product peak. The reaction mixture was partitioned between 30 mL of 1:1 EtOAc:sodium acetate (0.2M, pH 5.0). The layers were separated, and the organic phase was successively washed with water, and brine (15 mL each). The washed organic phase was dried over $MgSO_4$, filtered, and concentrated by rotary evaporation. Residual volatiles were removed under high vacuum to provide the crude title compound (61 mg, 95 μmol, 56% crude two-step yield) as a yellow oil.

Step 4. 1-Azido-18,18-dimethyl-20-methylsulfonyl-15-oxo-3,6,9,12-tetraoxa-16-azaicosan-19-yl (3-oxopropyl)carbamate. Water (135 μL) and TFA (135 μL) were successively added to a solution of 1-azido-18,18-dimethyl-20-methylsulfonyl-15-oxo-3,6,9,12-tetraoxa-16-azaicosan-19-yl (3,3-diethoxypropyl)carbamate (61 mg, 95 μmol, 0.1 M final concentration) in 0.68 mL of $CH_2Cl_2$. The reaction was stirred at ambient temperature and monitored by C18 HPLC (ELSD). After 25 min, the reaction was judged to be complete. The mixture was concentrated to dryness. The concentrate was loaded onto a SiliaSep 4 g silica gel column, and products were eluted with a stepwise gradient of acetone in $CH_2Cl_2$ (0%, 20%, 40%, 60%, 80%, 100% acetone; 30 mL each step). Fractions were analyzed by TLC (Cerium molybdate stain) and C18 HPLC. Clean product-containing fractions were combined and concentrated to dryness. Residual volatiles were removed under high vacuum to provide the title compound (12 mg, 21 μmol, 22% yield) as a colorless oil. After characterization, the product was dissolved in 2.0 mL of Gibco $H_2O$ (0.01 M by mass). C18 HPLC, purity was determined by ELSD: 91.3% (RV=5.60 mL)

(4) Additional compounds of formula (I) prepared according to these procedures include:

7-(15-Azido-4,7,10,13-tetraoxapentadecanamido)-1-(4-phenylsulfonyl)-2-heptyl N-(3-oxypropyl) carbamate (formula IIa wherein Z=N₃, S=$(CH_2CH_2O)_4(CH_2)_2C(O)NH$, n=5, $R^1$=PhSO₂, $R^2$=H, each $R^4$=H, and X=NH$(CH_2)_2$CHO)).

7-(15-Azido-4,7,10,13-tetraoxapentadecanamido)-1-(methylsulfonyl)-2-heptyl N-(3-oxypropyl) carbamate (formula IIa wherein Z=N₃, S=$(CH_2CH_2O)_4(CH_2)_2C(O)NH$, n=5, $R^1$=MeSO₂, $R^2$=H, each $R^4$=H, and X=NH$(CH_2)_2$CHO)).

7-(15-Azido-4,7,10,13-tetraoxapentadecanamido)-1-(morpholinosulfonyl)-2-heptyl N-(3-oxypropyl) carbamate (formula IIa wherein Z=N₃, S=$(CH_2CH_2O)_4(CH_2)_2C(O)$NH, n=5, $R^1$=O$(CH_2CH_2)_2$N—SO₂, $R^2$=H, each $R^4$=H, and X=NH$(CH_2)_2$CHO)).

5-(15-Azido-4,7,10,13-tetraoxapentadecanamido)-3,3-dimethyl-1-(thiomorpholinosulfonyl)-2-pentyl N-(3-oxypropyl) carbamate (formula IIa wherein Z=N₃, S=$(CH_2CH_2O)_4(CH_2)_2C(O)NH$, n=1, $R^1$=S$(CH_2CH_2)_2$NSO₂, $R^2$=H, each $R^4$=methyl, and X=NH$(CH_2)_2$CHO).

Example 1

Preparation and Activity of IL-2[N88R,C125S]

IL-2[N88R,C125S] was prepared by expression in HEK cells. Cell-based receptor binding assays were performed to evaluate the activity of the mutein against the high-affinity αβγ trimeric (T_reg) and intermediate affinity βγ dimeric (T_eff) forms of the IL-2 receptor (Table 1). The mutein binds only 6-fold poorer than IL-2 to the IL-2Rαβγ but about 900-fold poorer to the IL-2Rβγ. Importantly, the mutein is over 3,000 fold more selective for IL-2Rαβγ vs IL-2Rβγ.

A U2OS cell-based assay kit for IL-2Rαβγ binding was performed according the manufacturer's instructions (DiscoverX, Part #93-1003E3CP0). Cells were plated at 100 μL (~10,000 cells/well) in 96 well assay plates and grown for 24 hours at 37° C., 5% $CO_2$. Cells were then treated for 6 hours at 37° C., 5% $CO_2$ with dilution series of either WT IL-2, IL-2 N88R, C125S, or IL-2 N88R, C125S released from microspheres at pH 9.4. Eleven WT IL-2 concentrations were assayed between 2 pg/mL-100 ng/mL (0.1 pM-6 nM). Eleven IL-2 N88R, C125S and released IL-2 N88R, C125S concentrations were assayed between 200 pg/mL-10 μg/mL (10 μM-600 nM). Treated cells were incubated with chemiluminescent substrate for 1 hour at ambient temperature in the dark, then luminescence was read with a Spectramax i3 plate reader with 250 ms integration time.

A U2OS cell-based assay kit for IL-2Rβγ binding was performed according the manufacturer's instructions (DiscoverX, Part #93-0998E3CP5). Cells were plated at 50 μL (~5,000 cells/well) in 96 well assay plates and grown for 48 hours at 37° C., 5% $CO_2$. Cells were then treated for 6 hours at 37° C., 5% $CO_2$ with dilution series of either WT IL-2, IL-2 N88R, C125S, or IL-2 N88R, C125S released from microspheres at pH 9.4. Eleven WT IL-2 concentrations were assayed between 17 pg/mL-1 μg/mL (1 pM-61 nM). Eleven IL-2 N88R, C125S concentrations were assayed between 1.7 ng/mL-100 μg/mL (100 μM-6 μM). Eleven released remnant IL-2 N88R, C125S concentrations were assayed between 170 pg/mL-10 μg/mL (10 μM-600 nM). Treated cells were incubated with chemiluminescent substrate for 1 hour at ambient temperature in the dark, then luminescence was read with a Spectramax i3 plate reader with 250 ms integration time.

Figure 2:
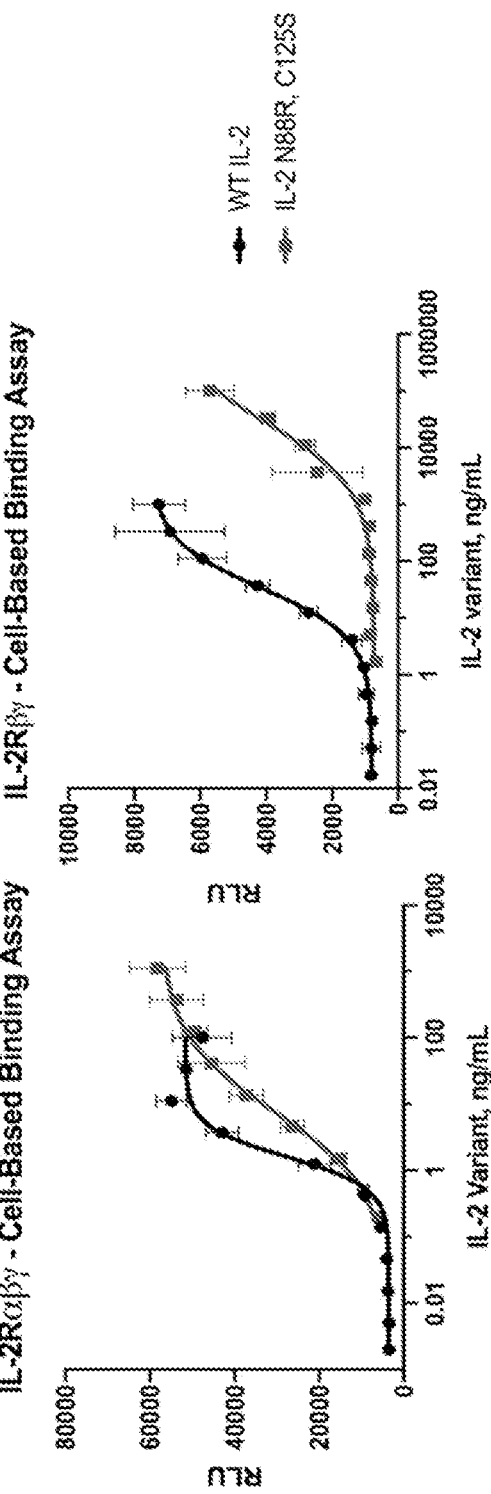
FIG. 2 shows the binding of IL-2[N88R,C125S] to cells containing αβγ and βγ receptors.

The results of these determinations are shown in FIG. 2 and Table 1.

TABLE 1

| Binding of IL-2 and IL-2N88R, C125S to cells containing αβγ and βγ receptors. | | | |
|---|---|---|---|
| | αβγ EC50, nM | βγ EC50, nM | Fold-change |
| WT IL-2 | 0.10 | 2.0 | 21 |
| IL-2 N88R, C125S | 0.55 | 1,849 | 3367 |
| Fold-change | 6 | 918 | |

Example 2

Figure 3:
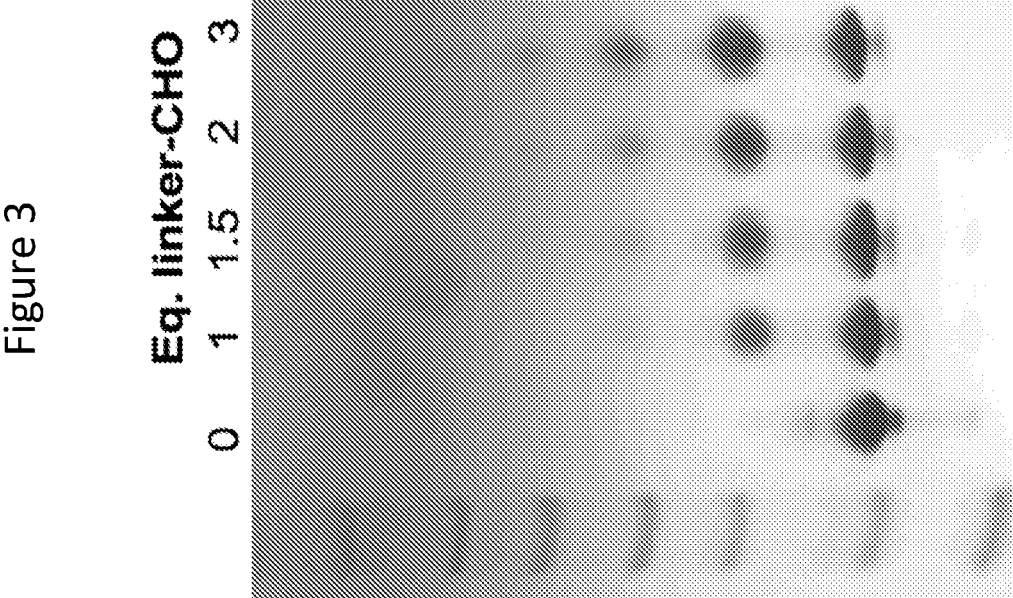
FIG. 3 shows an SDS-PAGE gel with bands corresponding to linker-protein products from reductive alkylation of IL-2[N88R,C125S].

Optimization of Cytokine Reductive Alkylation g=2, p=0, and m=3) in the presence of 10 mM $NaCNBH_3$. The reactions were analyzed by SDS-PAGE after reaction of the $N_3$ group with the PEG-cyclooctyne DBCO-$PEG_5$ kDa to induce a gel-shift due to PEG attachment. A ratio of 1.5:1 linker:protein was found to be optimal, giving a mix of 58:34:5:3 unmodified protein:single-linker-protein:double-linker protein:triple-linker protein (Table 2). FIG. 3 shows the resulting gel bands quantified with ImageJ. C125S (200 μM) was treated with 1, 1.5, 2 or 3 eq. linker-CHO (Mod=$MeSO_2$) and 10 mM $NaCNBH_3$ in 50 mM MES, 150 mM NaCl, pH 6.0 for 20 hours at ambient temperature.

TABLE 2

| Distribution of linker-protein products from reductive alkylation of IL-2 N88R, C125S | | | | |
|---|---|---|---|---|
| Eq linker | Unmodified | Single linker | Double linker | Triple linker |
| 1 | 66 | 30 | 4 | 0 |
| 1.5 | 58 | 34 | 5 | 3 |
| 2 | 52 | 35 | 9 | 4 |
| 3 | 43 | 38 | 15 | 4 |

Example 3

Preparation of Linker-Cytokines

IL-2[N88R,C125S] was attached to a releasable linker by one of two methods.

(1) random acylation. A mixture of cytokine (3.4 mL of 4.81 mg/mL, 1.00 umol) and 1.44 mL of 100 mM HEPES, pH 7.0, was mixed with 4-azido-3,3-dimethyl-1-(isopropylsulfonyl)-2-butyl succinimidyl carbonate [formula (II) wherein $R^1$=$^i$PrSO$_2$, $R^2$=H, $R^4$=Me, Z=$N_3$, n=1; S=absent; and X=succinimidyloxy] (156 uL of 10 mg/mL in acetonitrile, 4 umol) and kept for 20 h at 4° C. Hydroxylamine (0.55 mL of 1 M, pH 7.0) was added and kept for an additional 23 h at 4° C. The mixture was applied to a PD-10 column using 50 mM MES, pH 6.0, 0.05% Tween-20 to provide 1 umol of recovered protein by $OD_{280}$. Analysis (IIb)

IL-2
NaBH₃CN

Linker attachment was by reductive alkylation of the IL-2 N-terminal amino group. IL-2 N88R, C125S at 200 μM was treated with a concentration series of a linker reagent of formula (IIb) (i.e. a linker of formula (IIa) wherein $R^1$=$MeSO_2$, $R^2$ and $R^4$=H, S =$(CH_2CH_2O)_h(CH_2)_gC(O)$ NH, and X=$NH(CH_2CH_2O)_p(CH_2)_{(m-1)}CHO$, wherein h=4, by SDS-PAGE indicated formation of a 57:31:6:6 mixture of unmodified: 1 linker: 2 linker: 3+ linkers.

(2) reductive alkylation. Reductive alkylation was performed using the methods described in Schneider et al., Bioconjugate Chem (2016) 27: 2534-9 (incorporated herein by reference). To a solution of IL-2 N88R,C125S (250 μM final conc., 1.25 µmol, 20.5 mg) in 4.25 mL of 50 mM MES, 150 mM NaCl pH 6.0 (reaction buffer) at 0° C., a solution of O-7-[(15-azido-13,10,7,4-tetraoxapentadecanoyl)amino]-1-(methylsulfonyl)-2-heptyl N-3-oxapropylcarbamate [formula (II) wherein $R^1$=MeSO$_2$, $R^2$=H, $R^4$=H, Z=N$_3$, S=(CH$_2$CH$_2$O)$_4$CH$_2$CH$_2$CONH); n=4; and X=(CH$_2$)$_2$CHO] (375 µM final conc., 1.9 µmol, 0.9 mg, 0.27 mL) in 20 mM NaOAC pH 5.0, and NaCNBH$_3$ (10 mM final conc., 1 µmol, 0.5 µL) in reaction buffer was added. The reaction went for 22 hours at ambient temperature in the dark. Excess reagents were removed using PD-10 columns equilibrated in 20 mM MES, 150 mM NaCl, 0.05% tween-20, pH 6.0. After concentration with an Amicon Ultra 10,000 MW cutoff concentrator, 1.85 mL at 600 µM (by A280)—1.1 µmol, 89%—total peptide was recovered of linker-N-terminal aminopropyl-IL-2 [N88R,C125S].

Example 4

Preparation of IL2- and [aminopropyl]-IL2-Releasing Hydrogel Micropheres

Microsphere activation: PEG hydrogel microspheres of formula (IV) (prepared according to Henise et al., Engineering Reports (2020) https://doi.org/10.1002/eng2.12091) were used wherein $P^1$ and $P^2$ were 20-kDa 4-armed PEGs; Z* was the triazole from Z=N$_3$ and Z'=5-hydroxycyclooctyne; n=4; $R^{11}$=CN; $R^{12}$=H; each $R^{14}$=H; B=NH$_2$; x=4; y=0; z=0; and r=4. These were activated to formula (IV) wherein B=NH—CO—O-(4-cyclooctynyl) as follows. To a suspension of 1.3 g of a slurry of microspheres wherein B=NH$_2$ (4.2 µmol NH$_2$) in MeCN in a 15 mL conical tube was added a solution of 4-cyclooctynyl succinimidyl carbonate (5 µmol, 1.2 eq) in 1 mL MeCN and N,N-diisopropylethylamine (17 µmol, 4 eq) in 1 mL MeCN. The reaction was rotated end-over-end for 6 hours at ambient temperature. The slurry was washed with 4×12 mL MeCN, then 4×12 mL 20 mM MES, 150 mM NaCl, 0.05% tween-20, pH 6.0.

Using the same methods, microspheres of formula (IV) wherein B=NH$_2$ were activated to formula (IV) wherein B=(1R,8S,9s)-bicyclo[6.1.0]non-4-yn-9-ylmethoxy-CO—NH by reaction with BCN-OSu ((1R,8S,9s)-bicyclo[6.1.0] non-4-yn-9-ylmethyl succinimidyl carbonate) in place of 4-cyclooctynyl succinimidyl carbonate.

To attach the linker-cytokine, a suspension of 2 g of a slurry of activated microspheres (4.2 µmol 5HCO) in 20 mM MES, 150 mM NaCl, 0.05% tween-20, pH 6.0 in a 15 mL conical tube was mixed with a solution of 18.3 mg (1.1 nmol) of linker-AP-IL-2 N88R, C125S (37% linker-IL-2 by gel shift assay, Example 3) in 1.9 mL of the same buffer. The mixture was incubated at 37° C. for 23 hours with orbital shaking at 250 rpm. The slurry was washed with 8×12 mL of the above buffer, followed by 4×6 mL of 20 mM MES, 250 mM NaCl, 0.05% tween-20, pH 6.0. The total loading of the microspheres was 102 nmol IL-2 N88R, C125S gm$^{-1}$ of slurry as determined by A280 ($\varepsilon_{280}$=10,095 M$^{-1}$ cm$^{-1}$) of AP-IL-2 released from 29-32 mg aliquots of slurry dissolved in 9 volumes of 50 mM NaOH.

PEG hydrogel microspheres were loaded with linker-IL-2 prepared by random acylation (Example 3) in the same manner, giving the insoluble conjugate loaded to 0.11 mM with protein having SEQ ID No: 3.

Example 5

In Vitro Release Kinetics

Kinetics of β-elimination were determined under accelerated release conditions using 257 mg of the microsphere- IL-2 mutein slurry of Example 4 in 257 µL of 250 mM NaBorate, 0.05% (v/v) tween-20, pH 9.4 at 37° C. in an Eppendorf tube. At time intervals, samples were removed from the 37° C. water bath, centrifuged at 21,000×g for 1 minute, and $A_{280}$ of 100 µL of supernatant was measured in a cuvette-based UV/Vis spectrophotometer. The assayed supernatant was returned to the microsphere-containing tube after measurement, and incubation at 37° C. continued. The release rate was calculated by fitting the released A280 vs time to the first-order rate equation in Graphpad Prism. Knowing that the β-elimination is first-order in hydroxide ion, rates were calculated at pH 7.4 as $k_{pH\ 7.4}$=$k_{pH}$× $10^{(pH-7.4)}$. The release profile for IL-2 [N88R,C125S] from the random acylation conjugate of Example 2 was biphasic, with half-lives of 0.4 and 41 h at pH 9.4, corresponding to 40 and 4100 h at pH 7.4. The release profile for AP-IL-2 [N88R,C125S] from the reductive alkylation conjugate of Example 2 was monophasic with a half-life of 11 h at pH 9.0, corresponding to 440 h at pH 7.4.

Example 6

Figure 4:
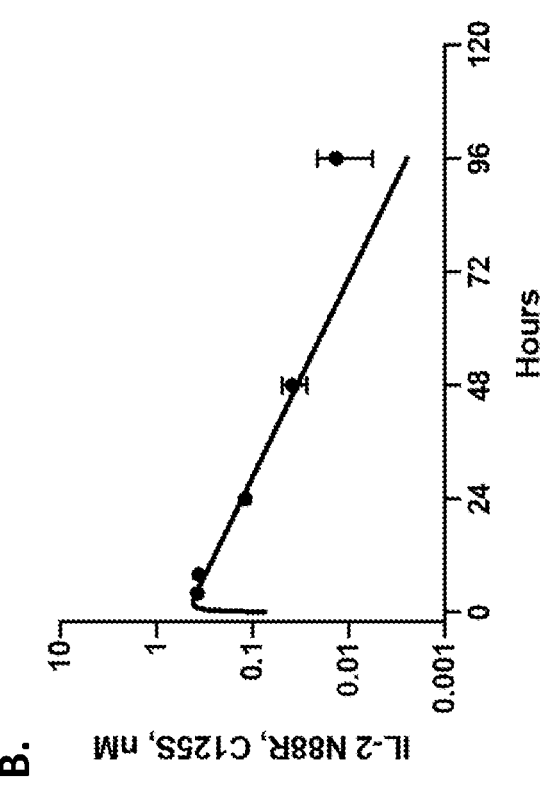
FIG. 4 shows the C vs t plot of plasma IL2[N88R] in rat after treatment with microsphere-IL2-N88R.
Figure 4:
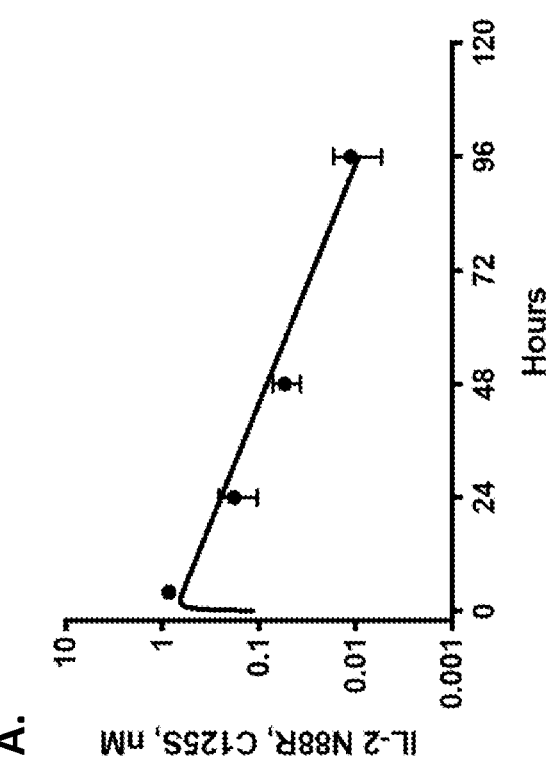

Pharmacokinetics of IL-2[N88R,C125S] Released from Hydrogel Microspheres in the Rat Syringes (0.5 mL 29 gauge, fixed needle, BD) were filled under sterile conditions with an average of 50 mg or 300 mg of microsphere-IL-2 slurry of Example 4 (5 nmol or 30 nmol IL-2 [N88R,C125S]) in a dosing buffer consisting of 20 mM MES, 250 mM NaCl, 0.05% (w/v) tween-20, pH 6.0. The contents of each syringe were administered s.c. in the flank of four cannulated male Sprague Dawley rats, average weight 250 g. Blood samples (200 µL) were drawn at 0, 4, 8, 24, 48, 96, 168, 240, 336, 408, 504, 576 and 672 hours; plasma was collected, protease inhibitors were added, and the samples were frozen at −80° C. until analysis. Using the microsphere conjugates of Example 2, IL-2 (or NH$_2$(CH$_2$)$_3$-IL-2, "AP-IL2") was observed in the plasma for 96 h post-administration, as shown in FIG. 4.

Example 7

Pharmacodynamics of IL2 and IL2[N88R,C125S] in Mice

Pharmacodynamics of the free IL-2[N88R,C125S] was compared to that of native IL-2 in NOD (non-obese diabetic) mice. Three groups of three NOD mice each were given daily injections of either PBS vehicle, Proleukin (25,000 units, 63 µg) or IL-2[N88R,C125S](25,000 units, 63 µg) for five consecutive days. Mice were sacrificed 2 hours after the last injection and the spleen and pancreas were harvested for flow cytometry analysis to measure changes in total number of T-cells and their differentiation in the spleen and islets.

Figure 5:
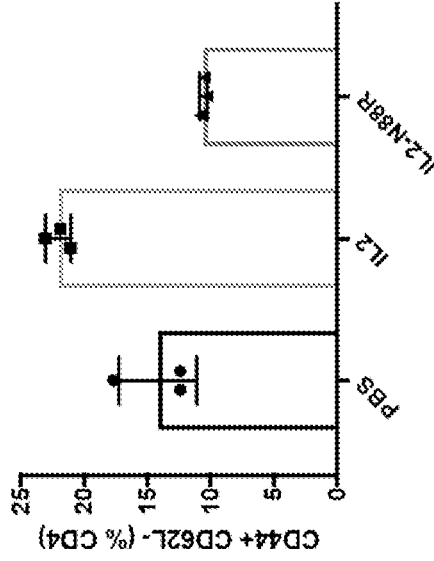
FIG. 5 shows the pharmacodynamics of IL-2[N88R, C125S] in the spleen. Left: Percentage of CD4+ effector/memory T-cells; Right: Percentage of CD8+ effector/memory T-cells.

IL-2[N88R,C125S] had little to no effect on the CD4$^+$ and CD8$^+$ effector/memory T-cells in the spleen, where as an increase in both T-cell populations increased with native IL-2 (FIG. 5).

NOD mice were given daily injections of PBS vehicle, Proleukin (25,000 units) or IL-2[N88R,C125S] (25,000 units) and sacrificed two hours after the last injection on the fifth day. The pharmacodynamics of IL-2[N88R,C125S] in the spleen is shown in FIG. 5.

Figure 6:
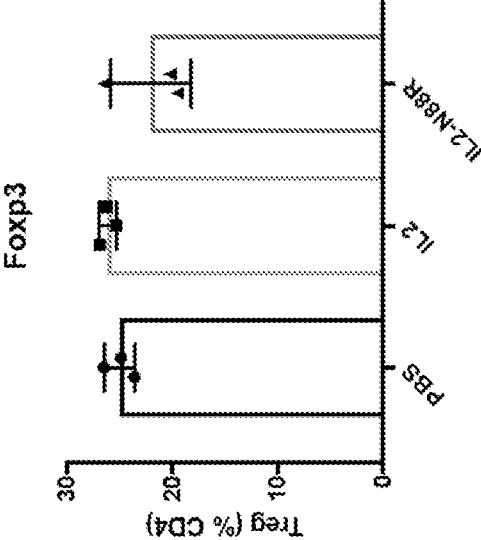
FIG. 6 shows the pharmacodynamics of IL-2[N88R, C125S] in the islets. Top left: Percentage of Foxp3+CD4+ T-cells; Top right: Percentage of CD4+; Bottom left: Percentage CD8+; Bottom right: Innate lymphoid cells. NOD mice were given daily injections of PBS vehicle, Proleukin (25000 units) or IL-2[N88R,C125S] (25000 units) and sacrificed two hours after the last injection on the fifth day.
Figure 6:
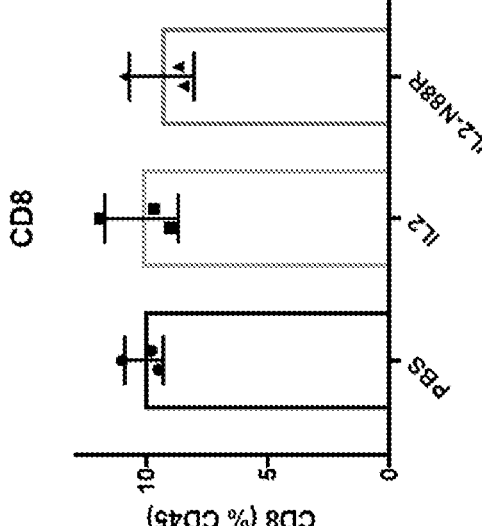

Both native IL-2 and the IL-2[N88R,C125S] had little to no effect on the T-cells in the islets compared to the PBS vehicle (FIG. 6). It should be noted that the overall number of islets decreased when the mice were treated with IL-2 [N88R,C125S].

NOD mice were given daily injections of PBS vehicle, Proleukin (25000 units) or IL-2[N88R,C125S] (25000 units) and sacrificed two hours after the last inject on the fifth day. The pharmacodynamics of IL-2[N88R,C125S] in the islets is shown in FIG. 6.

Example 8

Pharmacokinetics/Pharmacodynamics of [aminopropyl]-IL2[N88R,C125S] Released from Microsphere-IL-2[N88R,C125S] in Mice Three groups of six NOD mice were used to determine the PK/PD of [aminopropyl]-IL-2[N88R,C125S] released from the microsphere-IL-2[N88R,C125S] conjugate. The first group was given five daily injections of the free IL-2[N88R, C125S](25,000 units, 63 μg). The second group was administered a subcutaneous injection of empty microspheres, in which cyclooctynes were capped with $N3(CH_2CH_2O)_7H$. The third group was administered a single subcutaneous injection of the microsphere-IL-2[N88R,C125S] of Example 4 (0.5, 1, 5, 10 or 19 mg of protein/kg). Plasma, peripheral blood mononuclear cells (PBMCs) and organ tissues were prepared and analyzed according to the description in figure legends. Flow cytometric analysis of lymphocytes was performed to monitor changes in T-cell populations. The spleen and lymph nodes and islets were isolated and single cell suspensions were prepared. Surface-staining was performed following standard cell surface immunofluorescence staining for flow cytometry. Fixation and intracellular staining followed protocols from the eBioscience Foxp3/Transcription Factor Staining Buffer Set (ThermoFisher Scientific). Antibodies used were against CD3, CD4, CD8, CD25, CD44 CD45, and FoxP3; all were from commercial vendors. Stained single cell suspension were analyzed using a LSRII flow cytometer (BD Biosciences).

Figure 7:
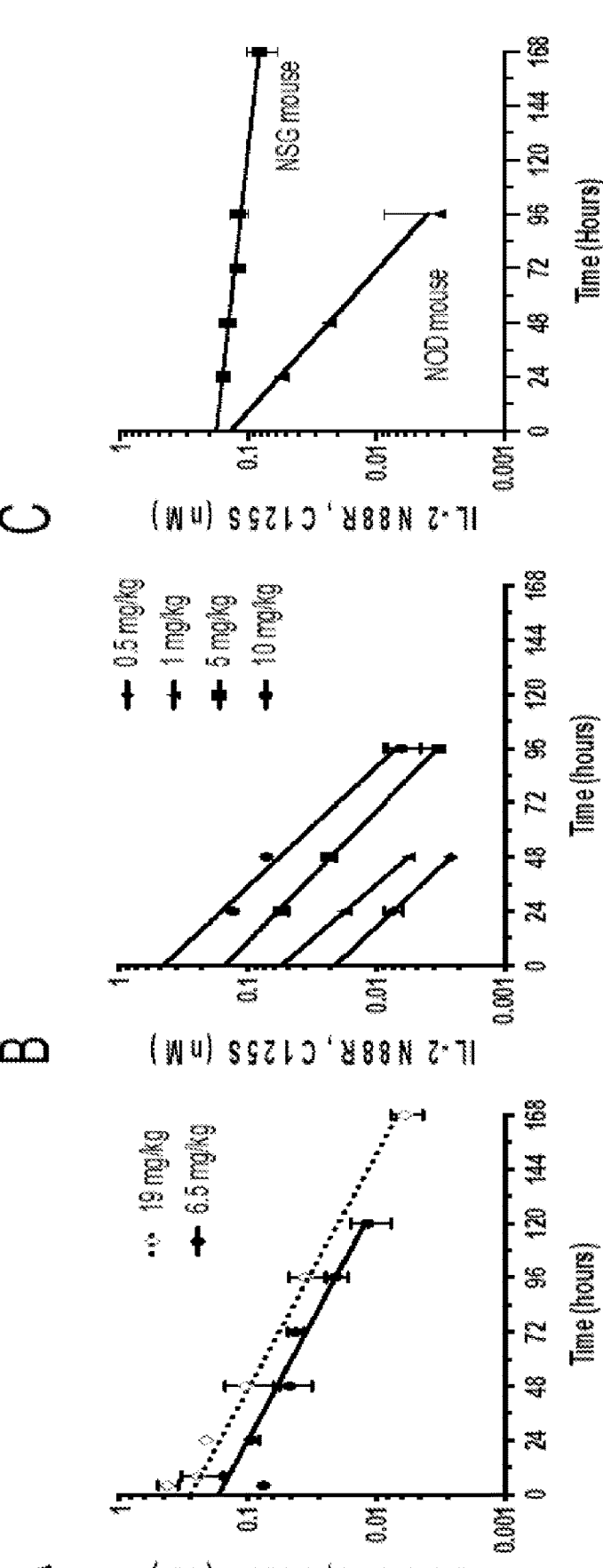
FIG. 7 shows the pharmacokinetics of [aminopropyl]-IL-2[N88R,C125S] released from microsphere-IL-2[N88R, C125S] ("MS-IL-2 mutein") in mice.

FIG. 7 shows the pharmacokinetics of [aminopropyl]-IL-2[N88R,C125S] released from microsphere-IL-2[N88R, C125S] ("MS-IL-2 mutein") in mice. Panel A: BALB/c mice (n=6) were given a single s.c. injection containing either 28 nmol (19 mg/kg) or 9.9 nmol (6.5 mg/kg) microsphere-IL-2[N88R,C125S] in the flank. A $t_{1/2}$ of 31 h was determined. Panel B: NOD mice (n=6) were dosed with microsphere-IL-2[N88R,C125S] in the flank. In both cases, plasma was analyzed using Thermofisher ELISA to quantify IL-2[N88R,C125S] concentration.

Treatment with the microsphere-IL-2[N88R,C125S] resulted in a massive expansion of Foxp3$^+$CD4$^+$ T-cells in both the spleen and PBMC. Nearly 70 and 55% of the T-cells in the spleen and PBMC, respectively, were Foxp3$^+$CD4$^+$ T-cells (FIG. 8). The percentage of CD8$^+$ T-cells also increased relative to the control. CD8+ cells increased from 11% to 25% in the spleen and from 15% to 60% in PBMCs.

FIG. 8A shows the expansion of Foxp3$^+$CD4$^+$ T-cells in the spleen and PBMCs. FIG. 8B shows the expansion of CD8$^+$ T-cells in the spleen and PBMCs. The percentage CD8+ cells found in the spleen and PBMCs were approximately 11% and 19% respectively. These percentages increased to approximately 25% and 60% respectively, when treated with the microsphere-IL-2[N88R,C125S]. NOD mice were administered IL2-mutein (QDx5, 25,000 units), a single injection of empty microspheres or microsphere-IL-2[N88R,C125S] (18 mg/kg). Mice were sacrificed 2 hours after the last dose on day 5.

To determine an effective dose that would expand the Foxp3$^+$CD4$^+$ Tcells population without the activation of CD8' cells, a dose titration study of microsphere-IL-2 [N88R,C125S] was performed. Four concentrations of the microsphere-IL-2[N88R,C125S](0.5 mg/kg, 1 mg/kg, 5 mg/kg and 10 mg/kg) were tested and the pharmacodynamics were monitored through PBMCs over two weeks. A dose dependent expansion of Foxp3$^+$CD4$^+$ T-cells was observed in PBMCs following a single injection of microsphere-IL-2[N88R,C125S]. Foxp3$^+$CD4$^+$ T-cell expansion peaked at four days and returned to baseline levels at day 14 for all doses (FIG. 9 A). Importantly, the percentage of CD8+ cells did not increase in any of the administered doses (FIG. 9 B).

FIG. 9A shows that microsphere-IL-2[N88R,C125S] preferentially expands Foxp3$^+$CD4$^+$ T-cells, and FIG. 9B shows that they avoid activation of CD8' cells (right) in NOD mice (n=3/dose group). As shown, Foxp3$^+$CD4$^+$ T-cell expansion peaked at day 4 for all doses and returned to baseline levels by day 14.

Example 9

Preparation of Linker-IL-15

The linker in Example 2 was conjugated to the N-terminus of IL-15 via reductive alkylation using $NaCNBH_3$ as described for IL-2 above. The reaction mixture contained IL-15 (30 μM), $N_3$—$PEG_4$-linker($MeSO_2$)—CHO (90 μM) and NaCNBH3 (10 mM) in 25 mM Na Phosphate, 250 mM NaCl pH 7.4. The reaction went for 24 hours at ambient temperature in the dark. Excess reagents were removed using a PD-10 column equilibrated in 20 mM Na citrate, 500 mM NaCl, 0.05% tween-20, pH 5.86. The desalted reaction mixture was concentrated using an Amicon Ultra 3,500 MW cutoff concentrator.

Small scale (2.25 nmol, 75 μL) reductive alkylation reactions varying the linker equivalents were performed with IL-15 to determine optimal reaction conditions. Initial reactions were performed using 1, 1.5 and 2 equivalents of $N_3$-$PEG_4$-L($MeSO_2$)—CHO linker and showed the addition of 1 linker to the protein in a 1:1 ratio (Data not shown). Subsequent reactions were performed with 1.5, 3 and 5 equivalents of linker to increase the conversion of the unmodified protein (FIG. 10 A). With 3 equivalents of linker, the reaction resulted in approximately 52% of IL-15 having only 1 linker attached to the protein and approximately 5% of IL-15 having two linkers attached (FIG. 10 B). Increasing the linker concentration to 5 equivalents resulted in only a small increase in single linker protein, but approximately 27% of the total protein had two or more linkers attached.

The progress of the reaction was determined by SDS-PAGE DBCO-$PEG_{5k}$ gel shift assay as shown in FIG. 10. Table 3 shows the percent IL-15 modified. Bands were quantified using ImageJ software. IL-15 (30 μM) was treated with 1.5, 3 or 5 equivalents linker-CHO (Mod=$MeSO_2$) and NaCNBH3 (10 mM) in 25 mM sodium phosphate 500 mM NaCl for 20 hours in the dark at ambient temperature.

TABLE 3

| | % IL-15 Modification | | | |
|---|---|---|---|---|
| Eq. Linker | Unmodified | 1 linker | 2 linkers | 3 linkers |
| 1.5 | 54 | 46 | 0 | 0 |
| 3 | 43 | 52 | 5 | 0 |
| 5 | 16 | 58 | 22 | 5 |

The optimized reaction condition using 3 equivalents of linker was used in large scale (0.93 µmol-1.08 µmol) reactions. Large scale reactions were performed two times.

Example 10

Preparation of Microsphere-IL-15

A slurry of BCN-activated microspheres (2.6 µmol BCN, Example 4) was washed five times (~35 mL) with 20 mM Na citrate, 500 mM NaCl, 0.05% tween-20, pH 5.86, in a sterile syringe. Linker-IL-15 (Example 9) (1 µmol total protein, containing approximately 50% alkylated IL-15) was added to the syringe through a sterile filter (0.22 µM). The mixture was rotated end-over end at ambient temperature for 18 hours. The slurry mixture was then washed 5 times with 20 mM Na citrate, 500 mM NaCl, 0.05% tween-20, pH 5.86. The unreacted BCN activated microspheres were capped with $N_3(CH_2CH_2O)_7H$ and subsequently washed an additional six times. The IL-15 concentration loaded on the microspheres (216-336 µM) was determined by A280 ($\varepsilon_{280}$=7240 $M^{-1}$ $cm^{-1}$) from IL-15 released from 5 mg aliquots of slurry dissolved in 4 volumes of 50 mM NaOH. The MS-IL-15 concentrations from three separate loadings were determined to be 336 nmol/mL 216 nmol/mL and 232 nmol/mL.

Example 11

Pharmacokinetics of IL-15 Released from Microsphere-IL-15

The microsphere-IL-15 slurry of Example 10 (275 nmol protein/mL) was diluted in 25 mM Na citrate buffer pH 5.9 containing 500 mM NaCl, 0.05% tween-20 and 1.25% (w/v) hyaluronic acid. For studies that required various doses of microsphere-IL15, serial dilutions were used obtain the desired microsphere-IL-15 concentration. In all cases, aseptic conditions were used to handle and prepare the microsphere conjugate. Syringes with fixed needles (27G) were backfilled with the conjugate (100 µL). The contents of the syringes were administered either s.c. or i.p. to normal, male C57BL/6J mice. Blood samples were drawn at −24, 4, 8, 24, 48, 96, 168 and 240 hours from alternating groups consisting of 3 mice each. HALT protease inhibitor cocktail (ThermoFisher Scientific) was added to all plasma samples prior to being frozen at −80° C. until analysis.

ELISAs for hIL-15 were performed according to the manufacturer's instructions (R&D Systems, hIL-15 Quantikine, Catalog #D1500) to determine the rhIL-15 plasma. Plasma samples were thawed on ice prior to dilution in the standard diluent provided by the manufacturer. The 4, 8, hour samples were diluted 50-fold, the 24 hour samples was diluted twenty-five fold, and the pre-bleed, 48, 96, 168 and 240 hour samples were diluted ten-fold. hIL-15 concentrations were plot as a function of time and fit using GraphPad Prism software.

For flow cytometry analysis, PMBCs were prepared and surface staining was performed to quantitate NK1.1, CD3, CD8, and CD44 expressing cells. Commercial FITC-, PE- or allophycocyanin-conjugated antibodies were used. Sample data were collected on a FACScan flow cytometer (BD Biosciences) and analyzed using FlowJo cytometry analysis software (TreeStar, Ashland, Oreg.).

Pharmacokinetics of [aminopropyl]-IL-15 released from the microsphere conjugate were measured in normal C57BL/6J mice. Mice were dosed with 2.4 nmol conjugated protein (200 µL injection). There was no significant change in the initial average mouse body weight (25.1±1.3 g) and final average mouse body weight (25.1±1.4 g). After approximately 120 hours, the observed concentration quickly decreases (FIG. 11). A one phase decay model fit of data through 120 results in a half-life of at least 200 hours. Data points from 120 h to 240 h fit to a one phase decay model resulted in a $t_{1/2}$ of 27 h. A second injection of MS-IL-15 (50 µg) increases the measured plasma IL-15 at 248 h to a similar concentration of the initial dose. A $t_{1/2}$ of 23 h is observed from 264 h to 360 h.

FIG. 11 shows the pharmacokinetics of [aminopropyl]-IL-15 released from MS-IL-15 in C57BL/6J mice. Normal, male C57BL/6J mice were dosed with MS-IL-15 (50 µg) at t=0 h and t=240 h. Plasma samples were prepared and analyzed using the human IL-15 Quantikine ELISA (R&D systems). Two distinct $t_{1/2}$ are observed through 240 h. A $t_{1/2}$ of at least 115 hour is observed through 120 hours followed by a second $t_{1/2}$ of 43 from 120 h to 240 h. A second injection of MS-IL15 (50 µg) was administered immediately after the 240 h blood draw (blue data).

FIG. 12 shows the dose-dependence of pharmacokinetics of [amino-propyl]-IL-15 released from microsphere-IL-15 in C57BL/6J mice. Normal, male C57BL/6J mice were dosed with MS-IL-15 (12.5, 25 or 50 µg). Plasma samples were prepared and analyzed using the human IL-15 Quantikine ELISA (R&D systems).

The administration route (i.e., s.c. and i.p.) did not alter the $t_{1/2}$ of the released [aminopropyl]-IL15 (FIG. 13). However, the $AUC_{ip}$ (25.2 nM*h) compared to the $AUC_{sc}$ (14.9 nM*h) was nearly two-fold higher. This may indicate an increased bioavailability or increased rate of absorption of the IL-15 from the intraperitoneal space.

FIG. 13 shows the pharmacokinetics of [aminopropyl]-IL-15 released from microsphere-IL-15 in C57BL/6J mice administered s.c. vs i.p. Normal, male C57BL/6J mice were administered MS-IL-15 (50 µg) either s.c. injection (black, ●) or i.p. injection (blue, ■). Plasma samples were prepared and analyzed using the human IL-15 Quantikine ELISA (R&D systems). A similar tin was observed for s.c. (115 h) and i.p. (129 h) administration through 120 h.

Example 12

Pharmacodynamics of [aminopropyl]-IL-15 Released from Microsphere-IL-15

Pharmacodynamics of [aminopropyl]-IL-15 released from the microsphere-IL-15 of Example 10 were measured in normal, male C57BL/6J mice (n=3/group) (FIG. 14). Mice were dosed with microsphere-IL-15 (2.5, 12.5, 25 or 50 µg conjugated protein) prepared in Example 10. PMBCs were prepared and surface stained for flow cytometry analysis of NK1.1, CD3, CD8, and CD44 expressing cells. Commercial FITC-, PE- or allophycocyanin-conjugated antibodies were used. Sample data were collected on a FACScan flow cytometer (BD Biosciences) and analyzed using FlowJo cytometry analysis software (TreeStar, Ashland, Oreg.). Clinical observations included no injection site reaction as well as no significant change in the initial average body weight (25.1±1.3 g) and final average body weight (25.1±1.4 g).

A single sc injection of the MS-IL-15 conjugate (12.5 µg, 25 µg or 50 µg) resulted in a dose dependent expansion of CD44$^{hi}$CD8$^+$ T cells in PBMCs. A two to four fold expansion of CD44$^{hi}$CD8$^+$ T cells peaked at 5 days post treatment. These cells remained elevated above the control group through 21 days (FIG. 14A). At 28 days, the mice administered the highest dose of MS-IL-15 (50 µg) still had CD44$^{hi}$CD8$^+$ T cells levels two-fold above the control group. There was no observed expansion of CD44$^{hi}$CD8$^+$ T cells from a single dose of native rhIL-15 (2.5 µg) or from an equivalent dose of MS-IL-15 (2.5 µg) over the duration of the experiment.

A dose dependent expansion of NK cells was also observed in PBMCs following a single s.c. injection the MS-IL-15 conjugate (FIG. 14B). An approximate 2-3 fold expansion of NK cells peaked between 5 and 7 days post treatment when MS-IL-15 (12.5 µg, 25 µg or 50 µg) was administered. The NK cells remained elevated between 14 and 21 days. Expansion of NK cells were not observed with a single dose of native rhIL-15 (2.5 µg) or from an equivalent dose of MS-IL-15 (2.5 µg).

Example 13

Preparation of Linker-RLI and Microsphere-RLI Conjugate

RLI (receptor-linked interleukin) is a fusion protein comprising IL-15 and the sushi-domain of the receptor α-subunit that acts as a super-agonist of the IL-15 receptor β/γ complex (Mortier et al., J. Biological Chem. 2006, 281: 1612-9; U.S. Pat. No. 10,358,488).

Small scale reductive alkylation reactions of RLI (10 nmol, 50 µL) varying the linker concentration were performed to determine optimal reaction conditions for stoichiometric linker addition. Initial reactions were performed using 1.5, 2, 3 and 5 equivalents of linker (IIb) of Example 2. Under the tested conditions, when 1.5 equivalents of linker were used, 44% of RLI was modified with one linker and 46% remained unmodified. It was determined that 2 equivalents of linker resulted in approximately 53% of the RLI having stoichiometric addition of the linker; 33% of the RLI was unmodified and 14% had more than one linker covalently bonded. Increasing the linker equivalence to 3 eq. resulted in an increase in the percentage of 2 linker additions (27%) as well as the formation of RLI containing 3 linkers (6%). These percentages increased even more in the presence of 5 equivalents of linker (FIG. 15).

TABLE 4

| | Unmodified | +1 linker | +2 linkers | +3 linkers |
|---|---|---|---|---|
| 1.5 eq. | 46% | 44% | 10% | — |
| 2.0 eq. | 33% | 53% | 14% | — |
| 3.0 eq. | 14% | 53% | 27% | 6% |
| 5.0 eq. | 5% | 48% | 28% | 19% |

The reductive alkylation of RLI was determined by SDS-PAGE DBCO-PEG$_{5K}$ gel shift assay. FIG. 15 shows the percent of RLI modified, as determined from the gel shift assay. Bands were quantified using ImageJ software. RLI (10 nmol) was treated with 1.5, 2, 3 or 5 equivalents linker-CHO (Mod=MeSO$_2$) and NaCNBH$_3$ (10 mM) in 25 mM MES 500 mM NaCl and 0.05% tween-20 for 20 hours at room temperature in the dark.

Using 2 equivalents of linker, large scale reductive alkylation reactions (800 nmol, 4 mL) were performed. The reductively alkylated RLI was then conjugated to BCN-activated microspheres (Example 4). To minimized oxidative processes EDTA (1 mM) and methionine (30 mM) were added to the reaction. Following the conjugation reaction, the microspheres were extensively washed with buffer (25 mM Na citrate, 500 mM NaCl, 0.05% tween-20, 30 mM methionine, pH 5.9) to remove non-covalently attached RLI. Small aliquots (~25 mg) of washed microspheres were digested in NaOH (50 mM) to determine the concentration of RLI covalently bound to the microspheres. The RLI concentration on the microspheres was determined to be 175 nmol/mL.

Example 14

Bioactivity of RLI Released from Microsphere Conjugate

After RLI is released from the microsphere conjugate, an aminopropyl remnant remains at the site of conjugation. To test the bioactivity of the released [aminopropyl]-RLI, cell-based assays were used determine the ability for the [aminopropyl]-RLI to induce receptor dimerization compared to that of native RLI. The EC$_{50}$ curves of native RLI and [aminopropyl]-RLI overlay with one another, indicating the aminopropyl remnant does not affect IL-15 activity, as assessed in this bioactivity assay (FIG. 16).

FIG. 16 shows the results of a IL-2Rβγ receptor-binding cell-based assay for RLI. A U2OS cell-based assay was used to determine the binding activity of aminopropyl-RLI released from the conjugate at pH 7.4 (EC$_{50}$=180 µM) compared to that of native RLI (EC$_{50}$=160 µM).

Example 15

Pharmacokinetics of [Aminopropyl]-RLI Released from Microsphere Conjugate

Pharmacokinetics of [aminopropyl]-RLI released from the microsphere conjugate were measured in normal C57BL/6J mice. Mice were given a subcutaneous injection of conjugate (1.5 nmol protein, 100 µL injection). Blood draws were taken at pre-determined time points over a period of ten days and the plasma was prepared. The concentration of [aminopropyl]-RLI in the plasma was determined using ELISAs specific for RLI (FIG. 17). Manual inspection of the data suggests a Tmax of 48 hours and fit of the data to a single-phase decay model resulted in a half-life of 135 hours. There was no change in the body weight of the mice (initial weight: 21.5±1.1 g; final weight: 21.5±1.1 g).

FIG. 17 shows the pharmacokinetics of [aminopropyl]-RLI released from microsphere conjugate in C57BL/6J mice. Normal, male C57BL/6J mice were dosed with microsphere-RLI conjugate (1.5 nmol). Plasma samples were prepared and analyzed using R&D systems DuoSet hIL15/IL15Rα complex ELISA (DY6924). Data fit to a single-phase decay model resulting in a half-life of 135 hours.

Example 16

Pharmacodynamics of [Aminopropyl]-RLI Released from Microsphere Conjugate

The pharmacodynamics of the MS-RLI conjugate (34 µg, 1.5 nmol) was compared to that of empty MSs, and free RLI (2.5 µg, QDx4) in C57Black mice (n=5/group). Blood draws were taken over 13 days and the PBMCs surface stained using general laboratory procedures. Fixation and intracellular staining followed protocols from the eBioscience Foxp3/Transcription Factor Staining Buffer Set (ThermoFisher Scientific). Commercial antibodies used were against NK1.1, CD3, CD8, CD19, CD44 and Ki-67 expressing cells. Stained single cell suspension were analyzed using a LSRII flow cytometer (BD Biosciences) and analyzed using FlowJo cytometry analysis software (TreeStar, Ashland, Oreg.). Cell populations of particular interest were CD8+ memory T cells (CD44$^{hi}$CD8+), natural killer (CD3-NK1.1+) cells, proliferating CD8+ memory T cells (CD44$^{hi}$CD8+Ki-67+), and proliferating natural killer (CD3-NK1.1+Ki-67+) cells.

An increase in CD44$^{hi}$CD8$^+$ T cells was noticeable 5 days post treatment for the MS-RLI and native RLI groups (FIG. 18A). This cell population was not maintained by the native RLI and the population returned to baseline levels by day 7. This was expected due to short half-life (t$_1$n=3 h) and rapid clearance of free RLI. The MS-RLI conjugate sustained the CD44$^{hi}$CD8$^+$ T cells levels through 13 days post treatment. All 5 mice that were administered the MS-RLI conjugated developed injection site lesions and euthanasia was required.

The proliferation of CD8$^+$ T cells was determined by the proliferation marker Ki-67. Three days post injection, an increase in CD8$^+$ T cells was observed compared to the control (FIG. 18B). The percentage of proliferating CD8$^+$ T cells peaked at 5 days for all groups, followed by a rapid return to baseline.

An increase in the percentage of NK cells was also observed with mice dosed with the MS-RLI conjugate compared to the control and native RLI (FIG. 19A). The free RLI injections and MS-RLI conjugate resulted in ~4-fold and ~15-fold increase in the percentage of NK cells in the PBMCs, respectively. The NK cell levels returned to baseline by ten days post treatment for all groups. The proliferation of NK cells significantly increased three days post treatment and was maintained through five days for each group (FIG. 19B). The proliferation of NK cells returned to baseline by 7 days post treatment.

Example 17

Preparation of Degradable PEG-hydrogels

1st prepolymer

+

2nd prepolymer hydrogel

Hydrogels of the invention are prepared by polymerization of two prepolymers comprising groups C and C' that react to form a connecting functional group, C*. The prepolymer connection to one of C or C' further comprises a cleavable linker introduced by reaction with cleavable linker, such as a linker of Formula (Ia) as disclosed herein, so as to introduce the cleavable linker into each crosslink of the hydrogel.

In one embodiment, a first prepolymer comprises a 4-armed PEG wherein each arm is terminated with an adapter unit having two mutually-unreactive ("orthogonal") functional groups B and C. B and C may be initially present in protected form to allow selective chemistry in subsequent steps. In certain embodiments, the adapter unit is a derivative of an amino acid, particularly lysine, cysteine, aspartate, or glutamate, including derivatives wherein the alpha-amine group has been converted to an azide, for example mono-esters of 2-azidoglutaric acid. The adapter unit is connected to each first prepolymer arm through a connecting functional group A*, formed by condensation of a functional group A on each prepolymer arm with cognate functional group A' on the adapter unit. A second prepolymer comprises a 4-armed PEG wherein each arm is terminated with a functional group C' having complimentary reactivity with group C of the first prepolymer, such that crosslinking between the two prepolymers occurs when C and C' react to form C*.

As an illustrative example, a first prepolymer was prepared as follows. H-Lys(Boc)-OH was acylated with a linker of formula (IIa) wherein Z=azide to give an adapter unit where A=COOH, B=Boc-protected $NH_2$, and C=azide. This was coupled to 20-kDa 4-armed PEG-tetraamine, and the Boc group was removed to provide a first prepolymer wherein A*=amide, B=$NH_2$, and C=azide and wherein a cleavable linker of formula (IIa) is incorporated into the linkage between each arm and group C of the first prepolymer. The corresponding second prepolymer was prepared by acylation of 20-kDa 4-armed PEG-tetraamine with 5-cyclooctynyl succinimidyl carbonate to give a second prepolymer wherein C'=cyclooctyne. Upon mixing of the first and second prepolymers, reaction of the C=azide and C'=cyclooctyne groups form corresponding triazole groups and thereby crosslink the two prepolymers into a 3-dimensional network, with each crosslink comprising a cleavage linker resulting from incorporation of the compound of Formula (IIa), and wherein each node resulting from incorporation of a first prepolymer comprises a remaining functional group B=$NH_2$ which can be derivatized for attachment of further linkers, drugs, fluorophores, metal chelators, and the like.

All publications, including patents, patent applications, and scientific articles, mentioned in this specification are herein incorporated by reference in their entirety for all purposes to the same extent as if each individual publication, including patent, patent application, or scientific article, were specifically and individually indicated to be incorporated by reference.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

---

The invention claimed is:

1. A hydrogel of the formula $$M\left[\!\!\begin{array}{c} \\ Z^*\!-\!S\!-\!(CH_2)_n\!-\!\overset{\displaystyle R^4}{\underset{\displaystyle R^4}{C}}\!-\!\overset{\displaystyle HC\!-\!R^2}{\underset{\displaystyle H}{C}}\!-\!O\!-\!\overset{\displaystyle O}{\overset{\|}{C}}\!-\!Y\!-\!D \\ \\ \end{array}\!\!\right]_q$$

wherein:

M is a macromolecular carrier;

q is an integer from 1 to 10 when M is a soluble macromolecular carrier or q is a multiple number in a suitable ratio to M when M is an insoluble macromolecular carrier;

Z* is a connecting group comprising an amide, oxime, triazole, thioether, thiosuccinimide, or ether;

n is an integer from 0 to 6;

$R^1$ is-CN, —$NO_2$, —$COR^5$, —$SOR^5$, or —$SO_2R^5$, wherein $R^5$ is $C_1$-$C_6$ alkyl, aryl, heteroaryl, or $NR^6{}_2$, wherein each $R^6$ is independently $C_1$-$C_6$ alkyl, aryl, or heteroaryl, and wherein $R^5$ and $R^6$ are independently optionally substituted;

$R^2$ is H or alkyl;

each $R^4$ is independently H or $C_1$-$C_3$ alkyl or the two $R^4$ are taken together with the carbon atom to which they attach to form a 3-6 membered ring;

S is absent or $(CH_2CH_2O)_h(CH_2)_g CONH$ wherein g=1-6 and h=0-1000;

Y is NH $(CH_2CH_2O)_p(CH_2)_m$ wherein m=2-6 and p=0-1000; and

D is an interleukin-15 (IL-15) or a fusion protein of interleukin-15 with an interleukin-15 Rα sushi domain (IL-15·IL-15RαSu).

2. The hydrogel of claim 1, wherein Z* is a triazole moiety.

3. The hydrogel of claim 1, wherein $R^1$ is —CN or —$SO_2R^5$, wherein $R^5$ is $C_1$-$C_6$ alkyl, aryl, heteroaryl, or $NR^6{}_2$, wherein each $R^6$ is independently $C_1$-$C_6$ alkyl, aryl, or heteroaryl, and $R^2$ is H.

4. The hydrogel of claim 3, wherein $R^1$ is —CN, —$SO_2N$ $(CH_3)_2$, —$SO_2CH_3$, —$SO_2Ph$, —$SO_2PhCl$, $SO_2CH(CH_3)_2$, —$SO_2N(CH_3)(CH_2CH_3)$, —$SO_2N(CH_2CH_2OCH_3)_2$, or

5. The hydrogel of claim 1, wherein $R^2$ is H.

6. The hydrogel of claim 1, wherein n is 4, each $R^4$ is H, $R^1$ is $-SO_2R^5$ wherein $R^5$ is methyl, $R^2$ is H, S is $(CH_2CH_2O)_h(CH_2)_gCONH$ wherein g=2 and h=4, and Y is $NH (CH_2CH_2O)_p(CH_2)_m$ wherein m=3 and p=0.

7. The hydrogel of claim 1, wherein M comprises polymers having multi-armed chains.

8. The hydrogel of claim 7, wherein M comprises r-armed polymers, wherein r is an integer from 2 to 8.

9. The hydrogel of claim 8, wherein r is 4.

10. The hydrogel of claim 8, wherein the r-armed polymers are pegylated polymers.

11. The hydrogel of claim 10, wherein r is 4.

12. The hydrogel of claim 8, wherein the r-armed polymers are linked through a cleavable linker.

13. A hydrogel comprising repeating units of the formula:

wherein:

$P^1$ and $P^2$ are independently r-armed polymers wherein r is an integer from 2 to 8;

A* is a connecting group comprising carboxamide, oxime, ether, thioether or triazole;

C* is a connecting group comprising carboxamide, oxime, ether, thioether or triazole;

each n is independently an integer from 0 to 6;

x, y, and z are independently an integer from 0 to 6;

$R^{11}$ is-CN, $-NO_2$, $-COR^5$, $-SOR^5$, or $-SO_2R^5$, wherein $R^5$ is $C_1$-$C_6$ alkyl, aryl, heteroaryl, or $NR^6_2$, wherein each $R^6$ is independently $C_1$-$C_6$ alkyl, aryl, or heteroaryl;

$R^{12}$ is H or alkyl;

each $R^{14}$ is independently $C_1$-$C_3$ alkyl or the two $R^{14}$ are taken together with the carbon atom to which they attach to form a 3-6 membered ring;

Z* is a connecting group comprising a carboxamide, amide, oxime, triazole, thioether, thiosuccinimide, or ether;

S is absent or $(CH_2CH_2O)_h(CH_2)_gCONH$ wherein g=1-6 and h=0-1000;

Y is $NH (CH_2CH_2O)_p(CH_2)_m$ wherein m=2-6 and p=0-100;

$R^1$ is $-CN$, $-NO_2$, $-COR^5$, $-SOR^5$, or $-SO_2R^5$, wherein $R^5$ is $C_1$-$C_6$ alkyl, aryl, heteroaryl, or $NR^6_2$, wherein each $R^6$ is independently $C_1$-$C_6$ alkyl, aryl, or heteroaryl;

$R^2$ is H or alkyl;

each $R^4$ is independently H or $C_1$-$C_3$ alkyl or the two $R^4$ are taken together with the carbon atom to which they attach to form a 3-6 membered ring; and D is an IL-15 or an IL-15·IL-15RπSu fusion protein.

14. The hydrogel of claim 13, wherein $P^1$ and $P^2$ are pegylated polymers.

15. The hydrogel of claim 13, wherein r is 4.

16. The hydrogel of claim 13, wherein A* and C* are independently carboxamide, oxime, ether, thioether or triazole.

17. The hydrogel of claim 13, wherein both $R^{14}$ groups are methyl.

18. The hydrogel of claim 13 of the formula:

*  *  *  *  *